(12) United States Patent
Makarov et al.

(10) Patent No.: US 6,197,557 B1
(45) Date of Patent: Mar. 6, 2001

(54) COMPOSITIONS AND METHODS FOR ANALYSIS OF NUCLEIC ACIDS

(75) Inventors: Vladimir L. Makarov; John P. Langmore, both of Ann Arbor, MI (US)

(73) Assignee: The Regents of the University of Michigan, Ann Arbor, MI (US)

(*) Notice: Subject to any disclaimer, the term of this patent is extended or adjusted under 35 U.S.C. 154(b) by 0 days.

(21) Appl. No.: 09/151,236

(22) Filed: Sep. 10, 1998

Related U.S. Application Data

(63) Continuation-in-part of application No. 09/035,677, filed on Mar. 5, 1998, now abandoned, which is a continuation-in-part of application No. 08/811,804, filed on Mar. 6, 1997, now Pat. No. 6,117,634.

(51) Int. Cl.$^7$ .............................. C12P 19/34; C12Q 1/68; C07H 21/02; C07H 21/04
(52) U.S. Cl. ........................... 435/91.2; 435/6; 536/23.1; 536/24.3
(58) Field of Search ..................... 435/6, 91.2; 536/23.1, 536/24.3

(56) References Cited

U.S. PATENT DOCUMENTS

| | | |
|---|---|---|
| 4,942,124 | 7/1990 | Church . |
| 5,112,736 | 5/1992 | Caldwell et al. . |
| 5,149,625 | 9/1992 | Church et al. . |
| 5,418,149 | 5/1995 | Gelfand et al. . |
| 5,489,508 | 2/1996 | West et al. . |
| 5,503,980 | 4/1996 | Cantor . |
| 5,506,100 | 4/1996 | Surzycki et al. . |
| 5,552,278 | 9/1996 | Brenner . |
| 5,599,675 | 2/1997 | Brenner . |
| 5,604,098 | 2/1997 | Mead et al. . |
| 5,645,986 | 7/1997 | West et al. . |
| 5,648,215 | 7/1997 | West et al. . |
| 5,686,245 | 11/1997 | West et al. . |
| 5,686,306 | 11/1997 | West et al. . |
| 5,693,474 | 12/1997 | Shay et al. . |
| 5,693,613 | 12/1997 | Shay et al. . |
| 5,695,932 | 12/1997 | West et al. . |
| 5,707,795 | 1/1998 | West et al. . |
| 5,714,318 | 2/1998 | Sagner et al. . |
| 5,714,330 | 2/1998 | Brenner et al. . |
| 5,741,677 | 4/1998 | Kozlowski et al. . |
| 5,750,341 | 5/1998 | Macevicz . |

FOREIGN PATENT DOCUMENTS

| | | |
|---|---|---|
| 0 415 755 A2 | 3/1991 | (EP) . |
| 0 439 182 A2 | 7/1991 | (EP) . |
| 0 415 755 A3 | 8/1991 | (EP) . |
| 0 439 182 A3 | 10/1991 | (EP) . |
| 0 497 272 A1 | 8/1992 | (EP) . |
| 0 684 315 A1 | 3/1995 | (EP) . |
| 0 497 272 B1 | 10/1995 | (EP) . |
| 0 415 755 B1 | 12/1995 | (EP) . |
| 0 439 182 B1 | 4/1996 | (EP) . |
| WO 86/07612 | 12/1986 | (WO) . |
| WO 90/13666 | 11/1990 | (WO) . |
| WO 93/02212 | 2/1993 | (WO) . |
| WO 93/21340 | 10/1993 | (WO) . |
| WO 93/24654 | 12/1993 | (WO) . |
| WO 94/24313 | 10/1994 | (WO) . |
| WO 95/06752 | 3/1995 | (WO) . |
| WO 96/32504 | 10/1996 | (WO) . |
| WO 97/03210 | 1/1997 | (WO) . |
| WO 98/15644 | 4/1998 | (WO) . |
| WO 98/15652 | 4/1998 | (WO) . |
| WO 98/39485 | 9/1998 | (WO) . |

OTHER PUBLICATIONS

Broude et al., "Enhanced DNA sequencing by hybridization," *Proc. Natl. Acad. Sci. USA*, 91:3072–3076, Apr., 1994.

Fu et al., "A DNA sequencing strategy that requires only five bases of known terminal sequence for priming," *Proc. Natl. Acad. Sci. USA*, 92:10162–10166, Oct., 1995.

Fu et al., "Sequencing double–stranded DNA by strand displacement," *Nucl. Acids Res.*, 25(3):677–679, Feb., 1997.

Makarov et al., "Long G tails at both ends of human chromosomes suggest a C strand degradation mechanism for telomere shortening," *Cell*, 88:657–666, Mar. 7, 1997.

Wellinger et al., "Evidence for a new step in telomere maintenance," *Cell*, 85:423–433, 1996.

Wellinger et al., "Origin activation and formation of single strand $TG_{1-3}$ tails occur sequentially in late S phase on a yeast linear plasmid," *Mol. Cell. Biol.*, 13:4057–4065, 1993.

Wellinger et al., "Sacharomyces telomeres aquire single–strand $TG_{1-3}$ tails late in S phase," *Cell*, 72:51–60, 1993.

Wellinger et al., "Use of non–denaturing Southern hybridization and two dimensional agarose gels to detect putative intermediates in telomere replication in *Sacharomyces cerevisae*," *Chromosoma*, 102, S150–S156, 1992.

Ehrlich, et al. "The specificity of pancreatic deoxyribonuclease," *Eur J Biochem.* 40:143–147, 1973.

Kovacs et al., "The generation of a single nick per plasmic molecule using restriction endonucleases with multiple recognition sites," *Gene*, 29:63, 1984.

(List continued on next page.)

Primary Examiner—John S. Brusca
Assistant Examiner—Young Kim
(74) Attorney, Agent, or Firm—Fulbright & Jaworski, LLP

(57) ABSTRACT

Disclosed are a number of methods that can be used in a variety of embodiments, including, creation of a nucleic acid terminated at one or more selected bases, sequence analysis of nucleic acids, mapping of sequence motifs within a nucleic acid, positional mapping of nucleic acid clones, and analysis of telomeric regions. The methods utilize double-stranded templates, and in most aspects involve a strand replacement reaction initiated at one or more random or specific locations created in a nucleic acid molecule, and in certain aspects utilizing an oligonucleotide primer.

46 Claims, 38 Drawing Sheets

OTHER PUBLICATIONS

Meyer and Geider, "Bacteriophage fd gene II–protein. I. Purification, involvement in RF replication, and the expression of gene II," *J. Biol. Chem.*, 254:12636, 1979.

Olsen et al., "Investigation of the inhibitory role of phosphorothioate internucleotidic linkages on the catalytic activity of the restriction endonuclease EcoRV," *Biochem.*, 29:9546, 1990.

Co–pending U.S. application No. 08/811,804, filed Mar. 5, 1997 (Attorney Docket No. UMIC:026–1).

Labeit et al., "Laboratory methods: A new method of DNA sequencing using deoxynucleotide α–thiotriphosphates," *DNA*, 5(2):173–177, 1986.

Porter et al., "Direct PCR sequencing with boronated nucleotides," *Nucl. Acids Res.*, 25(8):1611–1617, 1997.

Lindahl, "DNA Glycosylases, Endonucleases for Apurinic/Apyrimidinic Sites, and Base Excision–Repair," *Prog. Nucleic Acid Res. Mol. Biol.* 22:135–192, 1979.

U.S application No. 09/035,677 filed Mar. 5, 1997 (Abandoned: Attorney Docket No. UMIC:027).

Chiu et al., "Differential dependence on chromatin structure for copper and iron induction of DNA double–strand breaks," *Biochemistry* 34:2653–2661, 1995.

Fitzgerald et al., "Rapid shotgun cloning utilizing the two base recognition endonuclease CviJI," *Nucl. Acids Res.* 20:3753–3762, 1992.

Gish and Eckstein, "DNA and RNA sequence determination based on phosphorothioate chemistry," *Science* 240: 1520–1522, 1988.

Grecz et al., "Freeze–thaw injury: evidence for double–strand breaks in *Escherichia coli* DNA," *Biochem. Biophys. Res. Comm.* 93:1110–1113, 1980 (Medline abstract).

Matsugo et al., "DNA strand scission and cell–killing activity of hydroperoxynaphthalimide derivatives upon photoirradiation," Nucl. Acids Symp. Ser. 25:109–110, 1991 (HCA abstract).

reaction time (min)

with dUTP   with dTTP 0           1

10          1

20          1

30          1

40          1

▒▒▒ = thymidine-containing DNA synthesized by PENT
yyy = uridine-containing DNA synthesized by PENT

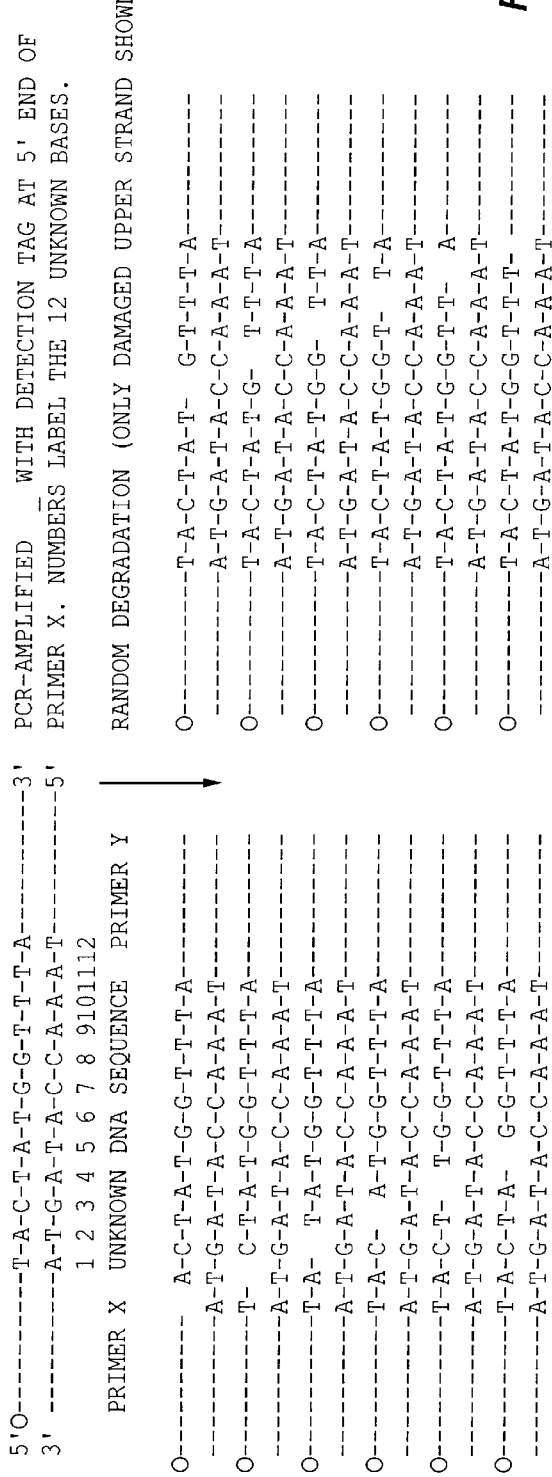
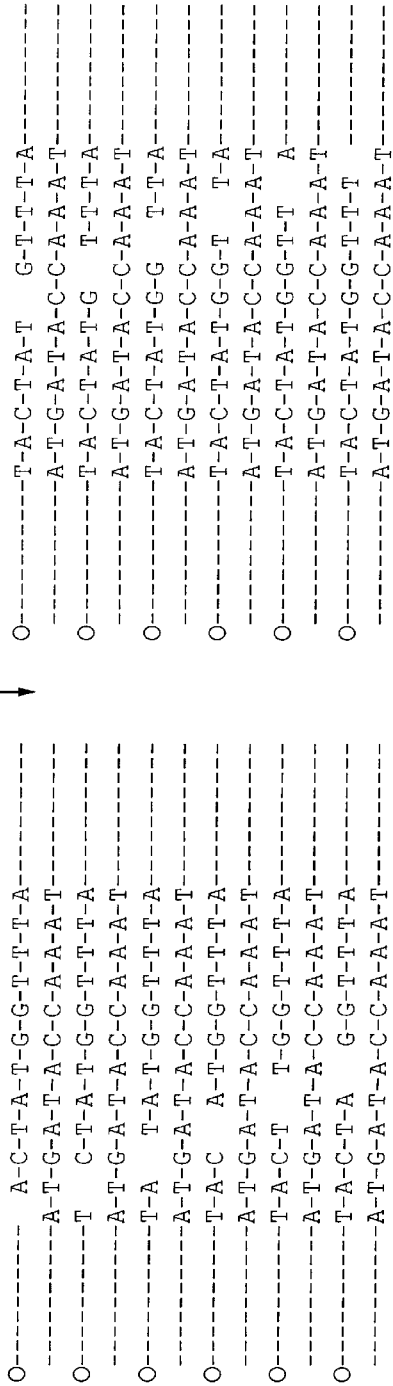
FIG. 15A
FIG. 15

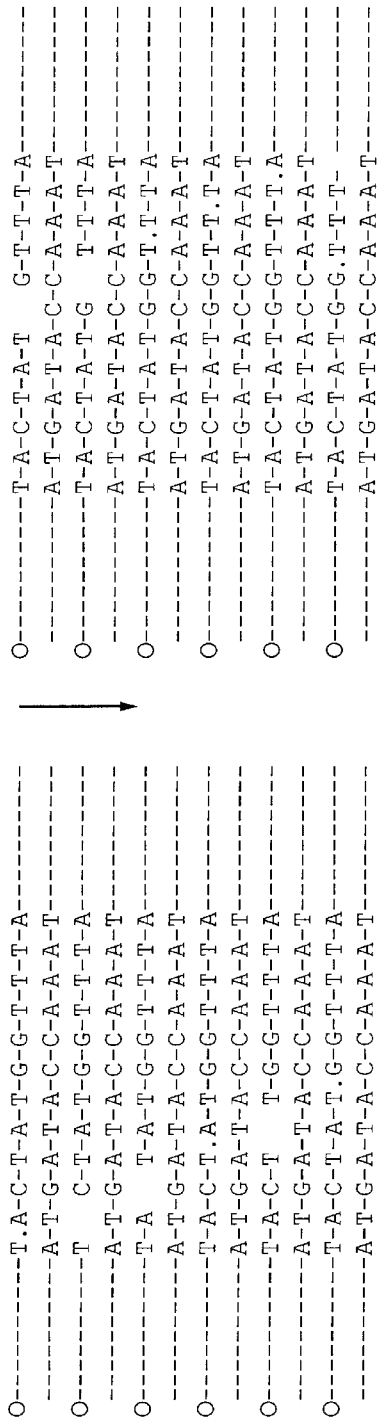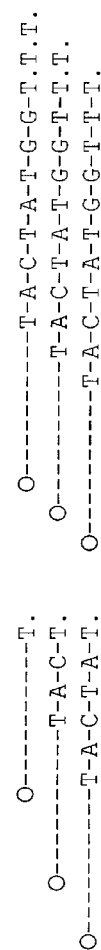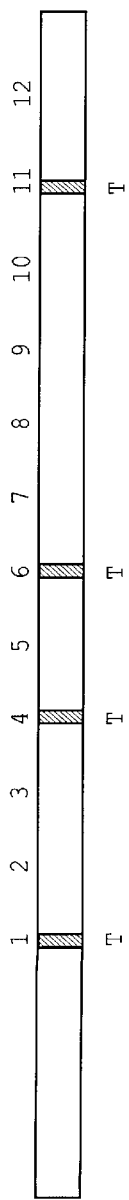
FIG. 17B

FIG. 19A

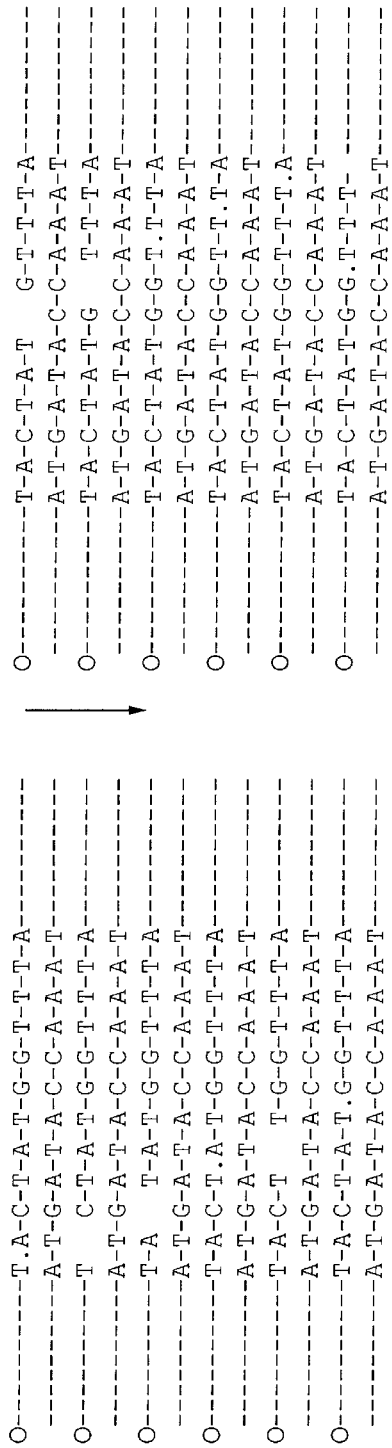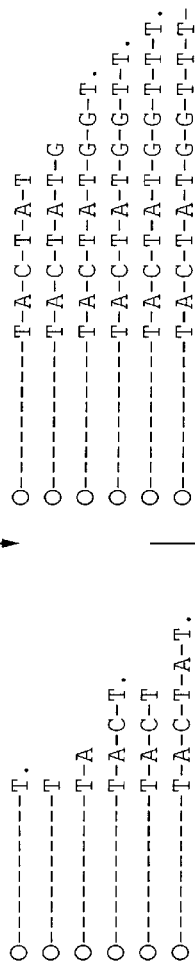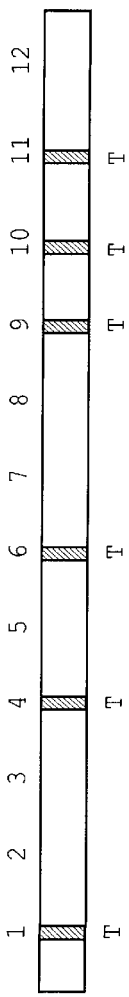
FIG. 19B

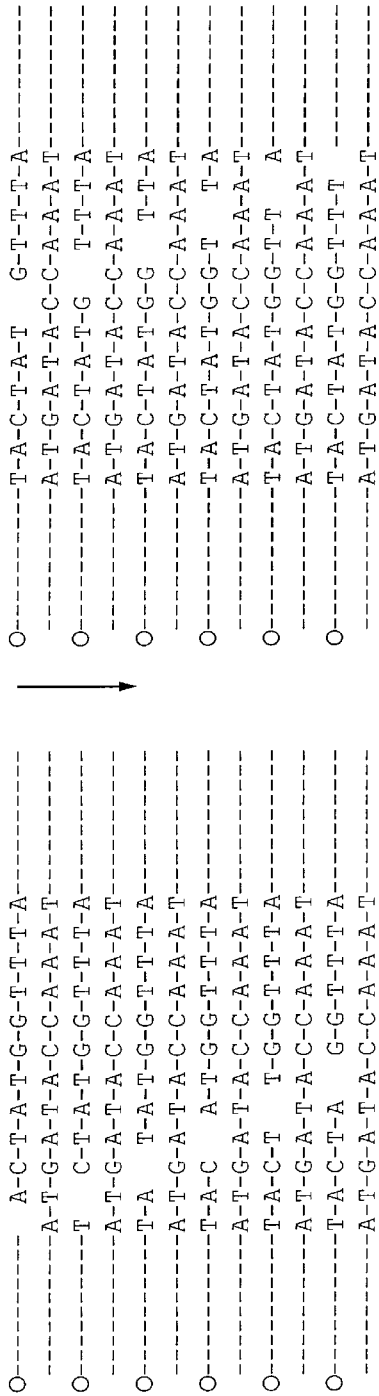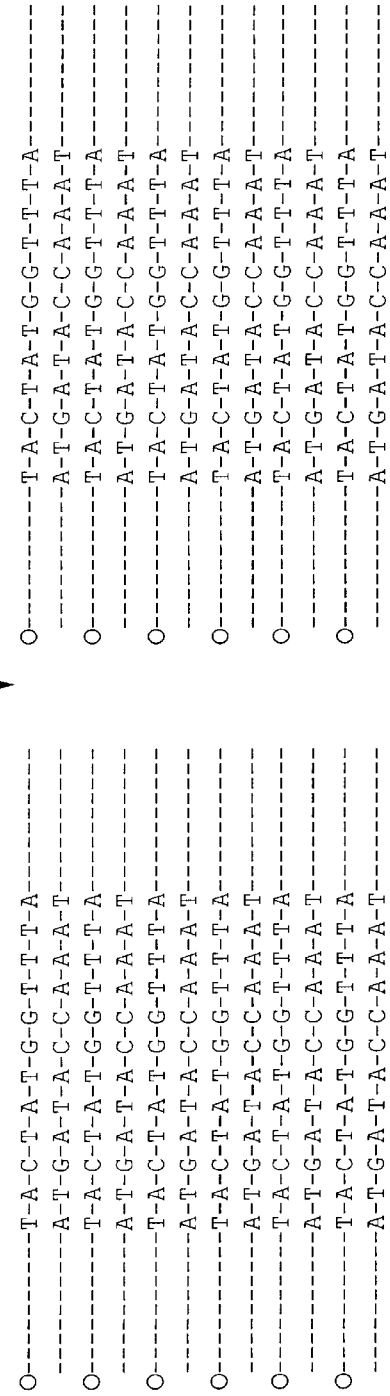
FIG. 21A
FIG. 21

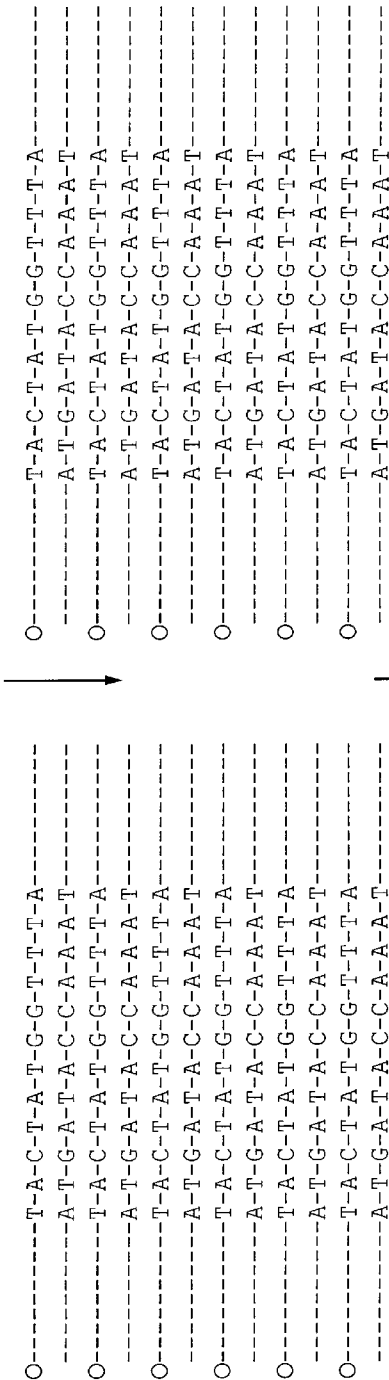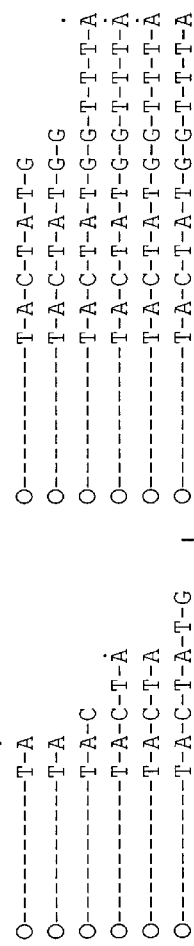
FIG. 21B

T A C T A T G G T (T) T A

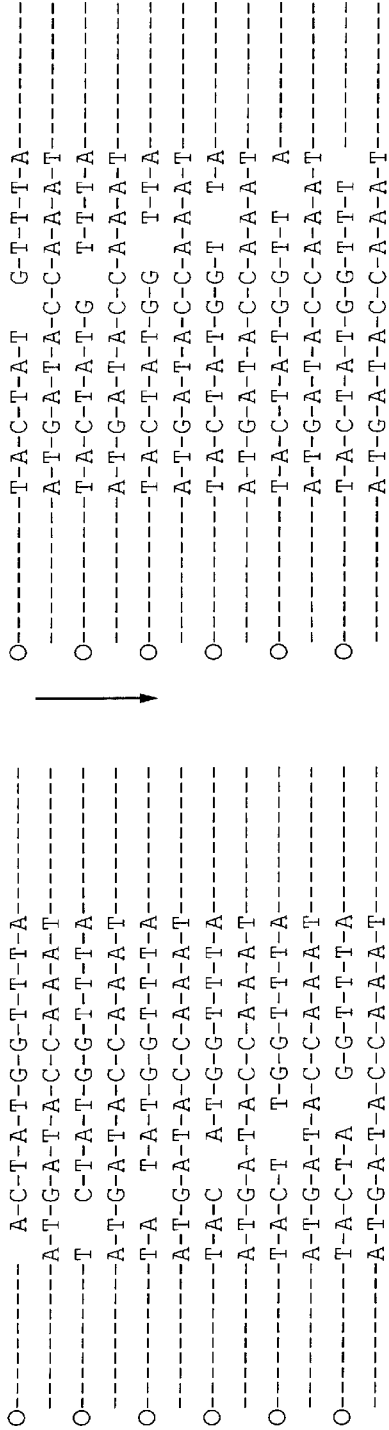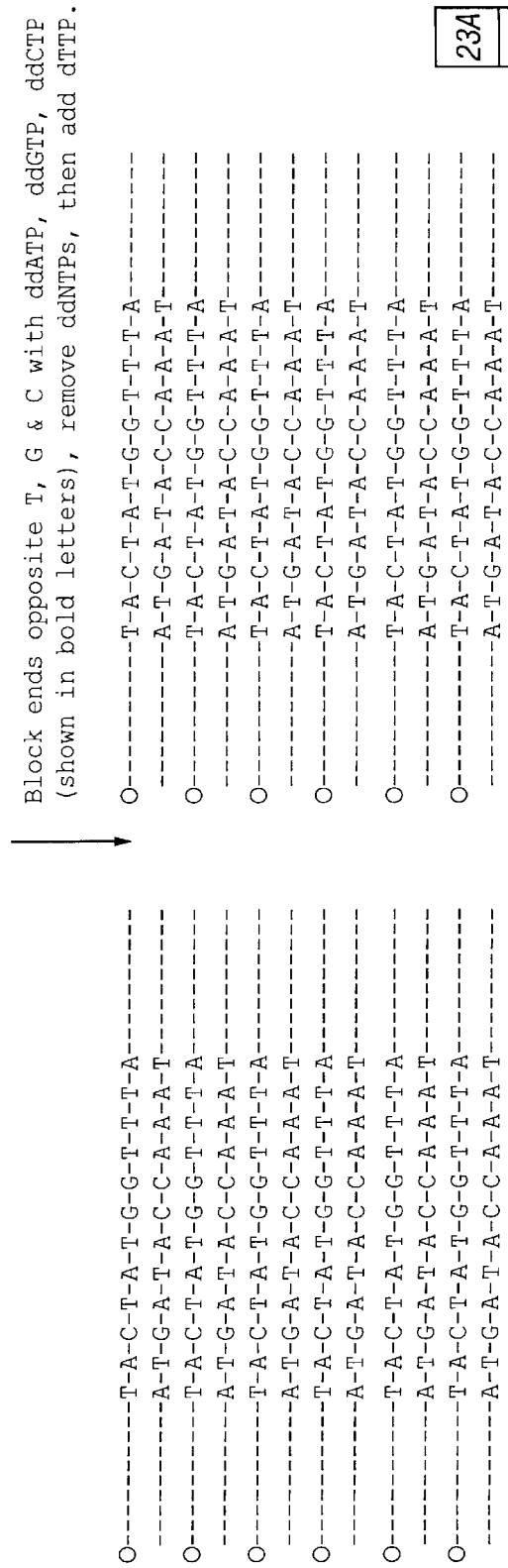
FIG. 23A

FIG. 23B

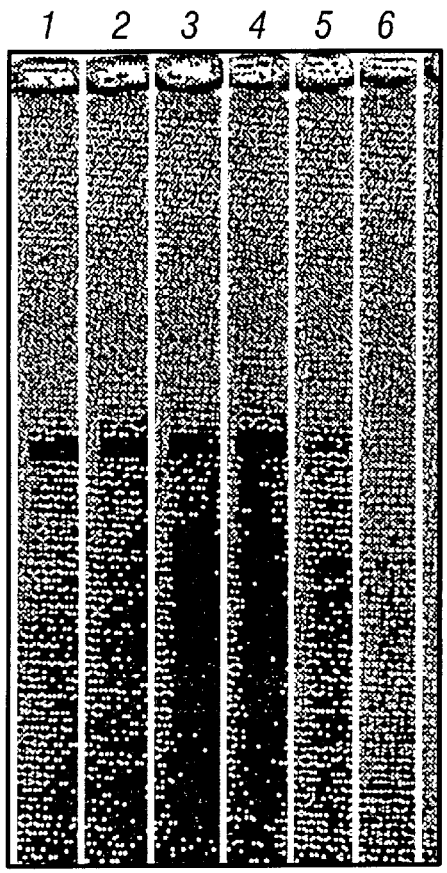
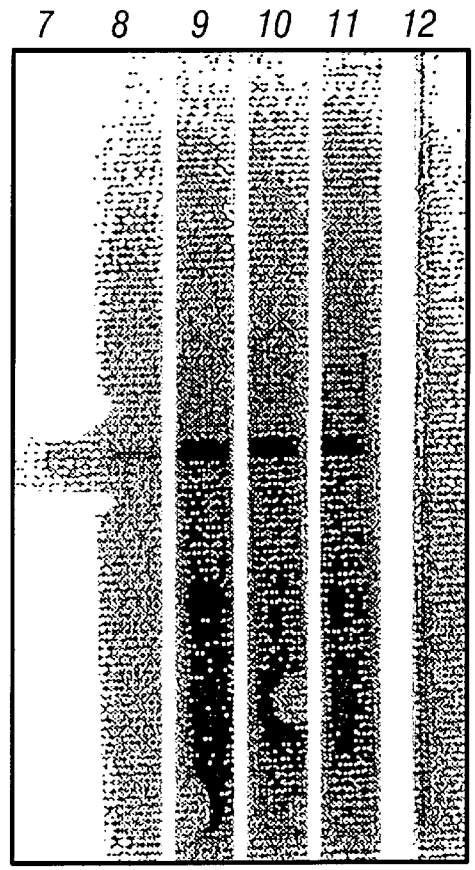
FIG. 28A
FIG. 28B

COMPOSITIONS AND METHODS FOR ANALYSIS OF NUCLEIC ACIDS

The present application is a continuation-in-part of U.S. patent application Ser. No. 09/035,677, now abandoned, filed Mar. 5, 1998, which is a continuation-in-part of U.S. patent application Ser. No. 08/811,804 filed Mar. 6, 1997, now U.S. Pat. No. 6,117,634, the entire texts of which are specifically incorporated herein by reference without disclaimer.

The government owns rights in the present invention pursuant to grant number MCB 9514196 from the National Science Foundation.

BACKGROUND OF THE INVENTION

1. Field of the Invention

The present invention relates generally to the field of nucleic acid analysis. More particularly, it concerns the sequencing and mapping of double-stranded nucleic acid templates.

2. Description of Related Art

An aggressive research effort to sequence the entire human genome is proceeding in the laboratories of genetic researchers throughout the country. The project is called the Human Genome Project (HGP). It is a daunting task given that it involves the complete characterization of the archetypal human genome sequence which comprises $3 \times 10^9$ DNA nucleotide base pairs. Early estimates for completing the task within fifteen years hinged on the expectation that new technology would be developed in response to the pressing need for faster methods of DNA sequencing and improved DNA mapping techniques.

Currently physical mapping is used to identify overlapping clones of DNA so that all of the DNA in a particular region can be sequenced or otherwise studied. There are two basic techniques of physical mapping. First, all candidate overlapping clones can be restricted with a series of restriction enzymes and the restriction fragments separated by gel electrophoresis. Overlapping clones will share some DNA sequences and thus some common restriction fragments. By comparing the restriction fragment lengths from a number of clones, the extent of overlap between any two clones can be determined. This process is very tedious and can only evaluate a limited number of candidate clones. Second, if a large number of sequence tagged sites are known in the region studied, the DNA from those sequence tagged sites can be labeled and hybridized to the candidate clones. Clones that hybridize to the same sequence tagged sites are identified as overlapping. If many sequence tagged sites are shared between two clones, it is assumed that the overlap is extensive. Sequence tagged sites give a lot of information from a limited number of hybridization reaction, however, most regions of most genomes do not have extensive sequence tagged site resources. Both methods suffer from lack of direct correspondence between the sequence and the restriction sites or sequence tagged site locations.

Current DNA sequencing approaches generally incorporate the fundamentals of either the Sanger sequencing method or the Maxam and Gilbert sequencing method, two techniques that were first introduced in the 1970's (Sanger et al., 1977; Maxam and Gilbert, 1977). In the Sanger method, a short oligonucleotide or primer is annealed to a single-stranded template containing the DNA to be sequenced. The primer provides a 3' hydroxyl group which allows the polymerization of a chain of DNA when a polymerase enzyme and dNTPs are provided. The Sanger method is an enzymatic reaction that utilizes chain-terminating dideoxynucleotides (ddNTPs). ddNTPs are chain-terminating because they lack a 3'-hydroxyl residue which prevents formation of a phosphodiester bond with a succeeding deoxyribonucleotide (dNTP). A small amount of one ddNTP is included with the four conventional dNTPs in a polymerization reaction. Polymerization or DNA synthesis is catalyzed by a DNA polymerase. There is competition between extension of the chain by incorporation of the conventional dNTPs and termination of the chain by incorporation of a ddNTP.

The original version of the Sanger method utilized the *E. coli* DNA polymerase I ("pol I"), which has a polymerization activity, a 3'–5' exonuclease proofreading activity, and a 5'–3' exonuclease activity. Later, an improvement to the method was made by using Klenow fragment instead of pol I; Klenow lacks the 5'–3' exonuclease activity that is detrimental to the sequencing reaction because it leads to partial degradation of template and product DNA. The Klenow fragment has several limitations when used for enzymatic sequencing. One limitation is the low processivity of the enzyme, which generates a high background of fragments that terminate by the random dissociation of the enzyme from the template rather than by the desired termination due to incorporation of a ddNTP. The low processivity also means that the enzyme cannot be used to sequence nucleotides that appear more than ~250 nucleotides from the 5' end of the primer. A second limitation is that Klenow cannot efficiently utilize templates which have homopolymer tracts or regions of high secondary structure. The problems caused by secondary structure in the template can be reduced by running the polymerization reaction at 55° C. (Gomer and Firtel, 1985).

Improvements to the original Sanger method include the use of polymerases other than the Klenow fragment. Reverse transcriptase has been used to sequence templates that have homopolymeric tracts (Karanthanasis, 1982; Graham et al., 1986). Reverse transcriptase is somewhat better than the Klenow enzyme at utilizing templates containing homopolymer tracts.

The use of a modified T7 DNA polymerase (Sequenase™) was a significant improvement to the Sanger method (Sambrook et al., 1989; Hunkapiller, 1991). T7 DNA polymerase does not have any inherent 5'–3' exonuclease activity and has a reduced selectivity against incorporation of ddNTP. However, the 3'–5' exonuclease activity leads to degradation of some of the oligonucleotide primers. Sequenase™ is a chemically-modified T7 DNA polymerase that has reduced 3' to 5' exonuclease activity (Tabor et al., 1987). Sequenase™ version 2.0 is a genetically engineered form of the T7 polymerase which completely lacks 3' to 5' exonuclease activity. Sequenase™ has a very high processivity and high rate of polymerization. It can efficiently incorporate nucleotide analogs such as dITP and 7-deaza-dGTP which are used to resolve regions of compression in sequencing gels. In regions of DNA containing a high G+C content, Hoogsteen bond formation can occur which leads to compressions in the DNA. These compressions result in aberrant migration patterns of oligonucleotide strands on sequencing gels. Because these base analogs pair weakly with conventional nucleotides, intrastrand secondary structures during electrophoresis are alleviated. In contrast, Klenow does not incorporate these analogs as efficiently.

The use of Taq DNA polymerase and mutants thereof is a more recent addition to the improvements of the Sanger method (U.S. Pat. No. 5,075,216). Taq polymerase is a thermostable enzyme which works efficiently at 70–75° C.

The ability to catalyze DNA synthesis at elevated temperature makes Taq polymerase useful for sequencing templates which have extensive secondary structures at 37° C. (the standard temperature used for Klenow and Sequenase™ reactions). Taq polymerase, like Sequenase™, has a high degree of processivity and like Sequenase 2.0, it lacks 3' to 5' nuclease activity. The thermal stability of Taq and related enzymes (such as Tth and Thermosequenase™) provides an advantage over T7 polymerase (and all mutants thereof) in that these thermally stable enzymes can be used for cycle sequencing which amplifies the DNA during the sequencing reaction, thus allowing sequencing to be performed on smaller amounts of DNA. Optimization of the use of Taq in the standard Sanger method has focused on modifying Taq to eliminate the intrinsic 5'–3' exonuclease activity and to increase its ability to incorporate ddNTPs (EP 0 655 506 B1).

Both the Sanger and the Maxim-Gilbert methods produce populations of radiolabelled or fluorescently labeled polynucleotides of differing lengths which are separated according to size by polyacrylamide gel electrophoresis (PAGE). The nucleotide sequence is determined by analyzing the pattern of size-separated radiolabelled polynucleotides in the gel. The Maxim-Gilbert method involves degrading DNA at a specific base using chemical reagents. The DNA strands terminating at a particular base are denatured and electrophoresed to determine the positions of the particular base. By combining the information from fragments terminating at different bases or combinations of bases the entire DNA sequence can be reconstructed. However, the Maxim-Gilbert method involves dangerous chemicals, and is time- and labor-intensive. Thus, it is no longer used for most applications.

The current limitations to conventional applications of the Sanger method include 1) the limited resolving power of polyacrylamide gel electrophoresis, 2) the formation of intermolecular and intramolecular secondary structure of the denatured template in the reaction mixture, which can cause any of the polymerases to prematurely terminate synthesis at specific sites or misincorporate ddNTPs at inappropriate sites, 3) secondary structure of the DNA on the sequencing gels can give rise to compressions of the electrophoretic ladder at specific locations in the sequence, 4) cleavage of the template, primers and products with the 5'–3' or 3'–5' exonuclease activities in the polymerases, and 5) mispriming of synthesis due to hybridization of the oligonucleotide primers to multiple sites on the denatured template DNA. The formation of intermolecular and intramolecular secondary structure produces artificial terminations that are incorrectly "read" as the wrong base, gives rise to bands across four lanes (BAFLs) that produce ambiguities in base reading, and decrease the intensity and thus signal-to-noise ratio of the bands. Secondary structure of the DNA on the gels can largely be solved by incorporation of dITP or 7-deaza-dGTP into the synthesized DNA; DNA containing such modified NTPs is less likely to form urea-resistant secondary structure during electrophoresis. Cleavage of the template, primers or products leads to reduction in intensity of bands terminating at the correct positions and increase the background. Mispriming gives rise to background in the gel lanes.

The net result is that, although the inherent resolution of polyacrylamide gel electrophoresis alone is as much as 1000 nucleotides, it is common to only be able to correctly read 400–600 nucleotides of a sequence (and sometimes much less) using the conventional Sanger Method, even when using optimized polymerase design and reaction conditions. Some sequences such as repetitive DNA, strings of identical bases (especially guanines, GC-rich sequences and many unique sequences) cannot be sequenced without a high degree of error or uncertainty.

In the absence of any methods to consistently sequence DNA longer than about 1000 bases, investigators must subclone the DNA into small fragments and sequence these small fragments. The procedures for doing this in a logical way are very labor intensive, cannot be automated, and are therefore impractical. The most popular technique for large-scale sequencing, the "shotgun" method, involves cloning and sequencing of hundreds or thousands of overlapping DNA fragments. Many of these methods are automated, but require sequencing 5–10 times as many bases as minimally necessary, leave gaps in the sequence information that must be filled in manually, and have difficulty determining sequences with repetitive DNA.

Thus, the goal of placing rapid sequencing techniques and improved mapping techniques in the hands of many researchers is yet to be achieved. New approaches are needed that eliminate the above-described limitations.

SUMMARY OF THE INVENTION

The present invention overcomes these and other drawbacks inherent in the prior art by providing methods and compositions for the analysis of nucleic acids, in particular for sequencing and mapping nucleic acids using double-stranded strand replacement reactions. These methods result in accurate sequencing reactions, in certain aspects due to very short extension reactions, and thus produce more useful sequence data from large templates, which overcome the problems inherent in single-stranded sequencing techniques. The present invention also provides new and powerful techniques for analyzing telomere length, telomere and subtelomeric sequence information, and quantitating the length and number of single-stranded overhangs present in telomeres.

First provided are methods of creating or selecting one or more nucleic acid products that terminate with at least a first selected base. These terminated nucleic acid products and populations thereof may be used in a wide variety of embodiments, including, but not limited to, nucleic acid sequencing, nucleic acid mapping, and telomere analysis.

The methods of creating one or more nucleic acid products that terminate with at least a first selected base generally comprise contacting at least a first substantially double stranded nucleic acid template comprising at least a first break on at least one strand with at least a first effective polymerase and a terminating composition comprising at least a first terminating nucleotide, the base of which corresponds to the selected base, under conditions effective to produce a nucleic acid product terminated at the selected base.

The methods may first involve the synthesis, construction, creation or generation of the substantially double stranded nucleic acid template that comprises at least a first break on at least one strand. In which case, "contacting" the template with the effective polymerase and terminating composition forms the second part of the method.

The term "template," as used herein, refers to a nucleic acid that is to be acted upon, generally nucleic acid that is to be contacted or admixed with at least a first effective polymerase and at least a first nucleotide substrate composition under conditions effective to allow the incorporation of at least one more nucleotide or base into the nucleic acid to form a nucleic acid product. In many embodiments of the present invention, the nucleic acid product generated is a nucleic acid product that terminates with at least a first selected base. In some cases "template" means the target nucleic acids intended to be separated or sorted out from other nucleic acid sequences within a mixed population.

"Substantially or essentially double stranded" nucleic acids or nucleic acid templates, as used herein, are generally nucleic acids that are double-stranded except for a proportionately small area or length of their overall sequence or length. The "proportionately small area" is an area lacking double stranded sequence integrity. The "proportionately small area lacking double stranded sequence integrity" may be as small as a single broken bond in only one strand of the nucleic acid, i.e., a break or "nick" within the double stranded nucleic acid molecule.

The "proportionately small area lacking double stranded sequence integrity" may also be a gap produced within the double stranded nucleic acid molecule by excision or removal of at least one base or nucleotide. In these cases, the "substantially double stranded nucleic acids" may be described as being double-stranded except for a proportionately small area of single-stranded nucleic acid. "Proportionately small areas of single-stranded nucleic acids" are those corresponding to single-stranded areas, stretches or lengths of one, two, three, four, five, six, seven, eight, nine or about ten bases or nucleotides, as may be produced by creating a gap within the double stranded nucleic acid molecule by excision or removal of one, two, three, four, five, six, seven, eight, nine or about ten bases or nucleotides.

In certain aspects of the invention, larger "proportionately small areas of single-stranded nucleic acids" are preferred, for example those corresponding to single-stranded areas, stretches or lengths of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 100 bases or nucleotides, as may be produced by creating a gap within the double stranded nucleic acid molecule by excision or removal of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 100 bases or nucleotides. In particular embodiments, even larger gaps may be created.

The "proportionately small area of single-stranded nucleic acid" within a substantially double stranded nucleic acid may occur at any point within the substantially double stranded nucleic acid molecule or template, i.e., it may be terminal or integral. "Terminal portions of single-stranded nucleic acid" within a substantially double stranded nucleic acid are generally "overhangs". Such "overhangs" may be naturally occurring overhangs, such as the area defined at the ends of telomeric DNA. "Overhangs" may also be engineered, i.e., created by the hand of man, using one or more of the techniques described herein and known to those of skill in the art. "Integral portions of single-stranded nucleic acid" within substantially double stranded nucleic acids, as used herein, will generally be engineered by the hand of man, again using one or more of the techniques described herein and known to those of skill in the art.

The term "double stranded", as applied to nucleic acids and nucleic acid templates, is generally reserved for nucleic acids that are completely double-stranded and that have no break, gap or single-stranded region. This allows "substantially double stranded" to be generally reserved for broken, nicked and/or gapped substantially double stranded nucleic acids and templates and substantially double stranded nucleic acids and templates that comprise at least a first single-stranded nucleic acid overhang.

The templates for use in the invention may be in virtually any form, including covalently closed circular templates and linear templates. Both "native or natural" and "recombinant" nucleic acids and nucleic acid templates may be employed. "Recombinant nucleic acids", as used herein, are generally nucleic acids that are comprised of segments of nucleic acids joined together by means of molecular biological techniques, i.e., by the hand of man. Although the nucleic acids for use in the methods will generally have been subjected to at least some isolation, and are thus not free from mans' intervention, "native and natural" nucleic acids and nucleic acid templates are intended to mean nucleic acids that have undergone less molecular biological manipulation and more correspond to the genomic DNA or fractions or fragments thereof.

The templates may also be derived from any initial nucleic acid molecule, sample or source including, but not limited to, cloning vectors, viruses, plasmids cosmids, yeast artificial chromosomes (YACs), bacterial artificial chromosomes (BACs) and chromosomal and extrachromosomal nucleic acids isolated from eukaryotic organisms, including, but not limited to, yeast, Drosophila and mammals, including, but not limited to, mice, rabbits, sheep, rats, goats, cattle, pigs, and primates such as humans, chimpanzees and apes.

In certain embodiments, the template may be created by cleavage from a precursor nucleic acid molecule. This generally involves treatment of the precursor molecule with enzymes that specifically cleave the nucleic acid at specific locations. Examples of such enzymes include, but are not limited to, restriction endonucleases, intron-encoded endonucleases, and DNA-based cleavage methods, such as triplex and hybrid formation methods, that rely on the specific hybridization of a nucleic acid segment to localize a cleavage agent to a specific location in the nucleic acid molecule.

In other embodiments, the template may be created by amplifying the template from a precursor nucleic acid molecule or sample. The amplified templates generally include a region to be analyzed, i. e. sequenced, and can be relatively small, or quite large in various embodiments.

In general, "amplification" may be considered as a particular example of nucleic acid replication involving template specificity. Amplification may be contrasted with non-specific template replication, i.e., replication that is template-dependent but not dependent on a specific template. "Template specificity" is here distinguished from fidelity of replication, i.e., synthesis of the proper polynucleotide sequence, and nucleotide (ribo- or deoxyribo-) specificity. "Template specificity" is frequently described in terms of "target" specificity. Target sequences are "targets" in the sense that they are desired to be separated or sorted out from other nucleic acids. Amplification techniques have been designed primarily for this "sorting out".

Amplification reactions generally require an initial nucleic acid sample or template, appropriate primers, an amplification enzyme and amplification reagents, such as deoxyribonucleotide triphosphates, buffers, and the like. In the sense of this application, a template for amplification (or "an amplification template") refers to an initial nucleic acid sample or template, and does not refer to the "substantially double stranded nucleic acid template comprising at least a first break on at least one strand". Therefore, as used herein, "an amplification template" is a "pre-template".

As used herein, the terms "amplifiable and amplified nucleic acids" are used in reference to any nucleic acid that may be amplified, or that has been amplified, by any amplification method including, but not limited to, PCR™, LCR, and isothermal amplification methods. Thus, the "substantially double stranded nucleic acid templates that comprise at least a first break on at least one strand" may be amplified nucleic acids or amplified nucleic acid products as well as templates for the methods of the invention.

Widely used methods for amplifying nucleic acids are those that involve temperature cycling amplification, such as PCR™. Isothermal amplification methods such as strand displacement amplification are also routinely employed to amplify nucleic acids. All such amplification methods are appropriate to amplify "templates" for use in the invention from precursor nucleic acids or "pre-templates".

As used herein, the term "PCR™" ("polymerase chain reaction") generally refers to methods for increasing the concentration of a segment of a template sequence in a mixture of genomic DNA without cloning or purification, as described in U.S. Pat. Nos. 4,683,195 and 4,683,202, each incorporated herein by reference. The process generally comprises introducing at least two oligonucleotide primers to a DNA mixture containing the desired template sequence, followed by a sequence of "thermal cycling" in the presence of a suitable DNA polymerase. The two primers are complementary to their respective strands of the double stranded template sequence. To effect amplification, the mixture is denatured and the primers then annealed to their complementary sequences within the template molecule. Following annealing, the primers are extended with a polymerase so as to form a new pair of complementary strands.

In PCR, the steps of denaturation, primer annealing and polymerase extension are generally repeated many times, such that "denaturation, annealing and extension" constitute one "cycle". Thus, "thermal cycling" means the execution of numerous "cycles" to obtain a high concentration of an amplified segment of the desired template sequence. As the desired amplified segments of the template sequence become the predominant sequences in the mixture, in terms of concentration, they are said to be "PCR™ amplified".

As used herein, the terms "PCR™ product", "PCR™ fragment" and "amplification product" refer to the resultant mixture of compounds after two or more cycles of the PCR™ steps of denaturation, annealing and extension are complete. These terms encompass the case where there has been amplification of one or more segments of one or more target sequences. "PCR™ products and fragments" can naturally act as the broken, nicked or gapped substantially double stranded nucleic acid templates for use in the invention.

Once a suitable or desired nucleic acid precursor, pre-template or sample composition has been obtained, a wide variety of substantially double stranded nucleic acid templates may be created for use in the claimed methods. In certain embodiments, even double stranded nucleic acid templates may be generated that comprise at least a first break substantially at the same position on both strands of the template. The most evident utility of this aspect of the invention is in producing nucleic acid fragments of a manageable size for further analysis, wherein such fragmentation is required.

In certain of the preferred sequencing and mapping embodiments, the substantially double stranded nucleic acid template will comprise at least a first break on only one of the two strands. This is advantageous in that the product or products are generated from the same strand, leading to more direct and rapid analysis. In certain of the sequencing and mapping aspects of the invention, having the strand replacement start at a defined point on one strand is advantageous, particularly where analysis of the size of the products of the reaction, particularly the differential size of a population of products, is necessary.

However, in a most general sense, creating a break on only one strand operably means that only one break is present in the region or target region of the individual nucleic acid molecule being analyzed or utilized. The target region is defined as a region of sufficient length to yield useful information and yet to allow the required volume of data to be generated in relation to the original nucleic acid subjected to the analysis. Thus, breaks at a distant region of the same nucleic acid molecule, outside of the target region, or breaks in the same general target region of a population of nucleic acid molecules, can exist and yet the target will still be considered to contain a "functional break" on only one strand.

In any event, in most aspects of the invention, the presence of additional breaks or nicks is not a drawback, so long as a 3' hydroxyl group can be generated in the presence of a template strand that can support the incorporation of at least one complementary base. The presence of multiple breaks on both strands is either useful, as one can initiate synthesis at a plurality of points as only the "first-encountered" break forms the functional break for extension and/or termination, or non-functional, and thus irrelevant, in most aspects of the invention. For example, although synthesis products may be produced from breaks on both strands, utilizing the labeling techniques in conjunction with the isolation or immobilization techniques as disclosed herein products from only one strand and closest to the detectable label are detected in the final analysis step, thus eliminating the requirement for a break on only one strand in the most rigid sense.

In general, the complexity of the nicking or breaking reaction is directly correlated with the complexity of the labeling and/or isolation or immobilization procedures. In aspects wherein a nick or break is generated at a single position in a population of identical templates, only a single detectable label is required to analyze the products of the extending and/or terminating reaction. The presence of additional breaks or nicks is made most useful when employed with additional labels and/or the isolation of a subset of the nucleic acid products prior to analysis.

Although by no means limiting, in substantially double stranded nucleic acid templates that comprise at least a first integral break or gap on only one strand, it is convenient to identify the intact or "unbroken" strand as the "template strand", and the strand that comprises at least a first integral break or gap as the "non-template strand". In those methods of the invention that encompass sequencing, the template strand will generally act as the guideline for the incorporation of one or more complementary bases or nucleotides into the "non-template strand", which is herein defined as the "extension of the non-template strand".

The "extension" of the non-template strand may be an extension by a single base or nucleotide only, in which case the "extension" is inherently an "extension and termination". The single base or nucleotide incorporated into the non-template strand is thus a "terminating base or nucleotide". This allows the broken, nicked or gapped strand to also be referred to as "the terminated strand".

Alternatively, the "extension" of the non-template strand may be an extension by two, three or more, or a plurality of, bases or nucleotides, and/or an extension to create a population of extended non-template strands each including a different number of incorporated bases or nucleotides. In these cases, "termination" is not co-extensive with "extension", and termination may even be delayed until after the incorporation of a significant number of "extending" bases or nucleotides. Thus, the broken, nicked or gapped strand that formed the starting point for the two, three or multiple base extension may also be termed "the synthesized strand".

In contrast, in substantially double stranded nucleic acid templates that comprise a terminal single-stranded portion or "overhang", it may be more convenient to identify the single-stranded overhang portion as the template strand. This is essentially because the art uses an existing "hybridizable" nucleic acid portion as a "template", e.g., in the sense that a sufficiently complementary probe or primer can hybridize to the template.

As used herein, the term "probe" refers to an oligonucleotide, ie., a contiguous sequence of nucleotides, whether occurring naturally as in a purified restriction digest or produced synthetically, recombinantly or by PCR™ amplification, that is capable of hybridizing to a nucleic acid of interest or portion thereof. Although probes may be single-stranded or double-stranded, the hybridizing probe described above in reference to binding to a nucleic acid overhang will generally be single-stranded. Probes are often labeled with a detectable label or "reporter molecule" that is detectable in a detection system, including, but not limited to fluorescent, enzyme (e.g., ELISA), radioactive, and luminescent systems.

The term "primer", as used herein refers to an oligonucleotide, whether occurring naturally as in a purified restriction digest or produced synthetically, that is capable of acting as a point of initiation of nucleic acid synthesis when placed under conditions in which the synthesis of a primer extension product that is complementary to a nucleic acid strand of interest is induced, e.g., in the presence of nucleotides and an inducing agent such as DNA polymerase and at a suitable temperature and pH. A primer must be sufficiently long to prime the synthesis of extension products in the presence of the inducing agent. The exact length of an effective primer depends on factors such as temperature of extension, source of primer and the particular extension method. Primers are preferably single stranded for maximum efficiency in amplification (but may be double stranded if first treated to separate the strands before use in preparing extension products). Primers are often preferably oligodeoxyribonucleotides.

The invention further provides various methods for generating the substantially double stranded, broken nucleic acid templates. Certain of the template-generation methods are generic to the creation of various types of template sought. For example, methods are disclosed that are capable of creating substantially double stranded nucleic acid templates in which either only one or both of the template strands are broken. Equally, distinct methods are provided for creating substantially double stranded nucleic acid templates in which both template strands are broken versus those for creating substantially double stranded nucleic acid templates in which only one of the template strands is broken.

Enzymatic methods are provided that are universally applicable to creating substantially double stranded nucleic acid templates in which either only one or both of the template strands are broken. Such methods generally comprise creating the template by contacting a double-stranded or substantially double-stranded nucleic acid with a combined effective amount of at least a first and second breaking enzyme combination. A "combined effective amount of at least a first and second breaking enzyme combination" is a combined amount of at least a first and second enzyme effective to create a substantially double stranded nucleic acid template in which either only one or both of the template strands comprise at least a first break.

Examples of broadly effective "enzymatic breaking combinations" are uracil DNA glycosylase in combination with an effectively matched endonuclease, such as endonuclease IV or endonuclease V. In light of the present disclosure, those of ordinary skill in the art will understand that the use of a uracil DNA glycosylase-endonuclease combination is predicated on the prior incorporation of at least a first uracil base or residue into the nucleic acid molecule that is to form the template.

Accordingly, in certain embodiments, the invention provides for the creation of a template by generating a double-stranded or substantially double-stranded nucleic acid molecule comprising at least a first uracil base or residue and contacting the uracil-containing nucleic acid molecule with a combined effective amount of a first, uracil DNA glycosylase enzyme and a second, endonuclease IV enzyme or endonuclease V enzyme. The use of endonuclease V in the combination is generally preferred. A "combined effective amount of a first, uracil DNA glycosylase enzyme and a second, endonuclease IV or V enzyme" is a combined amount of the enzymes effective to create a substantially double stranded nucleic acid template comprising at least a first gap corresponding in position to the position of the at least a first uracil base or residue incorporated into the uracil-containing nucleic acid molecule.

The incorporation of at least a first uracil base or residue into a double-stranded or substantially double-stranded nucleic acid molecule is generally achieved by incorporation of a dUTP residue in the nucleic acid synthesis reaction. In certain aspects of the invention it is desired to incorporate a single uracil base or residue into a specific location near the 5' end of the nucleic acid template. In a general sense, this may be accomplished by methods comprising contacting a precursor molecule with at least a first and a second primer that amplify the template when used in conjunction with a polymerase chain reaction, wherein at least one of the first or second primers comprises at least a first uracil base, and conducting a polymerase chain reaction to create an amplified template containing a single uracil residue corresponding to the location of the uracil base in the uracil-containing primer. In certain aspects, both primers contain uracil, to produce an amplified template that contains a uracil residue near the 5' end of both strands. In other embodiments, dUTP will be used in the synthesis of the template strand, thus incorporating multiple uracil residues into the template.

Incorporation of at least a first uracil base or residue only into one of the strands of the nucleic acid molecule allows for the subsequent generation of a substantially double stranded nucleic acid template in which only one of the template strands is broken, whereas incorporation of at least a first uracil base or residue into each of the strands of the nucleic acid molecule allows for the subsequent generation of a substantially double stranded nucleic acid template in which both of the template strands are broken.

Certain chemical cleavage compositions are also appropriate for creating substantially double stranded nucleic acid templates in which either only one or both of the template strands are broken. Such methods generally comprise creating the template by contacting a double-stranded or substantially double-stranded nucleic acid with an effective amount of an appropriate chemically-based nucleic acid cleavage composition. An "effective amount of an appropriate chemically-based nucleic acid cleavage composition" is an amount of the composition effective to create a substantially double stranded nucleic acid template in which either only one or both of the template strands comprise at least a first break.

In yet further embodiments, substantially double stranded nucleic acid templates in which either only one or both of the template strands are broken may be created by contacting a substantially double-stranded nucleic acid with an effective amount of at least a first appropriate nuclease enzyme. An "effective amount of at least a first appropriate nuclease enzyme" is an amount of the nuclease enzyme effective to create a substantially double stranded nucleic acid template in which either only one or both of the template strands comprise at least a first break.

In different embodiments, the invention provides methods for making and using substantially double stranded nucleic acid templates in which the one or more breaks or gaps are either located at a specific point or points along the nucleic acid template, or in which the one or more breaks or gaps are located at a random location or locations along the nucleic acid template. These may be referred to as "specifically broken, nicked or gapped templates" and "randomly broken, nicked or gapped templates", respectively. The methods for generating the specifically and randomly manipulated templates are generally different in principle and execution, although both nucleases and non-nuclease-based chemical or biological components may be used in various of the methods.

In certain embodiments, a substantially double stranded nucleic acid template comprising at least a first break or gap at a specific point on at least one strand of the template is created by contacting a double stranded or substantially double-stranded nucleic acid with an effective amount of at least a first specific nuclease enzyme. Exemplary specific nuclease enzymes are fl endonuclease, fd endonuclease or a restriction endonuclease. A preferred specific nuclease enzyme is fl endonuclease. An "effective amount of at least a first specific nuclease enzyme" is an amount of the nuclease enzyme effective to create a substantially double stranded nucleic acid template that comprises at least a first break or gap at a specific point on at least one strand of the template.

In other embodiments, the specific-type template is created by contacting a double-stranded or substantially double-stranded nucleic acid with an effective amount of an appropriate specific chemical cleavage composition. An exemplary embodiment is wherein the specific chemical cleavage composition comprises a nucleic acid segment, such as a hybrid or triple helix forming composition, that is linked to a metal ion chelating agent. The chelating agent binds a metal ion, and in the presence of a peroxide and a reducing agent, produces a hydroxyl radical that can nick or break a nucleic acid. The specificity of the cleavage is provided from the nucleic acid segment, which only hybridizes to or forms a triple helix at a specific location in the nucleic acid molecule to be broken or nicked. In certain cases, the hydroxyl radicals produced can diffuse, and thus a small region is broken or nicked, producing a gap. An "effective amount of at least a first specific chemical cleavage or triple helix-forming composition" is an amount of the composition effective to create a substantially double stranded nucleic acid template that comprises at least a first break or gap at a specific point on at least one strand of the template.

For use in certain embodiments, particularly the random break incorporation and random break degradation sequencing embodiments, the creation of a substantially double stranded nucleic acid template comprising at least a first random break or gap on at least one strand will be preferred. Templates with one or more breaks or nicks located at one or more random points or locations along the nucleic acid template are termed "randomly nicked templates". Suitable processes for creating such randomly nicked templates, or populations thereof, are collectively termed "random nicking". "Random nicking" generally refers to a process or processes effective to generate a substantially double stranded nucleic acid template that comprises at least a first broken bond located at at least a first random position within the sugar-phosphate backbone of at least one of the two strands of the nucleic acid template. As used herein, a "randomly nicked template" is intended to mean "at least a randomly nicked template". This signifies that at least one randomly-located broken bond is present, which broken bond may form the starting point or "substrate" for further manipulations, e.g., to convert the nick into a gap.

A process of random nicking that creates at least a first randomly positioned broken bond in a strand of the template may then be extended to create a gap at that random point or position by excising at least the first base or nucleotide proximal to the broken bond. This then becomes a process of "random gapping" effective to prepare a "random gap template", or a population thereof, comprising one or more gaps of at least a nucleotide in length positioned randomly within the nucleic acid template.

In certain embodiments, particularly certain mapping and sequencing aspects, the creation of a substantially double stranded nucleic acid template comprising at least a first random break or gap on only one strand will be preferred. This is generally for ease of analysis of the information generated from a strand replacement reaction, but also has advantages as detailed above.

Suitable methods that may be adapted to create a substantially double stranded nucleic acid template comprising at least a first random break or gap on at least one, or only one, strand are provided herein. The optimization of the random nicking methods to mono-stranded or dual-stranded nicking is generally based upon the correlation between the breaking or nicking agent, enzyme, chemical or composition and the time and conditions used to produce the break or nick. Agents that produce a given break or nick under one set of conditions, can produce a completely different break under different conditions. For example, a breaking or nicking agent that produces a single break or nick under one reaction condition, can in certain embodiments produce a plurality of breaks or nicks under a second, distinct reaction condition. Thus, the double stranded nucleic acid template comprising at least a first random break or gap on at least one, or only one, strand that is produced depends not only on the breaking or nicking agent used, but the conditions used to conduct the breaking or nicking reaction.

In one embodiment, the at least randomly nicked template is created by generating a double-stranded or substantially double-stranded nucleic acid comprising at least a first randomly positioned exonuclease-resistant nucleotide, and contacting the nucleic acid with an effective amount of an exonuclease. Exemplary exonuclease-resistant nucleotides include, but are not limited to deoxyribonucleotide phosphorothioates and deoxyribonucleotide boranophosphates. The preferred effectively matched exonuclease is exonuclease III. In these embodiments, an "effective amount of an exonuclease" is an amount of the exonuclease effective to degrade the strand containing the exonuclease-resistant base to the position of the resistant base.

The incorporation of at least a first randomly positioned exonuclease-resistant nucleotide into a double-stranded or substantially double-stranded nucleic acid molecule is generally achieved by utilizing extendable deoxynucleotides comprising the exonuclease-resistant feature during the synthesis of the nucleic acid precursor or template. The amount of exonuclease-resistant incorporated into the nucleic acid template can be controlled by adjusting the ratio of the extendable deoxynucleotides with and without the exonuclease-resistant feature used in the synthesis reaction.

In alternate aspects of the present invention, the at least randomly nicked template is created by contacting a double-stranded or substantially double-stranded nucleic acid with an effective amount of at least a first randomly-nicking or -breaking nuclease enzyme. Exemplary randomly-breaking nuclease enzymes are deoxyribonuclease I and CviJI restriction endonuclease. An "effective amount of at least a first randomly-nicking or -breaking nuclease enzyme" is an amount of the nuclease enzyme effective to create a substantially double stranded nucleic acid template in which either only one or both of the template strands comprise at least a first randomly located broken bond within the template backbone.

In yet a further aspect of the invention, the at least randomly nicked template is created by contacting a double-stranded or substantially double-stranded nucleic acid with a combined effective amount of at least a first and second randomly-breaking nuclease enzyme combination. Exemplary randomly-breaking enzymes for use as the first or second nuclease enzymes are the frequent-cutting restriction endonucleases Tsp509I, MaeII, TaiI, AluI, CviJI, NlaIII, MspI, HpaII, BstUI, BfaI, DpnII, MboI, Sau3AI, DpnI, ChaI, HinPI, HhaI, HaeIII, Csp6I, RsaI, TaqI and MseI, which may be used in any combination.

A "combined effective amount of at least a first and second randomly-breaking nuclease enzyme combination or frequent-cutting restriction endonuclease combination" is a combined amount of the nuclease enzymes effective to create a substantially double stranded nucleic acid template in which either only one or both of the template strands comprise at least a first randomly located broken bond within the template backbone.

As used herein, the terms "nucleases", "restriction endonucleases" and "restriction enzymes" refer to enzymes, generally bacterial enzymes, that cut nucleic acids. Mostly, the enzymes cut nucleic acids at or near specific nucleotide sequences, but certain enzymes, such as DNAase I, produce essentially random cuts or breaks.

Further embodiments of randomly-nicked template creation rely on contacting a double-stranded or substantially double-stranded nucleic acid with an effective amount of a randomly-nicking or -breaking chemical cleavage composition.

Throughout the variety of randomly-nicking or -breaking chemical cleavage compositions that may be employed, an "effective amount" is an amount of the chemical cleavage composition effective to create a substantially double stranded nucleic acid template in which either only one or both of the template strands comprise at least a first randomly located broken bond within the template backbone.

In preferred embodiments, the random chemical cleavage compositions will comprise or react to produce a hydroxyl radical. Certain suitable randomly-breaking chemical cleavage compositions comprise a chelating agent, a metal ion, a reducing agent and a peroxide, as exemplified by compositions that comprise EDTA, an $Fe^{2+}$ ion, sodium ascorbate and hydrogen peroxide. In other embodiments, the randomly-breaking chemical cleavage composition comprises a compound, generally a dye, that produces a hydroxyl radical upon contact with a defined or specified wavelength(s) of light.

Randomly-nicked templates may also be created by effectively irradiating with gamma irradiation, i.e., by contacting a double-stranded or substantially double-stranded nucleic acid with an effective amount of gamma irradiation.

Effective application of one or more mechanical breaking processes may also be employed to create the randomly broken or nicked templates. Exemplary mechanical breaking processes include subjecting double-stranded or substantially double-stranded nucleic acids to effective amounts of: hydrodynamic forces, sonication, nebulization and/or freezing and thawing.

In the methods of creating nucleic acid products that terminate with at least a first selected base, the at least nicked nucleic acid template is contacted with at least a first effective polymerase and at least a first effective terminating composition comprising at least a first terminating nucleotide, wherein the base of the terminating nucleotide corresponds to the selected base desired for nucleic acid incorporation and termination, "under conditions effective to produce a nucleic acid product terminated at the selected base".

"Under conditions effective to produce a nucleic acid product terminated at the selected base" means that the conditions are effective to permit at least one round of nucleotide extension and termination, thus incorporating at least one additional base or nucleotide (the selected base or corresponding nucleotide) into the nucleic acid product. The "effective conditions" are thus "product-generating conditions", "nucleotide extension and termination-permissive conditions" or "at least nucleotide extending and terminating conditions".

Fundamental aspects of the "effective, product-generating conditions" include conditions permissive or favorable to the necessary biological reactions, i.e., appropriate conditions of temperature, pH, ionic strength, and the like. The term "under conditions effective to produce a nucleic acid product terminated at the selected base" also means, in and of itself, "under conditions suitable and for a period of time effective to produce a nucleic acid product terminated at the selected base".

According to the intended use(s) of the selected base-terminated nucleic acid products, or populations thereof, the "effective, product-generating conditions and times" may also be termed "effective nucleic acid sequencing conditions" and/or "effective nucleic acid mapping conditions".

The "effective, product-generating conditions and times" will vary depending on the type of nucleic acid product or products that one wishes to generate: e.g., products in which the at least nicked nucleic acid template strand is extended with only a single base or nucleotide; or with only two selected bases or nucleotides; or with only three selected bases or nucleotides; or in which the at least nicked nucleic acid template strand is extended with a plurality of bases or nucleotides; and/or in which the at least nicked nucleic acid template is used to prime the synthesis of a population of extended nucleic acid strands, each terminated at a different point.

Inherent in the term "effective, product-generating conditions" is the concept that the "at least a first effective polymerase" will be a polymerase that is effective to generate the type of nucleic acid product or products desired under the extending or polymerizing conditions applied. Equally, the "at least a first effective terminating composition" will be a terminating composition effective to generate the type of terminated nucleic acid product or products desired under the termination conditions applied.

Also inherent in the term "effective, product-generating conditions" is the concept that the "effective polymerase" is a polymerase that is effective to act on the precise type of nick, break or gap in the template under the extending or polymerizing conditions applied. This means that the polymerase has synthetic activity under the chosen conditions, i.e., the polymerase is capable of catalyzing the addition of the desired type and number of bases or nucleotides using the nick, break or gap in the template as the "priming substrate". The type of nick, break or gap in the template thus forms an "effective matched pair" with the selected polymerase.

DNA molecules have "5' and 3' ends", meaning that mononucleotides have been reacted to make oligonucleotides or polynucleotides in a manner such that the 5' phosphate of one mononucleotide pentose ring is attached to the 3' oxygen (from the original hydroxyl) of its neighbor in one direction via a phosphodiester linkage. Therefore, an end of an oligonucleotide or polynucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring.

As used herein, a nucleic acid sequence, even if internal to a larger oligonucleotide or polynucleotide, may also be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand.

In embodiments where the break in the substantially double stranded nucleic acid template is a nick that comprises, or is reacted to comprise, a 3' hydroxyl group, the effective polymerase will generally either have 5' to 3' exonuclease activity or strand displacement activity, or both.

Effective polymerases in these categories include, for example, *E. coli* DNA polymerase I, Taq DNA polymerase, *S. pneumoniae* DNA polymerase I, Tfl DNA polymerase, *D. radiodurans* DNA polymerase I, Tth DNA polymerase, Tth XL DNA polymerase, *M. tuberculosis* DNA polymerase I, *M. thermoautotrophicum* DNA polymerase I, Herpes simplex-1 DNA polymerase, *E. coli* DNA polymerase I Klenow fragment, vent DNA polymerase, thermosequenase and wild-type or modified T7 DNA polymerases. In preferred embodiments, the effective polymerase will be *E. coli* DNA polymerase I, *M. tuberculosis* DNA polymerase I or Taq DNA polymerase.

Where the break in the substantially double stranded nucleic acid template is a gap of at least a base or nucleotide in length that comprises, or is reacted to comprise, a 3' hydroxyl group, the range of effective polymerases that may be used is even broader. In such aspects, the effective polymerase may be, for example, *E. coli* DNA polymerase I, Taq DNA polymerase, *S. pneumoniae* DNA polymerase I, Tfl DNA polymerase, *D. radiodurans* DNA polymerase I, Tth DNA polymerase, Tth XL DNA polymerase, *M. tuberculosis* DNA polymerase I, *M. thermoautotrophicum* DNA polymerase I, Herpes simplex-1 DNA polymerase, *E. coli* DNA polymerase I Klenow fragment, T4 DNA polymerase, vent DNA polymerase, thermosequenase or a wild-type or modified T7 DNA polymerase. In preferred aspects, the effective polymerase will be *E. coli* DNA polymerase I, *M. tuberculosis* DNA polymerase I, Taq DNA polymerase or T4 DNA polymerase.

In those embodiments in which either the nicked or broken template does not initially comprise a 3' hydroxyl group, such as when the template is generated by hydroxyl radicals (in certain instances) or certain physical or mechanical processes, the nicked template may still be manipulated or reacted to comprise the desired 3' hydroxyl group. Methods for achieving this generally involve "conditioning" the non-3' hydroxyl group containing position. In a preferred aspect of the invention, the "conditioning" involves exonuclease III treatment to remove the base or position lacking a 3' hydroxyl group, leaving a 3' hydroxyl group as a product of the removal reaction.

Various methods are also available for terminating the nucleic acid extension to produce the one or more terminated nucleic acid products. For example, the terminating composition may simply comprise a terminating dideoxynucleotide triphosphate, the base of which corresponds to the selected base. Extension with a single base and termination thus occur simultaneously as the dideoxynucleotide triphosphate in incorporated into the template at the break or nick, preventing further addition or extension due to the absence of an available —OH group.

In other embodiments, the terminating composition comprises a terminating deoxynucleotide triphosphate, the base of which corresponds to the selected base. Extension of the nicked strand with a single type of base and termination with that base still occur essentially simultaneously as only one type of deoxynucleotide triphosphate is available for incorporation into the template at the break or nick (with the number of bases incorporated into the nicked strand depending on the number of complementary bases in the corresponding or template strand), thus preventing further addition or extension due to the absence of other nucleotides.

Where detection of the nucleic acid product or products is desired, the product or products will preferably comprise a detectable label or isolation tag. Inherent in the term "under conditions effective to produce a nucleic acid product terminated at the selected base" is the concept that the "effective terminating composition" is effective to incorporate a detectable label into the nucleic acid product or products under the terminating conditions applied, should such labeling be necessary or preferable for subsequent detection or execution of related sequencing or mapping techniques. The type of terminating composition and the type of label or tag in the nucleic acid product or products thus also form an "effective matched pair".

Accordingly, in any of the methods of the invention, the at least a first terminating nucleotide or nucleotides may comprise a detectable label or an isolation tag that is incorporated into the nucleic acid product or products. In certain aspects, the substantially double stranded nucleic acid template may comprise a detectable label or isolation tag incorporated into the template, and hence into the subsequent nucleic acid product or products, at a point other than the termination point. In other aspects, both the template and the terminating nucleotide or nucleotides may each comprise a detectable label or an isolation tag.

Preferred aspects of the invention require the detection of the terminated nucleic acid product or products generated by the foregoing methods. In certain embodiments, the nucleic acid product or products will be separated, e.g., by electrophoresis, mass spectroscopy, FPLC or HPLC, prior to detection.

The nucleic acid product or products will generally comprise a detectable label, and the nucleic acid product or products are detected by detecting the label. In certain aspects, the nucleic acid product or products will comprises an isolation tag, and the nucleic acid product or products are purified using the isolation tag, optionally prior to more precise detection or differentiation techniques. Suitable detectable labels and isolation tags are exemplified by radioactive, enzymatic and fluorescent labels; and biotin, avidin and streptavidin isolation tags.

Detection is generally integral to the use of the invention in methods for sequencing nucleic acids, wherein the methods comprise detecting the nucleic acid product or products under conditions effective to determine the nucleic acid sequence of at least a portion of the nucleic acid.

In certain embodiments, the introduction or incorporation of the at least a first selected base at the break or nick in the template allows for direct nucleic acid sequencing. These methods generally rely on the generation of a population of nucleic acid products randomly terminated at four selected bases, as exemplified by:

a) creating a population of substantially double-stranded nucleic acid templates from a nucleic acid molecule to be sequenced, each of the templates comprising at least a first random break, preferably only on one strand;

b) contacting the population of templates with an effective polymerase and a terminating composition comprising four distinct labeled or tagged terminating nucleotides, under conditions effective to produce a population of terminated nucleic acid products randomly terminated at four selected bases;

c) detecting the population of randomly terminated nucleic acid products under conditions effective to determine the nucleic acid sequence of at least a portion of the original nucleic acid molecule.

In certain embodiments, the population of templates is contacted with the terminating composition in four distinct reactions, or wells, each of the reactions comprising only one of the four distinct labeled or tagged terminating nucleotides.

In other embodiments, the population of templates is contacted with the terminating composition in a single reaction, or well, wherein each of the four terminating nucleotides comprises a distinct, fluorescent label.

In further sequencing embodiments, the introduction or incorporation of the at least a first selected base at the break or nick in the template acts as a primer for other, non-direct nucleic acid sequencing methods. An exemplary method is "Sanger"-based sequencing, originating at the nick or gap in the double-stranded template. Such a method may comprise:

a) creating at least a first substantially double-stranded nucleic acid template from the nucleic acid molecule to be sequenced, the template comprising at least a first random break, preferably only on one strand;

b) contacting the at least a first template with an effective polymerase and at least a first extending and terminating composition comprising four extending deoxynucleotide triphosphates and a labeled or tagged terminating dideoxynucleotide triphosphate, under conditions effective to produce a population of terminated nucleic acid products, each originating from the random break;

c) detecting the terminated nucleic acid products under conditions effective to determine the nucleic acid sequence of at least a portion of the original nucleic acid molecule.

Again, the four terminating bases may comprise distinct fluorescent labels.

In addition to "Sanger-like" methods, still further analytical and sequencing methods also require the introduction or incorporation of at least one further base at the break or gap in the template in addition to the selected base. Thus, a first and a second selected base may be incorporated; or this may be described as incorporating a "specified base" in addition to the selected base. Production of a nucleic acid product comprising at least one specified base prior to termination at the selected base requires contacting the template with an effective polymerase and extending and terminating composition, wherein the extending composition comprises the extending specified base.

These methods may be further defined as methods for identifying a selected dinucleotide sequence in the template strand of the nucleic acid template, the dinucleotide sequence being the complement of the specified and selected base incorporated into the non-template, or synthesized strand that originally contained the nick or gap. Such methods comprise:

a) blocking the at least nicked template by contacting the at least nicked template with a first blocking composition comprising the three dideoxynucleotide triphosphates that do not contain the specified base, to create a blocked template;

b) removing the first blocking composition from contact with the blocked template;

c) contacting the blocked template with at least a first extending and terminating composition comprising an extending deoxynucleotide triphosphate containing the specified base, and a tagged or labeled terminating dideoxynucleotide triphosphate containing the selected base, under conditions effective to produce a nucleic acid product terminating with a dinucleotide sequence of the specified and selected base; and d) detecting the nucleic acid product under conditions effective to identify the selected dinucleotide sequence in the template strand of the nucleic acid template.

Defining the selected dinucleotide sequence as a first and second base in a template strand of a nucleic acid template, such methods are defined as comprising:

a) blocking the at least nicked template by contacting with a first blocking composition comprising three dideoxynucleotide triphosphates that do not contain the complement of the first base, to create a blocked template;

b) removing the first blocking composition from contact with the blocked template;

c) contacting the blocked template with at least a first extending and terminating composition comprising an extending deoxynucleotide triphosphate containing the complement of the first base, and a tagged or labeled terminating dideoxynucleotide triphosphate containing the complement of the second base, under conditions effective to produce a nucleic acid product terminating with a dinucleotide sequence complementary to the first and second base; and d) detecting the nucleic acid product under conditions effective to identify the selected dinucleotide sequence in the nucleic acid template.

In such methods, step (c) may be conducted as a single extending and terminating step, comprising contacting with a composition that comprises both the extending deoxynucleotide triphosphate and the terminating dideoxynucleotide triphosphate.

Step (c) may also be conducted as at least two distinct extending and terminating steps, comprising first contacting the template with an extending composition that comprises the extending deoxynucleotide triphosphate, and then contacting the template with a distinct terminating composition that comprises the terminating dideoxynucleotide triphosphate. Step (c) may comprise, in sequence, contacting the template with an extending composition that comprises the extending deoxynucleotide triphosphate, removing the extending composition from contact with the template, and contacting the template with a distinct terminating composition that comprises the terminating dideoxynucleotide triphosphate.

The non-Sanger analytical and sequencing methods may also require the introduction or incorporation of at least two further bases at the break or gap in the template in addition to the selected base. Thus, the nicked template is subjecting to a series of blocking and washing, and extending and washing reactions prior to contact with the terminating composition, thereby producing an extended nucleic acid product comprising two, three or a series of additional bases preceding the selected, terminating base.

Such methods allow for the identification of a selected trinucleotide sequence in a nucleic acid template, the trinucleotide sequence being the complement of the first and second specified bases and the selected base, the method comprising:

a) blocking the at least nicked template by contacting with a first blocking composition comprising three dideoxynucleotide triphosphates that do not contain the first specified base, to create a first-blocked template;

b) removing the first blocking composition from contact with the first-blocked template;

c) extending the first-blocked template by contacting with a first extending composition comprising an extending deoxynucleotide triphosphate containing the first specified base, to create a first-extended template;

d) removing the first extending composition from contact with the first-extended template;

e) blocking the first-extended template by contacting with a second blocking composition comprising three dideoxynucleotide triphosphates that do not contain the second specified base to create a second-blocked template;

f) removing the second blocking composition from contact with the second-blocked template;

g) contacting the second-blocked template with at least a first extending and terminating composition comprising an extending deoxynucleotide triphosphate containing the second specified base, and a tagged or labeled terminating dideoxynucleotide triphosphate containing the selected base, under conditions effective to produce a nucleic acid product terminating with a trinucleotide sequence of the first and second specified bases and the selected base; and h) detecting the nucleic acid product under conditions effective to identify a selected trinucleotide sequence in the nucleic acid sample.

Defining the selected trinucleotide sequence as a first, second and third base in a template strand of a nucleic acid template, the foregoing methods are defined as comprising:

a) blocking the at least nicked template by contacting with a first blocking composition comprising three dideoxynucleotide triphosphates that do not contain the complement of the first base to create a first-blocked template;

b) removing the first blocking composition from contact with the first-blocked template;

c) extending the first-blocked template by contacting with a first extending composition comprising an extending deoxynucleotide triphosphate containing the complement of the first base to create a first-extended template;

d) removing the first extending composition from contact with the first-extended template;

e) blocking the first-extended template by contacting with a second blocking composition comprising three dideoxynucleotide triphosphates that do not contain the complement of the second base to create a second-blocked template;

f) removing the second blocking composition from contact with the second-blocked template;

g) contacting the second-blocked template with at least a first extending and terminating composition comprising an extending deoxynucleotide triphosphate containing the complement of the second base, and a tagged or labeled terminating dideoxynucleotide triphosphate containing the complement of the third base, under conditions effective to produce a nucleic acid product terminating with a trinucleotide sequence complementary to the first, second and third bases; and h) detecting the nucleic acid product under conditions effective to identify the selected trinucleotide sequence in the nucleic acid sample.

These methods may comprise:

a) blocking the at least nicked template by contacting with a first blocking composition comprising three dideoxynucleotide triphosphates that do not contain the complement of the first base to create a first-blocked template;

b) removing the first blocking composition from contact with the first-blocked template;

c) extending the first-blocked template by contacting with a first extending composition comprising an extending deoxynucleotide triphosphate containing the complement of the first base to create a first-extended template;

d) removing the first extending composition from contact with the first-extended template;

e) blocking the first-extended template by contacting with a second blocking composition comprising three dideoxynucleotide triphosphates that do not contain the complement of the second base to create a second-blocked template;

f) removing the second blocking composition from contact with the second-blocked template;

g) further extending the second-blocked template by contacting with a second extending composition comprising an extending deoxynucleotide triphosphate containing the complement of the second base to create a second-extended template;

h) terminating the reaction by contacting the second-extended template with a terminating composition comprising a tagged or labeled terminating dideoxynucleotide triphosphate containing the complement of the third base, under conditions effective to produce a nucleic acid product terminating with a trinucleotide sequence complementary to the first, second and third bases; and i) detecting the nucleic acid product under conditions effective to identify a selected trinucleotide sequence in the nucleic acid sample.

The methods of di- and tri-nucleotide identification may further be used as methods for sequencing a nucleic acid molecule by identifying selected di- or tri-nucleotide sequences, wherein the identification of the selected di- or tri-nucleotide sequences is followed by the compilation of the identified di- or tri-nucleotide sequences to determine the contiguous nucleic acid sequence of at least a portion of the nucleic acid molecule.

The methods of selecting at least a first nucleic acid product terminated with at least a first selected base generally comprise creating a substantially double stranded nucleic acid template comprising at least a first break on at least one strand, and contacting the template with an effective polymerase and a terminating composition comprising at least a first terminating nucleotide, wherein the base of the terminating nucleotide corresponding to the selected base, under conditions effective to produce a nucleic acid product terminated at a selected base, or an effective polymerase and an extending composition under conditions effective to produce a fully extended product only from a template that terminates at the selected base. The methods may first involve creating a substantially double stranded nucleic acid template comprising at least a first random double stranded break.

The methods may be further defined as methods for determining the position of at least a first selected dinucleotide sequence of at least a first and at least a second base in at least a first nucleic acid template. The methods may comprise:

a) ligating a double-stranded nucleic acid segment to the double-stranded break, the double-stranded nucleic acid segment comprising an upper strand comprising a 5' end comprising a phosphate group and a blocked 3' end and a lower strand comprising a blocked 5' end and a 3' end comprising a hydroxyl group;

b) blocking the template by contacting with a first blocking composition comprising three dideoxynucleotide triphosphates that do not contain the complement of the first base;

c) removing the first blocking composition from contact with the template;

d) extending the template by contacting with a first extending composition comprising an extending deoxynucleotide triphosphate containing the complement of the first base;

e) removing the first extending composition from contact with the template;

f) blocking the template by contacting with a second blocking composition comprising three dideoxynucleotide triphosphates that do not contain the complement of the second base;

g) removing the second blocking composition from contact with the template;

h) contacting the template with at least a second extending composition comprising four extending deoxynucleotide triphosphates, at least one of the extending deoxynucleotide triphosphates containing a tagged or labeled base, under conditions effective to produce a fully extended tagged or labeled nucleic acid product with a dinucleotide sequence complementary to the first and second bases; and i) detecting the nucleic acid product under conditions effective to determine the position of the selected dinucleotide sequence in the nucleic acid sample.

The methods of determining the position of at least a first selected dinucleotide sequence comprising at least a first base and a second base in one or more nucleic acid templates may alternatively comprise:

a) attaching a double-stranded nucleic acid segment to the double-stranded break, the double-stranded nucleic acid segment comprising an upper strand comprising a 5' end comprising a phosphate group and a blocked 3' end and a lower strand comprising a blocked 5' end and a blocked 3' end;

b) heating the template at a temperature effective to disassociate the lower strand of the adaptor;

c) annealing a single-stranded oligonucleotide comprising a 3' hydroxyl group to the template, the first oligonucleotide comprising the same nucleotide sequence as the lower strand plus a first additional 3' base complementary to the first base and a second additional 3' base complementary to the second base;

d) contacting the template with an extending composition comprising four extending deoxynucleotide triphosphates, at least one of the extending deoxynucleotide triphosphates containing a tagged or labeled base, under conditions effective to produce a fully extended tagged or labeled nucleic acid product with a dinucleotide sequence complementary to the first and second bases; and e) detecting the nucleic acid product under conditions effective to determine the position of the selected dinucleotide sequence in the nucleic acid sample.

Optionally, the methods of determining the position of at least a first selected dinucleotide sequence comprising at least a first base and a second base in at least a first nucleic acid template may comprise:

a) ligating a double-stranded nucleic acid segment to the double-stranded break, the double-stranded nucleic acid segment comprising an upper strand comprising a 5' end comprising a phosphate group and a blocked 3' end and a lower strand comprising a blocked 5' end and a blocked 3' end;

b) heating the ligated double-stranded nucleic acid segment at a temperature effective to disassociate the lower strand of the adaptor;

c) annealing a first single-stranded oligonucleotide comprising a 3' hydroxyl group to the templates, the first oligonucleotide comprising the same nucleotide sequence as the lower strand;

d) blocking the templates by contacting with a first blocking composition comprising a dideoxynucleotide triphosphate that contains the complement of the first base;

e) removing the first blocking composition from contact with the templates;

f) contacting the templates with at least a first extending composition comprising four deoxynucleotide triphosphates, one of the deoxynucleotide triphosphates comprising a uracil base, under conditions effective to completely extend the non-template strand;

g) heating the templates at a temperature effective to disassociate the first single stranded oligonucleotide;

h) annealing a second single-stranded oligonucleotide comprising a 3' hydroxyl group to the templates, the second oligonucleotide comprising the same nucleotide sequence as the first single-stranded oligonucleotide plus a first additional 3' base complementary to the first base;

i) blocking the templates by contacting with a second blocking composition comprising a dideoxynucleotide triphosphate that contains the complement of the second base;

j) removing the second blocking composition from contact with the templates;

k) contacting the templates with the at least a first extending composition comprising four deoxynucleotide triphosphates, one of the deoxynucleotide triphosphates comprising a uracil base, under conditions effective to completely extend the non-template strand;

l) heating the templates at a temperature effective to disassociate the second single stranded oligonucleotide;

m) annealing a third single-stranded oligonucleotide comprising a 3' hydroxyl group to the templates, the second oligonucleotide comprising the same nucleotide sequence as the second single-stranded oligonucleotide plus a second additional 3' base complementary to the second base;

n) contacting the templates with at least a second extending and labeling composition comprising four deoxynucleotide triphosphates, at least one of which comprises a detectable label, under conditions effective to completely extend the non-template strand;

o) contacting the templates with at least a first degrading composition under conditions effective to degrade the non-template strands containing a uracil base; and p) detecting the nucleic acid products under conditions effective to determine the position of the selected dinucleotide sequence in the nucleic acid templates.

The methods may also be further defined as methods for determining the position of at least a first selected trinucleotide sequence of at least a first, second and third base in one or more nucleic acid templates. The methods may comprise:

a) ligating a double-stranded nucleic acid segment to the double-stranded break, the double-stranded nucleic acid segment comprising an upper strand comprising a 5' end comprising a phosphate group and a blocked 3' end and a lower strand comprising a blocked 5' end and a 3' end comprising a hydroxyl group;

b) blocking the template by contacting with a first blocking composition comprising three dideoxynucleotide triphosphates that do not contain the complement of the first base;

c) removing the first blocking composition from contact with the template;

d) extending the template by contacting with a first extending composition comprising an extending deoxynucleotide triphosphate containing the complement of the first base;

e) removing the first extending composition from contact with the template;

f) blocking the template by contacting with a second blocking composition comprising three dideoxynucleotide triphosphates that do not contain the complement of the second base;

g) removing the second blocking composition from contact with the template;

h) extending the template by contacting with a second extending composition comprising an extending deoxynucleotide triphosphate containing the complement of the second base;

i) removing the second extending composition from contact with the template;

j) blocking the template by contacting with a third blocking composition comprising three dideoxynucleotide triphosphates that do not contain the complement of the third base;

k) removing the third blocking composition from contact with the template;

l) contacting the template with at least a third extending composition comprising four extending deoxynucleotide triphosphates, at least one of the extending deoxynucleotide triphosphates containing a tagged or labeled base, under conditions effective to produce a fully extended tagged or labeled nucleic acid product with a trinucleotide sequence complementary to the first, second and third bases; and m) detecting the nucleic acid product under conditions effective to determine the position of the selected dinucleotide sequence in the nucleic acid sample.

The methods of determining the position of at least a first selected trinucleotide sequence comprising at least a first base, a second base and a third base in at least a first nucleic acid template may optionally comprise:

a) attaching a double-stranded nucleic acid segment to the double-stranded break, the double-stranded nucleic acid segment comprising an upper strand comprising a 5' end comprising a phosphate group and a blocked 3' end and a lower strand comprising a blocked 5' end and a blocked 3' end;

b) heating the template at a temperature effective to disassociate the lower strand of the adaptor;

c) annealing a single-stranded oligonucleotide comprising a 3' hydroxyl group to the template, the first oligonucleotide comprising the same nucleotide sequence as the lower strand plus a first additional 3' base complementary to the first base, a second additional 3' base complementary to the second base and a third additional 3' base complementary to the third base;

d) contacting the template with an extending composition comprising four extending deoxynucleotide triphosphates, at least one of the extending deoxynucleotide triphosphates containing a tagged or labeled base, under conditions effective to produce a fully extended tagged or labeled nucleic acid product with a trinucleotide sequence complementary to the first, second and third bases; and e) detecting the nucleic acid product under conditions effective to determine the position of the selected trinucleotide sequence in the nucleic acid sample.

Alternatively, the methods of determining the position of at least a first selected trinucleotide sequence comprising at least a first base, a second base and a third base in one or more nucleic acid templates may comprise:

a) ligating a double-stranded nucleic acid segment to the double-stranded break, the double-stranded nucleic acid segment comprising an upper strand comprising a 5' end comprising a phosphate group and a blocked 3' end and a lower strand comprising a blocked 5' end and a blocked 3' end;

b) heating the ligated double-stranded nucleic acid segment at a temperature effective to disassociate the lower strand of the adaptor;

c) annealing a first single-stranded oligonucleotide comprising a 3' hydroxyl group to the templates, the first oligonucleotide comprising the same nucleotide sequence as the lower strand;

d) blocking the templates by contacting with a first blocking composition comprising a dideoxynucleotide triphosphate that contains the complement of the first base;

e) removing the first blocking composition from contact with the templates;

f) contacting the templates with at least a first extending composition comprising four deoxynucleotide triphosphates, one of the deoxynucleotide triphosphates comprising a uracil base, under conditions effective to completely extend the non-template strand;

g) heating the templates at a temperature effective to disassociate the first single stranded oligonucleotide;

h) annealing a second single-stranded oligonucleotide comprising a 3' hydroxyl group to the templates, the second oligonucleotide comprising the same nucleotide sequence as the first single-stranded oligonucleotide plus a first additional 3' base complementary to the first base;

i) blocking the templates by contacting with a second blocking composition comprising a dideoxynucleotide triphosphate that contains the complement of the second base;

j) removing the second blocking composition from contact with the templates;

k) contacting the templates with the at least a first extending composition comprising four deoxynucleotide triphosphates, one of the deoxynucleotide triphosphates comprising a uracil base, under conditions effective to completely extend the non-template strand;

l) heating the templates at a temperature effective to disassociate the second single stranded oligonucleotide;

m) annealing a third single-stranded oligonucleotide comprising a 3' hydroxyl group to the templates, the second oligonucleotide comprising the same nucleotide sequence as the second single-stranded oligonucleotide plus a second additional 3' base complementary to the second base;

n) contacting the templates with the at least a second extending composition comprising four deoxynucleotide triphosphates, one of the deoxynucleotide triphosphates comprising a uracil base, under conditions effective to completely extend the non-template strand;

o) heating the templates at a temperature effective to disassociate the third single stranded oligonucleotide;

p) annealing a fourth single-stranded oligonucleotide comprising a 3' hydroxyl group to the templates, the second oligonucleotide comprising the same nucleotide sequence as the third single-stranded oligonucleotide plus a third additional 3' base complementary to the third base;

q) contacting the templates with at least a third extending and labeling composition comprising four deoxynucleotide triphosphates, at least one of which comprises a detectable label, under conditions effective to completely extend the non-template strand;

r) contacting the templates with at least a first degrading composition under conditions effective to degrade the non-template strands containing a uracil base; and s) detecting the nucleic acid products under conditions effective to determine the position of the selected trinucleotide sequence in the nucleic acid templates.

Further methods of the present invention are methods of sequencing a nucleic acid molecule by identifying a selected dinucleotide sequence comprising a first base and a second base, the methods comprising:

a) creating a substantially double-stranded nucleic acid template comprising a selected dinucleotide sequence on a template strand and comprising an exonuclease-resistant nucleotide in the non-template strand, wherein the base of the exonuclease-resistant nucleotide is complementary to the first base;

b) contacting the template with an amount of an exonuclease effective to degrade the non-template strand until the position of the exonuclease-resistant nucleotide;

c) removing the exonuclease from contact with the template;

d) contacting the template with at least a first terminating composition comprising a tagged or labeled terminating dideoxynucleotide triphosphate containing the complement of the second base, under conditions effective to produce a nucleic acid product terminating with a dinucleotide sequence complementary to the first and second base; and e) detecting the nucleic acid product under conditions effective to identify the selected dinucleotide sequence in the template strand of the nucleic acid template.

Detection of a selectively-terminated nucleic acid product or products is also generally integral to the use of the invention in methods for mapping a nucleic acid, wherein the methods generally comprise detecting the nucleic acid product or products under conditions effective to determine the position of the nucleic acid relative to the nucleic acid product or products. The mapping methods may comprise:

a) creating a population of substantially double-stranded nucleic acid templates from the nucleic acid, the templates comprising at least a first random break on at least one strand or at least a first random break on only one strand;

b) contacting the population of templates with an effective polymerase and at least a first degradable extension-producing composition comprising three non-degradable extending nucleotides (deoxynucleotides) and one degradable nucleotide, under conditions and for a time effective to produce a population of degradable nucleic acid products comprising the degradable nucleotide;

c) removing the degradable extension-producing composition from contact with the templates;

d) contacting the population of degradable nucleic acid products with an effective polymerase and at least a first nondegradable extending and terminating composition comprising four non-degradable extending deoxynucleotides, at least one of the non-degradable extending deoxynucleotides comprising a detectable label or an isolation tag, under conditions and for a time effective to produce a population of terminated nucleic acid products comprising a degradable region and a nondegradable region;

e) contacting the population of terminated nucleic acid products with an effective amount of a degrading composition to degrade the degradable region, thereby producing nested nucleic acid products; and f) detecting the nested nucleic acid products under conditions effective to determine the position of the nucleic acid relative to the nucleic acid product.

As used herein, the term "nested nucleic acid products" means a series of nucleic acid products that are a different distance from the point that the nucleic acid synthesis originates. In certain aspects, the products will be overlapping nucleic acid products, but this is not a requirements for most of the embodiments of the present invention.

In preferred embodiments, the degradable nucleotide will be a uracil base-containing nucleotide and the degrading composition will comprise a combined effective amount of a uracil DNA glycosylase enzyme and an endonuclease IV or an endonuclease V enzyme.

The present invention still further provides methods of sequencing through a telomeric repeat region into a subtelomeric region, comprising:

a) providing a substantially double-stranded nucleic acid that comprises, in contiguous sequence order, a terminal single-stranded telomeric overhang, a double-stranded telomeric repeat region and a double-stranded subtelomeric region;

b) contacting the nucleic acid with a composition comprising an oligonucleotide or primer that is substantially complementary to and hybridizes to the single-stranded telomeric overhang, an effective polymerase, four extending nucleotides and at least a first tagged or labeled terminating nucleotide under conditions effective to produce a nucleic acid product extended from the primer into the subtelomeric region; and c) detecting the nucleic acid product under conditions effective to determine the nucleic acid sequence of the telomeric overhang, the telomeric repeat region and at least a portion of the subtelomeric region.

The present invention also provides a method for determining the percentage of telomeres in a population that contain 3' overhangs, comprising:

a) contacting a telomere-containing nucleic acid sample suspected of having telomeres containing a first, 3' overhang-containing strand and a second, non-overhang strand, with a composition comprising an oligonucleotide or primer that is substantially complementary to and hybridizes to the single-stranded telomeric overhang, an effective polymerase and four extending nucleotides under conditions effective to produce a nucleic acid product extended from the primer and a trimmed second, non-overhang strand, wherein a telomere that does not have a 3' overhang will comprise a non-trimmed second, non-overhang strand; and b) detecting the nucleic acid product under conditions effective to determine the amounts of the nucleic acid product, the trimmed second, non-overhang strand, the first, 3' overhang-containing strand and the non-trimmed second, non-overhang strand.

In particular aspects, the amounts of the nucleic acid product, the trimmed second, non-overhang strand, the first, 3' overhang-containing strand and the non-trimmed second, non-overhang strand are determined by hybridization with labeled G-rich and C-rich telomeric sequences or segments.

The term "oligonucleotide", as used herein, defines a molecule comprised of two or more deoxyribonucleotides or ribonucleotides, usually more than three (3), and typically more than ten (10) and up to one hundred (100) or more. Preferably, "oligos" comprise between about fifteen or twenty and about thirty deoxyribonucleotides or ribonucleotides. Oligonucleotides may be generated in any effective manner, including chemical synthesis, DNA replication, reverse transcription, or a combination thereof.

A primer is said to be "substantially" complementary to a strand of specific sequence of a template where it is sufficiently complementary to hybridize to the template sufficient for primer elongation to occur. A primer sequence need not reflect the exact sequence of a template. For example, a non-complementary nucleotide fragment may be attached to the 5' end of a primer, with the remainder of the primer sequence being substantially complementary to a template. Non-complementary bases or longer sequences can be interspersed into a primer, provided that the primer sequence has sufficient complementarity with the sequence of the template to hybridize and thereby form a template primer complex for synthesis of the extension product of the primer.

"Hybridization" methods involve the annealing of a complementary or sufficiently complementary sequence to a target nucleic acid sequence. The ability of two polymers of nucleic acid containing complementary sequences to anneal through base pairing interaction is a well-recognized phenomenon (Marmur and Lane, 1960; Doty et al., 1960).

The "complement" of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Stability of a nucleic acid duplex is measured by the melting temperature, or "$T_m$." The $T_m$ of a particular nucleic acid duplex under specified conditions is the temperature at which on average half of the base pairs have disassociated. The equation for calculating the $T_m$ of nucleic acids is well known in the art. As indicated by standard references, an estimate of the $T_m$ value may be calculated by the equation:

$$T_m = 81.5° C. + 16.6 \log M + 0.41(\% GC) - 0.61(\% \text{form}) - 500/L$$

where M is the molarity of monovalent cations, %GC is the percentage of guanosine and cytosine nucleotides in the DNA, % form is the percentage of formamide in the hybridization solution, and L=length of the hybrid in base pairs (Berger and Kimmel, 1987). More sophisticated computations are also known in the art that take structural as well as sequence characteristics into account for the calculation of $T_m$.

The invention yet further provides methods of determining the length of a single-stranded overhang of a telomere, comprising contacting a telomere comprising a single-stranded overhang with an excess of a primer that hybridizes to the single-stranded overhang under conditions effective to allow hybridization of substantially complementary nucleic acids, and quantitating the primers thus hybridized to the single-stranded overhang. These methods may further comprise contacting the primers hybridized to the single-stranded overhang with a ligation composition in an amount and for a time effective to ligate the primers, wherein the length of the ligated primers is quantitated.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4A shows the DNA segment to be sequenced (double headed arrow) and the fl origin of replication site used to produce the single-stranded nick. FIG. 4B shows the DNA after the nick has been introduced by fl endonuclease. FIG. 4C shows the initiation of the strand replacement reaction (bold line). FIG. 4D shows the extension of the strand replacement reaction (bold line). FIG. 4E shows the termination of the strand replacement reaction (closed circle) on one DNA molecule. FIG. 4F shows a population of DNA molecules with strand replacement reactions (bold line), terminated at different locations (closed circles). FIG. 4G shows the population of DNA molecules with strand replacement reactions (bold line), terminated at different locations (closed circles) from FIG. 4F, with the location of restriction endonuclease sites X and Y indicated. Cleavage with restriction enzyme X produces the fragments 1, 2 and 3, while cleavage with the restriction enzyme Y produces the fragments 4 and 5. FIG. 4H shows the products of the restriction endonuclease digests X and Y on the DNA. FIG. 4I shows the strand replacement reactions (bold lines) terminated at different positions (closed circles) on fragment 4 produced from a restriction digest of the population of molecules shown in FIG. 4G. The labeled strand replacement strands are denatured, and run on a sequencing gel to determine the sequence.

FIG. 7A. In this method, one of the PCR™ primers has an fl endonuclease recognition site incorporated into the sequence, while the second PCR™ primer does not. Treatment of the PCR™ product with fl endonuclease produces a nick at the fl recognition site. The nick can be used to initiate a double-stranded sequencing reaction. FIG. 7B. In this embodiment, one of the strands of the PCR™ product has a phosphorothioate linkage incorporated into an EcoRV restriction endonuclease site. Treatment with EcoRV produces a nick in the strand opposite the phosphorothioate linkage, that can be utilized to prime a double-stranded sequencing reaction. FIG. 7C. In yet another embodiment, the PCR™ products can be subjected to treatments to degrade a few nucleotides from the 5' termini, for example by use of T7 gene 6 exonuclease. Subsequent hybridization of an oligonucleotide primer under non-denaturing conditions to the 3' tail of the PCR™ product will produce the priming site necessary for initiation of the double-stranded sequencing reaction. FIG. 7D. In this aspect of the invention, dUTP present in one of the PCR™ primers is degraded, and as shown in FIG. 7C hybridization of an oligonucleotide primer under non-denaturing conditions to the 3' tail of the PCR™ product produces a priming site that can be used to initiate a strand replacement reaction. FIG. 7E. In this embodiment, only one uracil base is incorporated into the PCR™ product through one of the PCR™ primers. The uracil base can be removed by uracil DNA glycosylase, and a nick created by subsequent treatment with heat, base, or an enzyme such as endonuclease IV or endonuclease V. The nick can be used to initiate a double-stranded sequencing reaction.

FIG. 10A shows the starting Sty11 plasmid construct, having an 800 bp telomere tract (vertical lines) flanked by EcoRI restriction sites, after restriction digest with ClaI. FIG. 10B shows the product of the reaction of the starting construct with Bal 31 nuclease and T7 gene 6 exonuclease, having a G-overhang in the telomere tract. FIG. 10C shows the hybridization of the TelC primers to the G-overhang region of the telomere tract. FIG. 10D shows the product of the extension reaction with Taq DNA polymerase and dATP, dCTP and dTTP. $C_S$ is the newly-synthesized extension products, $C_t$ is the trimmed original C-rich strands, and $C_o$ is the original G-rich strands and untrimmed C-rich strands. FIG. 10E shows the product of the extension reaction with Taq DNA polymerase and all four deoxynucleotides dATP, dCTP, dTTP and dGTP. $C_S$ is the newly-synthesized extension products, $C_t$ is the trimmed original C-rich strands, and $C_o$ is the original G-rich strands and untrimmed C-rich strands.

FIG. 14A. Sequencing reactions run in buffer A. FIG. 14B. Sequencing reactions run in buffer B.

FIG. 19. Schematically sets forth RBI with detectable ddNTP and biotinylated primer. The top panel shows a PCR™-amplified DNA immobilized at the 5' end of primer X (open circle). The numbers show the 12 unknown bases. The next panel shows the population of products of random degradation (nicks shown on upper strand only), with each of the twelve unknown bases being nicked. The next panel represents the products of the random degradation after exposing the 3' hydroxyl group at the damage site. The next panel shows the incorporation of tagged (labeled) ddTTP at positions opposite adenine in the template strand. The next panel shows the denaturation and removal of the non-immobilized strands. The bottom panel is a schematic representation of the mobilized, originally retained strands separated by electrophoresis, and detection of the tagged bases. The dark bars represent the position of thymine.

FIG. 21. Schematically sets forth double-base sequencing by RBI (example shown is a "T-walk" followed by "A-walk"). The PCR-amplification, immobilization, 3' hydroxyl group exposure at random sites is conducted as detailed in FIG. 19. The top panel shows the population of products of random degradation (nicks shown on upper strand only), with each of the twelve unknown bases being nicked. The next panel shows blocking of the positions opposite T, G and C with ddATP, ddCTP and cddGTP (shown in bold letters), followed by removal of the ddATP, ddCTP and ddGTP, and addition of dTTP, which has a 3' hydroxyl group that serves as an initiation site for further nucleotide addition. The next panel shows blocking of positions opposite A, G and C with ddTTP, ddCTP and ddGTP (shown in bold letters), followed by the removal of the ddTTP, ddCTP and ddGTP, and addition of tagged (labeled) ddATP. The next panel shows denaturation and removal of the non-immobilized strands. The bottom panel is a schematic representation of the mobilized, originally retained strands separated by electrophoresis, and detection of the tagged bases. The dark bars represent the position of thymine followed by adenine.

FIG. 23. Schematically sets forth an example of a three-base walk finding the position of the succession $T_aA_bT$. The PCR-amplification, immobilization, 3' hydroxyl group exposure at random sites is conducted as detailed in FIG. 19. The top panel shows the population of products of random degradation (nicks shown on upper strand only), with each of the twelve unknown bases being nicked. The next panel shows blocking of the positions opposite T, G and C with ddATP, ddCTP and ddGTP (shown in bold letters), followed by removal of the ddATP, ddCTP and ddGTP, and addition of dTTP, which has a 3' hydroxyl group that serves as an initiation site for further nucleotide addition. The next panel shows blocking of positions opposite A, G and C with ddTTP, ddCTP and ddGTP (shown in bold letters), followed by the removal of the ddTTP, ddCTP and ddGTP, and addition of dATP, which has a 3' hydroxyl group that serves as an initiation site for further nucleotide addition. The next panel shows blocking of the positions opposite T, G and C with ddATP, ddCTP and ddGTP (shown in bold letters), followed by removal of the ddATP, ddCTP and ddGTP, and addition of tagged (labeled) ddTTP. The bottom panel is a schematic representation of the denaturation and removal of the non-immobilized strands, the mobilization of the originally retained strands and separation by electrophoresis, and detection of the tagged terminal thymidine. The dark bar represents the position of thymine followed by adenine, followed by thymine.

FIG. 28A and FIG. 28B. pUC19 DNA samples after Fe/EDTA treatment, conditioning and DNA polymerase labeling run on 1% agarose gel. FIG. 28A. Ethidium bromide staining of the gel. FIG. 28B. Autoradiogram of the DNA. Lanes 1 and 7: non-conditioned Fe/EDTA treated DNA; lanes 2 and 8: DNA conditioned with T4 DNA polymerase only; lanes 3 and 9: DNA conditioned with combined action of T4 DNA polymerase and 0.1 U exo III; lanes 4 and 10: DNA conditioned with combined action of T4 DNA polymerase and 0.3 U exo III; lanes 5 and 11: DNA conditioned with combined action of T4 DNA polymerase and 1 U exo III; lanes 6 and 12: DNA conditioned with combined action of T4 DNA polymerase and 3 U exo III.

FIG. 30A. Structure of an exemplary 5' phosphorylated, 3'-blocked oligonucleotide adaptor as described in Example 10, used to create a randomly positioned nick or template sequence (top strand, W). Filled circle indicates 5' phosphate group, filled squares indicate blocked 3'-ends (dideoxynucleotide or $NH_2$ group). FIG. 30B. General structure of primers C-X, C-XY and C-XYZ as described in Example 10 for use in three different selection protocols.

FIG. 33A. Selection procedure utilizing the primer-selectors C-X, C-XY and C-XYZ, as shown in FIG. 30B, and polymerization reaction on the single-stranded template. FIG. 33B. Selection procedure utilizing strand-displacement hybridization reaction of the primer-selectors C-X, C-XY and C-XYZ facilitated by the removal of the displaced 5'-overhang DNA by exonuclease digestion, followed by polymerization reaction on the double-stranded template.

DESCRIPTION OF ILLUSTRATIVE EMBODIMENTS

Figure 1:
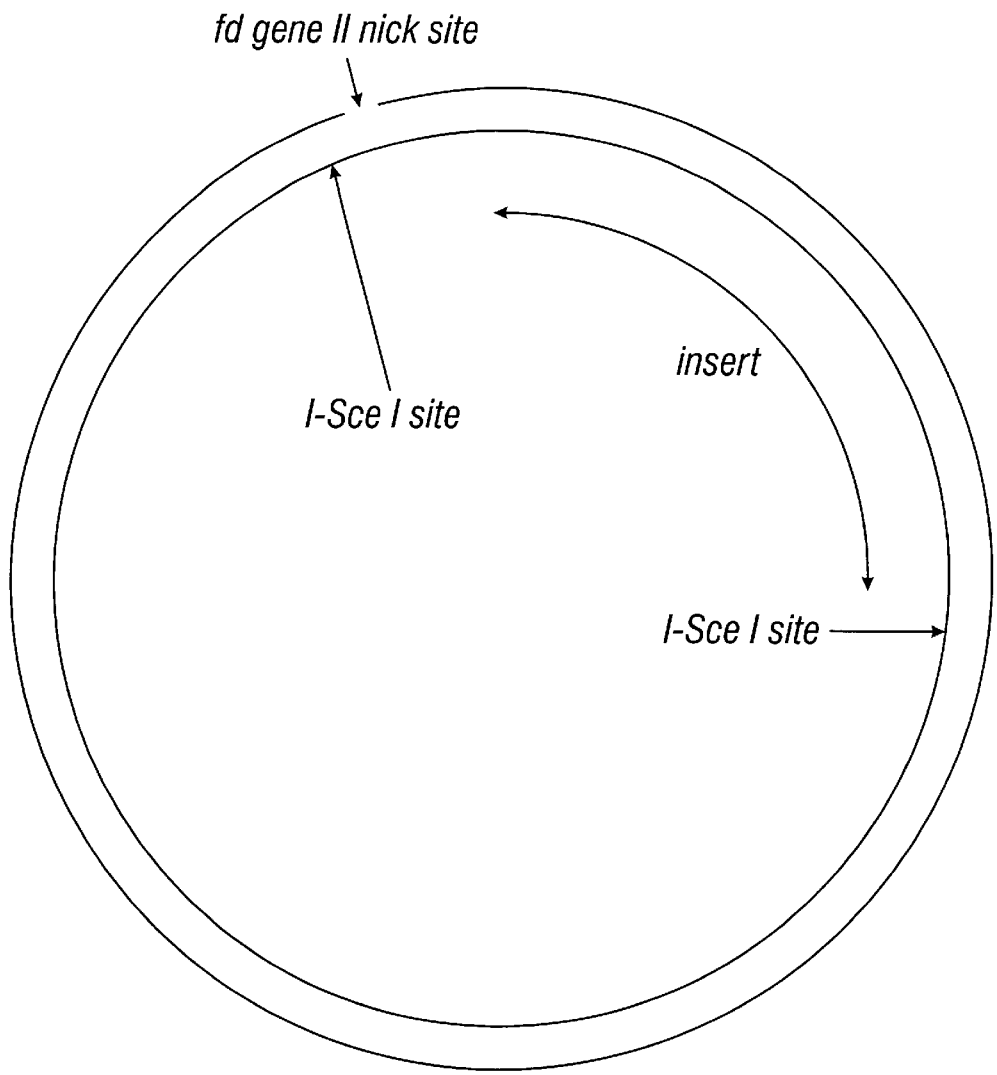
FIG. 1. A unique plasmid vector utilized in one embodiment of the method of double-stranded sequencing of the present invention. Shown is an insert to be sequenced, represented by the double-headed arrow, flanked by two endonuclease recognition and cleavage sites, in this case two I-SceI sites. An fd gene II nick site is used to create a nick by treatment with fd endonuclease. The nick is used to initiate the strand replacement sequencing reaction.

The limited length of DNA sequence that can be determined in one sequencing reaction is a fundamental problem in sequencing. Two types of solutions have been proposed and experimentally tested. The first type of solutions are all attempts to find better techniques to size-separate DNA molecules, including modifications to the composition of the electrophoretic gel matrix, modifications to the electrophoretic devices and electric field characteristics, using liquid chromatography, and using mass spectrometry to determine fragment lengths.

After years of refinement of electrophoretic methods, it is still not possible to separate molecules longer than about 1000–1400 bases with single-base resolution. This is because as the molecular weight of the DNA increases the gel bands become closer and closer together, until the bands from molecules of length n overlap those of length n+1, making it impossible to determine which base is at position n and which base is at position n+1. Additionally, due to technical limitations of the resolution and sensitivity of mass spectrometry, it has not been possible to separate molecules longer than about 50 to 100 bases with sufficient signal to noise ratio to distinguish molecules that differ in length by a single base (WO 96/32504).

The second type of solutions are attempts to avoid electrophoresis altogether. This class includes sequencing by microscopy, hybridization, step-by-step degradation of labeled bases from one end, and step-by-step addition of bases to one end. The microscopic methods depend upon determination (by direct imaging) of the position of a specific base along the DNA. In that respect they directly determine the distance between one end of the DNA molecule and the position of a specific base, and therefore share a common principle with all the size-separation techniques including gel electrophoresis. Electron microscopy, scanning tunneling microscopy, atomic force microscopy, and other microscopies have inherent resolution better than 0.2 nm, which is less than the spacing between DNA bases in double or single stranded DNA. Therefore, in principle, if individual base types could by identified by microscopy the entire sequence of a very long piece of DNA could be determined. Dispite many attempts to sequence by microscopy, technical problems including physical damage during imaging and difficulties in labeling and detecting specific bases have prevented this technique from being used to determine the position of specific bases, even in very short pieces of DNA.

Sequencing by hybridization is based on determining the presence of a specific short sequence (4–10 bases) without direct localization of the sequence on a longer piece of DNA (Drmanac et al., 1989). Computer analysis of the short sequences present can be used to reconstruct the sequence of a larger fragment of DNA. To date, this method is limited to DNA molecules of less than about 50 bases in length.

Methods of sequentially degrading bases from one end of a long DNA molecule using a exonuclease while simultaneously identifying the released bases have also been proposed (Jones et al., 1997). In principle this could be done using a single molecule or with a collection of identical molecules. The single-molecule methods have not proven practical due to difficulty in degrading the DNA rapidly enough and labeling and detecting the released labeled bases. The multi-molecule methods are not practical because all molecules in the set cannot be degraded synchronously.

Step-by-step incorporation of detectable bases from one end of a collection of identical molecules has also been proposed (WO 90/13666; WO 93/21340; U.S. Pat. Nos. 5,302,509; 5,750,341). In one version of this technique the specific base is identified by reduction in the amount of labeled nucleotide triphosphate precursors in the solution. In another version, the pyrphosphate molecules released during each polymerization step are detected in solution (Hyman, 1988; Ronghi et al., 1996, 1998). In a third version, the base is identified by incorporation and detection of a labeled nucleotide. All of these methods for step-by-step addition of nucleotides to one end of a collection of molecules suffer from the same shortcomings as encountered by the step-by-step degradation methods, specifically the difficulty to maintain registration of the positions of incorporation of nucleotides into different molecules.

The present invention overcomes these and other limitations present in the art. Certain aspects of the present invention increase the length of DNA sequence that can be determined from one biochemical reaction by increasing ability of any size-separation technique (e.g., mass spectroscopy, gel electrophoresis, gel chromatography) to determine the positions of bases. This principle, multibase sequencing, and all the instant methods described herein that implement the principle, reduces the number of fragments that need to be resolved in each gel lane or capillary and thereby increases the chance that the bands from molecules of similar size can be distinguished.

Multibase sequencing creates or selects a nested set of DNA double-stranded or single-stranded DNA molecules that have their proximal termini located at a specific position in the DNA sequence and their distal termini located at the positions of a specific dinucleotide (e.g., AT, TT, GT, etc.), trinucleotide (e.g., ATA, GGT, CTG, etc.), or n-base string (e.g., ATGCTGG). The DNA molecules created or selected with a specific base string at the distal ends are size-separated by electrophoresis, mass spectrometry, or other techniques to form a multi-base ladder similar to the single-base ladders formed in the Sanger or Maxim-Gilbert techniques.

For example, all those molecules terminated with the dinucleotide AT can be separated by electrophoresis to form a ladder of bands that specify the positions of the dinucleotide relative to the unique site at the proximal ends of the molecules. The average spacing between the bands will be about 16 bases (e.g., the average spacing between occurances of the dinucleotide AT). Because the average spacing between gel bands in the dinucleotide ladder is four times larger than the average spacing between bands in a conventional single-base ladder, adjacent sequencing bands will overlap less frequently and therefore be resolved more frequently.

In addition, even when bands in different dinucleotide ladders are of such similar size that they migrate the same distance, the information in the dinucleotide types can be used to resolve the sequence. For example, if a band of the "AT" ladder overlaps a band on the TG ladder, the sequence at that position can be determined to be ATG. An additional advantage of this approach is that the position of the central thymine base is determined from the information in two independent sequencing ladders. This "oversampling" of the information decreases the frequency of misidentification of the base at a specific position.

The information in all 16 possible dinucleotide ladders can be combined to determine the sequence even when three or more bands migrate identically. For example, if the dinucleotide ladders with molecules terminating at AT, GA, TG, NA, and AN overlap (where N is some other base), the sequence at a specific positions can be deetermined to be ATGA. The intensity of the dinucleotide bands can be used to determine the number of occurances of a specific dinucleotide within a region, even if the individual dinucleotide bands are not resolved. For example, if the dinucleotides TA, AT, and AA have indistinguishable electrophoretic mobility, and the AA band is twice as strong as the other bands, it can be determined that the sequence at that position is TAAAT. When the resolution of the size-separation technique is insufficient to unambiguously assign a specific sequence at a position, the information available will determine a small number of sequences allowed that will be a subset of all the sequences possible.

The determination of the unique sequence or limited set of sequences that are consistent with a specific pattern of multibase ladders can be determined as described above; however, the inventors also contemplate that computer software, such as that used for sequence analysis, comparing sequences in different genes and different organisms, determining the overlapping sequences of different fragments in shotgun sequencing, and in determining DNA sequences using the sequencing by hybridization approach, can be used or modified to assist in sequence determination using multibase sequencing.

The consequence of being able to determine the base sequence from multibase sequencing ladders with closely-spaced or completely overlapping bands is the ability to determine the base sequence in molecules longer than possible using single-base sequencing methods. As shown above, even if the size-separation technique is limited to distinguishing DNA length n from n+2, a dinucleotide ladder will be sufficient to determine the bases at position n, n+1, and n+2. By relaxing the resolution requirements by a factor of two (or more) the length of sequences that can be "read" from one size separation will be increased by approximately a factor of two. The ability to read longer sequences of DNA will improve sequencing using all technical methods of size-separation, including gel electrophoresis, liquid chromatography, and mass spectrometry.

In a most general sense, the present invention provides a number of methods that can be used in a variety of embodiments, including, but not limited to, creation of a nucleic acid terminated at one or more selected bases, sequence analysis of nucleic acids, mapping of sequence motifs within a nucleic acid as well as positional mapping of nucleic acid clones, and analysis of telomeric regions.

I. Creation of Nucleic Acid Product Terminated at a Selected Base

A. Methods for Creating an Initiation Site

In certain embodiments of the present invention, an initiation site for nucleic acid synthesis must first be created in the substantially double stranded nucleic acid. The initiation site (as distinct from an oligonucleotide primer) can be introduced by any method that results in a free 3' hydroxyl group on one side of a nick or gap in otherwise substantially double-stranded nucleic acid. Presented herein are a variety of methods for creation of an initiation site, including creation of a specific break or nick in one or both strands of the double-stranded nucleic acid, creation of a random break or nick in one or both strands of the double-stranded nucleic acid, creation of a single-stranded gap on one or both strands of the substantially double-stranded nucleic acid, and creation of a double-stranded break.

In certain of the methods of creating an initiation site described herein below, a nick or break is created that does not result in the formation of a 3' hydroxyl group. As the polymerase synthesis reactions described herein require a 3' hydroxyl group to initiate synthesis, also provided are methods of conditioning the break or nick, in order to create an initiation site that possesses a 3' hydroxyl group.

1. Creation of a Specific Break or Nick

In certain aspects of the present invention, it is desired to create an initiation site at one or more specific location(s) within the nucleic acid. Methods for creation of one or more specific breaks or nicks include, but are not limited to: enzymatic methods utilizing one or a combination of different enzymes; chemical cleavage methods; and methods involving the ligation of a specific nucleic acid adaptor.

a. Enzymatic Methods

There are a number of enzymes that have the ability to introduce a single- or double-stranded nicks or breaks into a nucleic acid at one or more specific positions. Examples of enzymatic methods for creating an initiation site include, but are not limited to, digestion of a nucleic acid by a restriction enzyme under conditions that only one strand of the double-stranded DNA template is hydrolyzed, and nicking by fl gene product II or homologous enzymes from other filamentous bacteriophage.

A number of restriction enzymes have been described that produce a single-stranded nick in one strand of a double-stranded nucleic acid when the digest is carried out in the presence of ethidium bromide (Kovacs et al., 1984). After the restriction endonuclease reaction produces a nick in one strand, no further reaction occurs. Therefore, most of the double-stranded nucleic acid molecules will have a single nick on one strand, with some molecules having a nick on the top strand, and some molecules having a nick on the bottom strand.

It is also known that certain restriction endonucleases produce a single-stranded nick in the normal strand of a hemiphosphorothiolated (having phosphorothioate linkages on only one strand) double-stranded nucleic acid molecule (Olsen et al., 1990). Depending on which strand contains the phosphorothioate linkages, the nick will be produced on the top strand or the bottom strand.

A preferred method of producing a specific nick in a double-stranded nucleic acid is by using the fl bacteriophage gene product II (fl endonuclease) or homologous enzymes from other filamentous bacteriophage such as the fd bacteriophage (Meyer and Geider, 1979). Certain single-stranded bacteriophages form a double-stranded "replicative form" (RF) molecule inside the host cell in order to replicate the bacteriophage genome. The RF is nicked at a specific site (the "origin of replication") on the strand corresponding to the bacteriophage genome, leading to replication of the bacteriophage genome by a strand displacement reaction, also known as rolling circle replication. Thus, a double stranded nucleic acid containing an origin of replication from a filamentous bacteriophage such as fl or fd, when contacted with the appropriate fl or fd endonuclease, would be specifically nicked at the origin of replication.

Additionally, uracil DNA glycosylase (dU glycosylase) removes uracil residues from nucleic acids, leaving an abasic site. This abasic site can be converted to a nick by heating the nucleic acid, treatment with base, or in combination with an enzyme such as, but not limited to, endonuclease IV or endonuclease V. Thus, by incorporating uracil into one or more specific locations in a double-stranded nucleic acid, for example by synthesizing an oligonucleotide primer with a uracil residue incorporated near the 3' end of the primer, and using the uracil-containing primer to amplify a double-stranded nucleic acid product, a specific nick can be created in the double-stranded nucleic acid product using these techniques.

b. Chemical Methods

Certain chemical methods can also be used to produce a specific nick or a break in a double-stranded nucleic acid molecule. For example, chemical nicking of a double-stranded molecule directed by triple-helix formation (Grant and Dervan, 1996).

c. Adaptor-Based Methods

Ligation can also be used to create an initiation site. This very powerful and general method to introduce an initiation site for strand replacement synthesis employs a panel of special double-stranded oligonucleotide adapters designed specifically to be ligated to the termini produced by restriction enzymes. Each of these adapters is designed such that the 3' end of the restriction fragment to be sequenced can be covalently joined (ligated) to the adaptor, but the 5' end cannot. Thus the 3' end of the adaptor remains as a free 3' OH at a 1 nucleotide gap in the DNA, which can serve as an initiation site for the strand-replacement sequencing of the restriction fragment. Because the number of different 3' and 5' overhanging sequences that can be produced by all restriction enzymes is finite, and the design of each adaptor will follow the same strategy, above, the design of every one of the possible adapters can be foreseen, even for restriction enzymes that have not yet been identified. To facilitate sequencing, a set of such adapters for strand replacement initiation can be synthesized with labels (radioactive, fluorescent, or chemical) and incorporated into the dideoxyribonucleotide-terminated strands to facilitate the detection of the bands on sequencing gels.

More specifically, adapters with 5' and 3' extensions can be used in combination with restriction enzymes generating 2-base, 3-base and 4-base (or more) overhangs. The sense strand (the upper strand shown in Table 1 below) of the adaptor has a 5' phosphate group that can be efficiently ligated to the restriction fragment to be sequenced. The anti-sense strand (bottom, underlined) is not phosphorylated at the 5' end and is missing one base at the 3' end, effectively preventing ligation between adapters. This gap does not interfere with the covalent joining of the sense strand to the restriction fragment, and leaves a free 3' OH site in the anti-sense strand for initiation of strand replacement synthesis.

TABLE 1

Adapters for Initiation of Strand Replacement DNA Synthesis (a) 2-base 5' restriction extensions:    5'------
                                          3'------ab
    Adapters with 3-base 5' extensions:              abcd---------3'
                                                     d---------5'
    Litigation product formed:           5'------abcd------------3'
                                          3'------ab d------------5'
(b) 3-base 5' restriction extensions:    5'------
                                          3'-------abc
    Adapters with 4-base 5' extensions:              abcde--------3'
                                                     e--------3'

TABLE 1-continued

Adapters for Initiation of Strand Replacement DNA Synthesis (c) 4-base 5' restriction extensions:    5'------
                                          3'------abcd
    Adapters with 5-base 5' extensions:              abcdef-----3'
                                                     f-----5'
(d) 2-base 3' restriction extensions:    5'------ab
                                          3'------
    Adapters with 1-base 3' extensions:              c---------3'
                                                     bc---------3'
(e) 3-base 3' restriction extensions:    5'------abcd
                                          3'------
    Adapters with 2-base 3' extensions:              d---------3'
                                                     bcd---------5'
(f) 4-base 3' restriction extensions:    5'------abcd
                                          3'------
    Adapters with 3-base 3' extensions:              e-------3'
                                                     bcde-------5'

TABLE 2

Base Extensions And Restriction Enzymes

| | Restriction endonucleases |
|---|---|
| 2-base extensions | |
| 5'-CG | MaeII, HinPI, NarI, AcyI, HpaII, MspI, TaqI, ClaI, SfuI, AsuII |
| 5'-GC | — |
| 5'-TA | NdeI, MaeI, MseI, AsnI |
| 5'-AT | AccI |
| CG-3' | CfoI, ImaI |
| GC-3' | KspI, SacII |
| TA-3' | — |
| AT-3' | PvuI |
| 3-base extensions | |
| 5'-GNC | Sau96, DraII |
| 5'-CNG | — |
| 5'-ANT | HinfI |
| 5'-TNA | DdeI, CelII, SauI, Bsu36I |
| GNC-3' | PssI |
| CNG-3' | — |
| ANT-3' | — |
| TNA-3' | — |
| 4-base extensions | |
| 5'-AATT | EcoRI |
| 5'-GATC | MboI, NdeII, Sau3A, BglII, BamHI, BclI, XhoII |
| 5'-CATG | NcoI, BspfHI |
| 5'-TATA | — |
| 5'-ATAT | — |
| 5'-GTAC | Asp718, SplI |
| 5'-CTAG | SpeI, NheI, AvrII, XbaI |
| 5'-TTAA | AflII |
| 5'-AGCT | HindIII |
| 5'-GGCC | EclXI, XmaIII, NotI, EaeI |
| 5'-CGCG | MluI, BssHII |
| 5'-TGCA | SnoI |
| 5'-ACGT | — |
| 5'-GCGC | BanI |
| 5'-CCGG | XmaI, MroI, Cfr101, SgrAl, AccIII |
| 5'-TCGA | SalI, XhoI |
| AATT-3' | — |
| GATC-3' | — |
| CATG-3' | NlaIII, SphI, NspI |
| TATA-3' | — |
| ATAT-3' | — |
| GTAC-3' | KpnI |
| CTAG-3' | — |
| TTAA-3' | — |
| AGCT-3' | SacI |
| GGCC-3' | ApaI |
| CGCG-3' | — |
| TGCA-3' | NsiI, PstI |

TABLE 2-continued

Base Extensions And Restriction Enzymes

| | Restriction endonucleases |
|---|---|
| ACGT-3' | AatII |
| GCGC-3' | BbeI, HaeII |
| CCGG-3' | — |
| TCGA-3' | — |

The adapters can also be designed to have a nick rather than a gap, which will still facilitate initiation of the strand replacement reaction. To do this, the restriction fragments need to be dephosphorylated to prevent ligation of the 5' end. In this case, blunt end adapters that are compatible with blunt end producing restriction enzymes can be used.

2. Creation of a Random Break or Nick

In other aspects of the present invention, it is desired to create an initiation site at one or more random or essentially random location(s) within the nucleic acid. Methods for creation of one or more random breaks or nicks include, but are not limited to: enzymatic methods utilizing one or a combination of different enzymes; chemical cleavage methods; and physical or mechanical methods.

a. Enzymatic Methods

A preferred method of generating random or essentially random breaks or nicks in a double-stranded nucleic acid is using a nuclease that has no particular sequence requirements for cleavage, for example an endonuclease such as DNAase I. DNAase I is commercially available from a variety of sources, and produces random or essentially random nicks or breaks in double-stranded DNA.

Another enzymatic method for generating random or essentially random breaks or nicks is through the use of a restriction enzyme, such as CviJI, that normally has a four base recognition sequence, but under certain buffer and salt conditions has essentially a two base recognition sequence. Other restriction endonucleases, including, but not limited to, ApoI,. AseI, BamHI, BssHII, EcoRI, EcoRV, HindIII, HinfI, KpnI, PstI, PvuII, SalI, ScaI, TaqI and XmnI, are known to possess "star activity," meaning that under certain conditions, such as high glycerol concentrations, high amounts of restriction enzyme, low ionic strength, high pH, the presence of certain organic solvents, such as DMSO, ethanol, ethylene glycol, dimethylacetamide, dimethylformamide or sulphalane, or substitution of the preferred divalent metal ion (usually $Mg^{2+}$) with a less preferred divalent metal ion, such as $Mn^{2+}$, $Cu^{2+}$, $Co^{2+}$ or $Zn^{2+}$, or combinations thereof, recognize and cleave sequences not normally cleaved.

Additionally, combinations of restriction enzymes, including those with four base recognition sequences, including, but not limited to, Tsp509I, MaeII, TaiI, AluI, CviJI, NlaIII, MspI, HpaII, BstUI, BfaI, DpnII, MboI, Sau3AI, DpnI, ChaI, HinPI, HhaI, HaeIII, Csp6I, RsaI, TaqI and MseI, and those having "star activity," can be used in a restriction enzyme "cocktail" to produce essentially random nicks or breaks in a double-stranded nucleic acid.

b. Chemical Methods

Single-strand breaks can also be produced using hydroxyl radicals generated by a number of methods including treatment with Fenton reaction reagents (a metal ion chelating agent, including, but not limited to EDTA and EGTA, a divalent metal ion, including, but not limited to, $Fe^{2+}$, $Ca^{2+}$, $Cu^{2+}$ and $Zn^{2+}$, a peroxide and a reducing agent, for example $Fe^{2+}/EDTA/H_2O_2$ with sodium ascorbate), or gamma irradiation. The primary products of radical cleavage are randomly-positioned nicks or gaps, usually with 3' phosphate groups. Therefore the DNA must be processed before the sites can be used to prime DNA synthesis (see Section 3 below).

In addition, a number of chemical compounds, particularly dyes, are known to produce hydroxyl radicals upon exposure to certain wavelengths of light.

c. Physical/Mechanical Methods

There are a number of physical and mechanical methods which are known to produce random single- and double-stranded breaks in nucleic acids. For example, it has long been known that subjecting DNA to hydrodynamic shear can produce random breaks in the DNA molecule. Additionally, sonication can be used, at various power levels, to produce random breaks or nicks in a nucleic acid molecule. Another method that is contemplated for use in the present invention to produce random nicks or breaks is nebulization, which is contacting the nucleic acid molecule with gas or air bubbles. Furthermore, repeated freezing and thawing of nucleic acids can produce random nicks or breaks.

3. Conditioning Nick to Generate 3' Hydroxyl Group

All polymerases studied require 3' ends with hydroxyl groups in order to incorporate new nucleotides. Therefore breaks in the DNA that do not originally contain 3' OH groups have to be conditioned to possess 3' OH groups before strand elongation can be performed. One method to condition the 3' end is to incubate the DNA in the presence of a 3' exonuclease such as E. coli exonuclease III, or a DNA polymerase that possesses 3' to 5' exonuclease activity. This invention anticipates discovery or engineering of DNA polymerases able to remove nucleotides that do not have 3' OH groups from the 3' ends of DNA strands.

4. Extension of Break or Nick to Form Single-Stranded Gap

In certain aspects of the invention, a nick or break in the nucleic acid must be extended to form a gap, for example for insertion of bases by a DNA polymerase that lacks strand displacement or 5' to 3' exonuclease activity, such as T4 DNA polymerase, or to create a site for primer binding.

A preferred enzyme for use in this aspect of the invention is exonuclease III, which can extend a nick or break to form small or large gaps, as desired for the particular application. The exonuclease III reaction is allowed to proceed for a short time to produce small gaps, and longer for larger gaps.

5. Creation of Blunt End

In particular aspects of the invention, a double-stranded break is required that is blunt. A number of restriction endonucleases are known that produce blunt ends, including, but not limited to, AluI, CviJI, BstUI, DpnI, HaeIII, RsaI, SspI, Eco47III, StuI, ScaI, PmlI, BsaAI, PvuII, MspA1I, Ecl136II, EcoRV, SmaI, NaeI, EheI, Bst1107I, HincII, HpaI, SnaBI, NruI, FspI, MscI and DraI. These enzymes can be used in conjunction with phosphatases, such as bacterial alkaline phosphatase, calf-intestinal alkaline phosphatase or shrimp alkaline phosphatase, to remove the phosphate groups present at the blunt sites.

B. Double-Stranded Templates

Template DNA can be any double-stranded DNA molecule including, but not limited to native chromosomal or extrachromosomal DNA from any organism, DNA cloned into a bacterial plasmid or virus, plasmids or RF forms of viral DNA, double stranded amplification products, including PCR™ products, and artificially synthesized DNA. Linear and circular DNA of all double-stranded conformations isolated by any technique and of any purity can be used. Although in certain aspects of the invention it is preferred that the template DNA be essentially free from nicks or gaps, DNA samples that do not originally meet this requirement can be treated to remove such defects. Nicks in DNA occur after long-term storage or repeated cycles of freezing and thawing; these defects can be repaired by incubating the DNA with a DNA ligase such as that from bacteriophage T4, or by incubation with a combination of enzymes that repair such defects, as described herein. Gaps can be repaired by incubation with T4 DNA polymerase and ligase.

The fact that the template DNA molecules are double-stranded obviates the problems with unusual secondary structures. Moreover, the fact that the product molecules are double-stranded allows long stretches of the product DNA to be subsequently cleaved using restriction enzymes into fragments sufficiently small that they can be subjected to automated sequencing in commercially available sequenators (e.g. those made by ABI, Pharmacia, and other companies).

In certain aspects of the invention, the double-stranded nucleic acid template is a restriction fragment from a larger nucleic acid precursor. Restriction enzymes can be used to cut the DNA at sequence specific sites. At least one hundred of these cleavage reagents are commercially available and are able to make double-strand scissions in the DNA in short times. Additionally, other enzymes that cleave DNA in a specific location can be used, for example intron encoded endonucleases such as I-CeuI, I-PpoI, I-TliI and I-SceI, are contemplated for use. In addition to these natural sequence specific endonucleases there are a number of chemical reagents developed to make specific breaks in DNA (Strobel and Dervan, 1992; Grant and Dervan, 1996).

2. Amplification Techniques

Nucleic acids used as a template for amplification can be isolated from cells according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA and is used directly as the template for amplification.

Pairs of primers that selectively hybridize to a specific nucleic acid template are contacted with the isolated nucleic acid under conditions that permit selective hybridization. The term "primer", as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred.

Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

In certain aspects of the invention, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (Affymax technology).

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and each incorporated herein by reference in entirety.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641, filed Dec. 21, 1990, incorporated herein by reference. Polymerase chain reaction methodologies are well known in the art.

Another method for amplification is the ligase chain reaction ("LCR"), disclosed in EPA No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, incorporated herein by reference, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention.

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR Gingeras et al., PCT Application WO 88/10315, incorporated herein by reference. In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

Davey et al., EPA No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, M. A., In: *PCR PROTOCOLS. A GUIDE TO METHODS AND APPLICATIONS*, Academic Press, N.Y., 1990 incorporated by reference).

Methods based on ligation of two (or more) oligonucleotides in the presence of nucleic acid having the sequence of the resulting "di-oligonucleotide", thereby amplifying the di-oligonucleotide, may also be used in the amplification step of the present invention.

Following any amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods (Sambrook et al., 1989).

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography.

C. Effective Polymerases

Suitable polymerases are those DNA polymerases that demonstrate a relatively rapid rate of synthesis and can prime synthesis from a 3' hydroxyl group. In certain aspects of the invention, polymerases having a 5'–3' exonuclease activity to degrade one of the template strands are preferred. In other aspects of the invention, polymerases which possess strand displacement activity, whether or not they have 5' to 3' exonuclease activity, are preferred. And in particular embodiments, polymerases that have neither 5' to 3' exonuclease activity nor strand displacement activity are preferred.

In principle, the enzymes for use in the present invention could have an associated 3' to 5' exonuclease ("proofreading") activity, which might improve the ability to sequence very large molecules of DNA. All of the enzymes listed herein below (except Taq DNA polymerase, Tth DNA polymerase, Tfl DNA polymerase, Bst DNA polymerase, Vent$_R$ (exo⁻), Deep VentR (exo⁻), E. coli DNA polymerase I Klenow fragment and DNA polymerase I (pol I) from *M. tuberculosis*) seem to have this proof reading activity.

Optimization of any of the polymerases listed herein below is contemplated in the present invention. Optimization of the polymerases involves testing different polymerases and mutants thereof under the conditions of the sequencing reactions. Indeed, rate of synthesis, fidelity of incorporation of natural nucleotides and nucleotide analogs, and length of the synthesized strands can be adjusted using standard methods (e.g. changing salt conditions, nucleotide triphosphate compositions and concentrations, temperature, time, etc.) known to those familiar with the art of sequencing. Directed mutagenesis of the polymerase is also well-known in the art. Such genetically engineered enzymes can be endowed with both the ability to tolerate a wider range of reaction conditions and improved sequencing product yield.

With regard to genetically engineered enzymes, the present invention specifically contemplates polymerases modified according to the teachings of Tabor and Richardson, EP 0 655 506 B1, hereby incorporated by reference. Such modifications comprise mutations to the binding site which results in better incorporation of dideoxynucleotides (as compared to unmodified polymerases), while retaining other favorable activities.

1. Polymerases Having 5' to 3' Exonuclease Activity

In certain aspects of the present invention, polymerases having 5' to 3' exonuclease activity are preferred for use. Examples of polymerases known to have 5' to 3' exonuclease activity include, but are not limited to E. coli DNA polymerase I (Kornberg and Baker, 1992), DNA polymerase from *Thermus aquaticus* (hereinafter "Taq DNA polymerase"), which is a thermostable enzyme having 5'–3' exonuclease activity but no detectable 3'–5' activity (Longley et al., 1990; Holland et al., 1991), ΔTaq DNA polymerase (Barnes, 1992; commercially available from United States Biochemical), DNA polymerase I (pol A) from *S. pneumoniae* (Lopez et al., 1989), Tfl DNA polymerase from *Thermus flavus* (Akhmetzjanov and Vakhitov, 1992), DNA polymerase I (pol I) from *D. radiodurans* (Gutman et al., 1993), Tth from *Thermus thermophilus* (Myers and Gelfand, 1991), recombinant Tth XL from *Thermus thermophilus* (commercially available from Perkin-Elmer), DNA polymerase I (pol I) from *M. tuberculosis* (Hiriyanna and Ramakrishnan, 1981), DNA polymerase I (pol I) from *M. thermoautotrophicum* (Klimczak et al., 1986), wild-type (unmodified) T7 DNA polymerase (Hori et al., 1979; Engler et al., 1983, Nordstrom et al., 1981), and DNA polymerase I (UL30) from herpes simplex virus (Crute and Lehman, 1989).

2. Polymerases Having Strand Displacement Activity

In certain aspects of the invention, in addition to those polymerases listed above, polymerases that have strand displacement activity but lacking 5' to 3' exonuclease activity are preferred for use. Polymerases that lack 5' to 3' exonuclease activity include, but are not limited to, *E. coli* DNA polymerase I Klenow fragment (Jacobsen et al., 1974), modified T7 DNA polymerase (Sequenase®, commercially available from United States Biochemical; Tabor and Richardson, 1989, 1990), DNA polymerase large fragment from *Bacillus stearothermophilus* (commercially available from New England BioLabs), *Thermococcus litoralis* DNA polymerase (Vent$_R$® DNA polymerase, commercially available from New England BioLabs; Mattila et al., 1991; Eckert and Kunkel, 1991), *Thermococcus litoralis* DNA polymerase modified to eliminate the 3' to 5' exonuclease activity (Vent$_R$® (exo⁻) DNA polymerase, commercially available from New England BioLabs; Kong et al., 1993), Pyrococcus species GB-D DNA polymerase (Deep Vent$_R$™ DNA polymerase, commercially available from New England BioLabs), Pyrococcus species GB-D DNA polymerase modified to eliminate the 3' to 5' exonuclease activity (Deep Vent$_R$™ (exo⁻) DNA polymerase, commercially available from New England BioLabs), and ThermoSequenase® DNA polymerase (commercially available from Amersham).

3. Polymerases Effective With Gapped Templates

In addition to those polymerases discussed above, polymerases such as T4 DNA polymerase, which do not have either 5' to 3' exonuclease activity or strand displacement activity, are effective polymerases in aspects of the invention where gapped templates are used. All polymerases capable of synthesis using a 3' hydroxyl group as a primer are suitable for use in these aspects of the invention.

4. Engineered Polymerases

Additionally, the present invention contemplates optimization of any of the polymerases listed herein above. Techniques for directed mutagenesis of DNA polymerases is well-known in the art. Such genetically engineered enzymes can be endowed with both the ability to tolerate a wider range of reaction conditions and improved sequencing product yield. With regard to genetically engineered enzymes, the present invention specifically contemplates polymerases modified according to the teachings of Tabor and Richardson, EP 0 655 506 B1, hereby incorporated by reference.

Site-specific mutagenesis is a technique useful in the preparation of modified proteins or peptides, through specific mutagenesis of the underlying DNA. The technique, well-known to those of skill in the art, further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 14 to about 25 nucleotides in length is preferred, with about 5 to about 10 residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double-stranded vector which includes within its sequence a DNA sequence which encodes the desired polymerase to be modified. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the polymerase-encoding DNA segments using site-directed mutagenesis is provided as a means of producing potentially useful species and is not meant to be limiting as there are other ways in which sequence variants of polymerases and the DNA sequences encoding them may be obtained. For example, recombinant vectors encoding the desired polymerase sequence may be treated with mutagenic agents, such as hydroxylamine, to obtain sequence variants. Specific details regarding these methods and protocols are found in the teachings of Maloy et al, 1994; Segal, 1976; Prokop and Bajpai, 1991; Kuby, 1994; and Maniatis et al., 1982, each incorporated herein by reference, for that purpose.

As one illustrative example of the protocols which are known to those of skill in the art for making mutants, the PCRTm-based strand overlap extension (SOE) (Ho et al., 1989) for site-directed mutagenesis is particularly preferred for site-directed mutagenesis of the polymeraes to be modified. The techniques of PCR™ are well-known to those of skill in the art, as described herein. The SOE procedure involves a two-step PCR™ protocol, in which a complementary pair of internal primers (B and C) are used to introduce the appropriate nucleotide changes into the wild-type sequence. In two separate reactions, flanking PCR™ primer A (restriction site incorporated into the oligo) and primer D (restriction site incorporated into the oligo) are used in conjunction with primers B and C, respectively to generate PCR™ products AB and CD. The PCR™ products are purified by agarose gel electrophoresis and the two overlapping PCR™ fragments AB and CD are combined with flanking primers A and D and used in a second PCR™ reaction. The amplified PCR™ product is agarose gel purified, digested with the appropriate enzymes, ligated into an expression vector, and transformed into E. coli JM101, XL1-Blue™ (Stratagene, LaJolla, Calif.), JM105, or TG1 (Carter et al., 1985) cells. Clones are isolated and the mutations are confirmed by sequencing of the isolated plasmids.

D. Extension

In most aspects of the invention, an extension reaction is performed before termination. The extension reaction results in incorporation of deoxynucleotides and certain deoxynucleotide analogs. In a most general sense, a standard extension reaction includes each of the four "standard" deoxynucleotide triphosphates: dATP, dCTP, dGTP and dTTP, however, in certain embodiments of the invention, one, two or three deoxynucleotides are used in the extension reaction. Additionally, in certain preferred aspects described in detail herein, dUTP is included in the extension reaction (or in the primer for use in an amplification reaction) to provide a substrate for enzymes, such as uracil DNA glycosylase, to produce an abasic site at one or more positions in the nucleic acid. These abasic sites can be converted to nicks or breaks through heat, base treatment, or treatment with additional enzymes, such as endonuclease IV and/or endonuclease V. In other aspects of the invention described in detail herein below, one or more deoxynucleotide phosphorothioates or boranophosphates are included in the extension reaction.

Another preferred aspect of the present invention concerns the use of one or more deoxynucleotide precursors that have a detectable label, or an isolation or immobilization tag. Preferred labels and tags are described in detail herein below.

E. Termination

In certain embodiments of the present invention, the Strand Replacement reactions are terminated by incorporation of a dideoxyribonucleotide instead of the homologous naturally-occurring nucleotide. This terminates growth of the new DNA strand at one of the positions that was formerly occupied by dA, dT, dG, or dC by incorporating ddA, ddT, ddG, or ddC. In principle the reaction can be terminated using any suitable nucleotide analogs that prevent continuation of DNA synthesis at that site. For certain applications, such as the determination of the length of telomeres, the polymerization reaction can be terminated when the polymerase cannot insert a particular nucleotide, because it is missing from the reaction mixture.

Polymerization can also be terminated specific distances from the priming site by inhibiting the polymerase a specific time after initiation. For example, under specific conditions Taq DNA polymerase is capable of strand replacement at the rate of 250 bases/min, so that arrest of the polymerase after 10 min occurs about 2500 bases from the initiation site. This strategy allows for pieces of DNA to be isolated from different locations in the genome.

F. Cleavage

Because all of the template and synthetic DNA remains double-stranded, except at the site of termination, where there is a nick or small gap, restriction enzymes can be used to cut the DNA at sequence specific sites. At least one hundred of these cleavage reagents are commercially available and are able to make double-strand scissions in the DNA in short times. In addition to these natural sequence specific endonucleases there are a number of chemical reagents developed to make specific breaks in DNA (Strobel and Dervan, 1992; Grant and Dervan, 1996).

G. Tags/Labels

In preferred aspects of the invention, the nucleic acid template and/or the synthesized strand includes one or more detectable label and/or isolation or immobilization tag. Use of these labels and tags in a variety of different embodiments of the invention are detailed herein.

1. Isolation Tags

In certain aspects of the invention, the nucleic acids comprise a tag that can be used to isolate and/or immobilize the nucleic acids having the tag. Affinity labels (e.g., biotin/streptavidin; hapten/antibody complexes, with common haptens being digoxigenin, fluorescein, BrdU; triplex-forming sequences, thiol groups, and sequence-specific DNA binding proteins (e.g., lac repressor)) are preferred in certain embodiments.

Substrates used to immobilize the nucleic acids include, but are not limited to, surfaces of microwell plates, centrifuge tubes, streptavidin-conjugated paramagnetic particles, streptavidin-conjugated, filters, and chromatographic media containing thiol groups, metal ions, streptavidin, antibodies.

2. Detectable Labels

Another embodiment of the invention comprises nucleic acids labeled with a detectable label. Label may be incorporated at a 5' terminal site, a 3' terminal site, or at an internal site within the length of the nucleic acid. Preferred detectable labels include a radioisotope, a stable isotope, an enzyme, a fluorescent chemical, a luminescent chemical, a chromatic chemical, a metal, an electric charge, or a spatial structure. There are many procedures whereby one of ordinary skill can incorporate detectable label into a nucleic acid. For example, enzymes used in molecular biology will incorporate radioisotope labeled substrate into nucleic acid. These include polymerases, kinases, and transferases.

Preferably, the nucleic acids are labeled with one or more fluorescent dyes, e.g. as disclosed in U.S. Pat. No. 5,188,934 and PCT application PCT/US90/05565. In other aspects of the invention, affinity labels (groups that can be bound to detectable groups, e.g., biotin/streptavidin; hapten/antibody with common haptens being digoxigenin, fluorescein, BrdU, thiol groups) are used. Additionally, chemiluminescent and chemifluorescent labels, and enzymatic labels, such as alkaline phosphatase, glucose oxidase, luciferase, green fluorescent protein, β-glucuronidase and β-galactosidase are preferred in certain aspects of the invention. In other aspects of the invention, the labeling isotope is preferably, $^{32}P$, $^{35}S$, $^{14}C$, or $^{125}I$.

The nucleic acids of the invention can be labeled in a variety of ways, including the direct or indirect attachment of radioactive moieties, fluorescent moieties, colorimetric moieties, and the like. Many comprehensive reviews of methodologies for labeling DNA and constructing DNA probes provide guidance applicable to constructing probes of the present invention. Such reviews include Matthews et al. (1988); Haugland (1992); Keller and Manak (1993); and Eckstein (1991); and Wetmur (1991). Additional methodologies applicable to the invention are disclosed in Connolly (1987); Gibson et al. (1987); Spoat et al. (1987); U.S. Pat. Nos. 4,757,141; 5,151,507; 5,091,519; Jablonski et al. (1986); and U.S. Pat. No. 5, 124,246. Attachment sites of labeling moieties are not critical in embodiments relying on probe labels to identify nucleotides in the target polynucleotide, provide that such labels do not interfere with the strand replacement or nick formation steps. In particular, dyes may be conveniently attached to the end of the probe distal to the target polynucleotide on either the 3' or 5' termini of strands making up the probe, e.g. Eckstein (cited above), Fung (cited above), and the like. In some embodiments, attaching labeling moieties to interior bases or inter-nucleoside linkages may be preferred.

The label may be directly or indirectly detected using scintillation fluid or a PhosphorImager, chromatic or fluorescent labeling, or mass spectrometry. Other, more advanced methods of detection include evanescent wave detection of surface plasmon resonance of thin metal film labels such as gold, by, for example, the BIAcore sensor sold by Pharmacia, or other suitable biosensors.

II. Sequencing Methods

In certain aspects, the present invention can be considered to be an improvement over the standard Sanger method of DNA sequencing. As noted above, the Sanger enzymatic method (i.e., dideoxy chain termination method) requires a DNA polymerase enzyme to elongate a short primer DNA that is hybridized to a single-stranded template. In other words, current Sanger DNA sequencing protocols require that double-stranded DNA for sequencing first be denatured to enable the primer to bind to the priming site (Murphy, 1993). By contrast, the present invention does not contemplate denaturation of the double-stranded template; rather, sequencing can be carried out directly on the double-stranded template.

The Sanger technique involves 1) denaturation to generate single-stranded DNA, 2) hybridization of an oligonucleotide primer to a unique site of known sequence on the single-stranded DNA, 3) extension of the primer using Taq, T7, or other DNA polymerase to generate a double-stranded product, 4) termination of the synthesis at specific bases by using terminating agents [e.g., incorporating specific dideoxyribonucleotides (ddNTPs)], 5) denaturation of the double-stranded product, and 6) electrophoresis of the denatured DNA to separate the molecules by size. If synthesis is performed with all four dNTPs (nucleic acid precursors) and terminated with labeled ddATP then the strands synthesized will all begin with 5' end of the primer and end at different positions where dideoxyriboadenosine has been incorporated in place of adenosine. In this case the distribution of fragment lengths reflect the spatial distribution of thymidine along the template strand. To determine the positions of each of the other three bases, separate reactions can be done to incorporate ddTTP, ddCTP, and ddGTP. For detection the synthetic DNA can be detected by hybridization, incorporation of labeled primers, incorporation of labeled nucleotides, or incorporation of labeled dideoxyribonucleotides. When fluorescently tagged dideoxyribonucleotides with different fluorescent spectra are used to terminate synthesis a laser can be used to distinguish between DNA molecules terminated with each of the four ddNTPs, such that only a single primer extension reaction and single electrophoresis lane needs to be run to determine the position of all four bases.

An important disadvantage of the current Sanger method is that certain sequences (such as strings of guanine) are difficult to sequence due to the propensity of some sequences to form intramolecular and intermolecular secondary structure, which causes the polymerase to terminate prematurely or to add an incorrect dideoxyribonucleotide. In addition each sequencing reaction is only able to determine the sequence of only 400–800 nucleotides immediately adjacent to the primer. The present invention provides a method for overcoming both problems.

The method of the present invention represents an enhancement of the Sanger Method. Using a suitable polymerase (described in more detail below), the present invention allows for the sequencing of undenatured, double-stranded DNA. In one embodiment, the process involves a controlled "nicking" of one strand of the double-stranded template followed by a strand replacement (SR).

A. Specific Nicking

1. Nick Translation

The strand replacement method of the present invention can be used to sequence a variety of templates. Such templates, include, but are not limited to, circular double-stranded templates and linear double-stranded templates produced by restriction or PCR™ amplification.

a. Parallel Sequencing Of Multiple Restriction Fragments From Circular DNA

Figure 2:
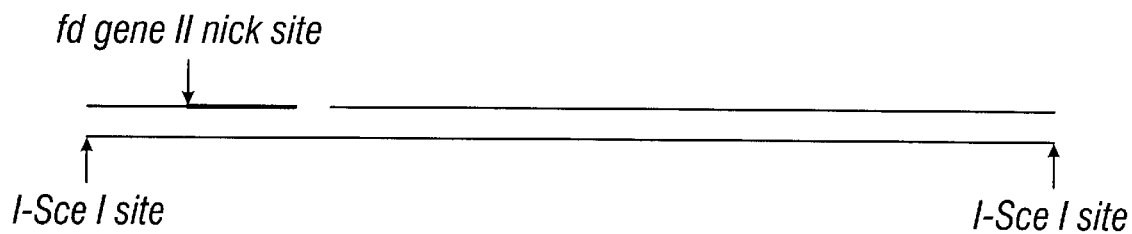
FIG. 2. Schematically shows a strand-specific nick at the fd gene II site of a double-stranded template flanked by I-SceI sites to initiate the strand replacement reaction of the present invention. The newly synthesized strand is shown as a bold line.
Figure 3:
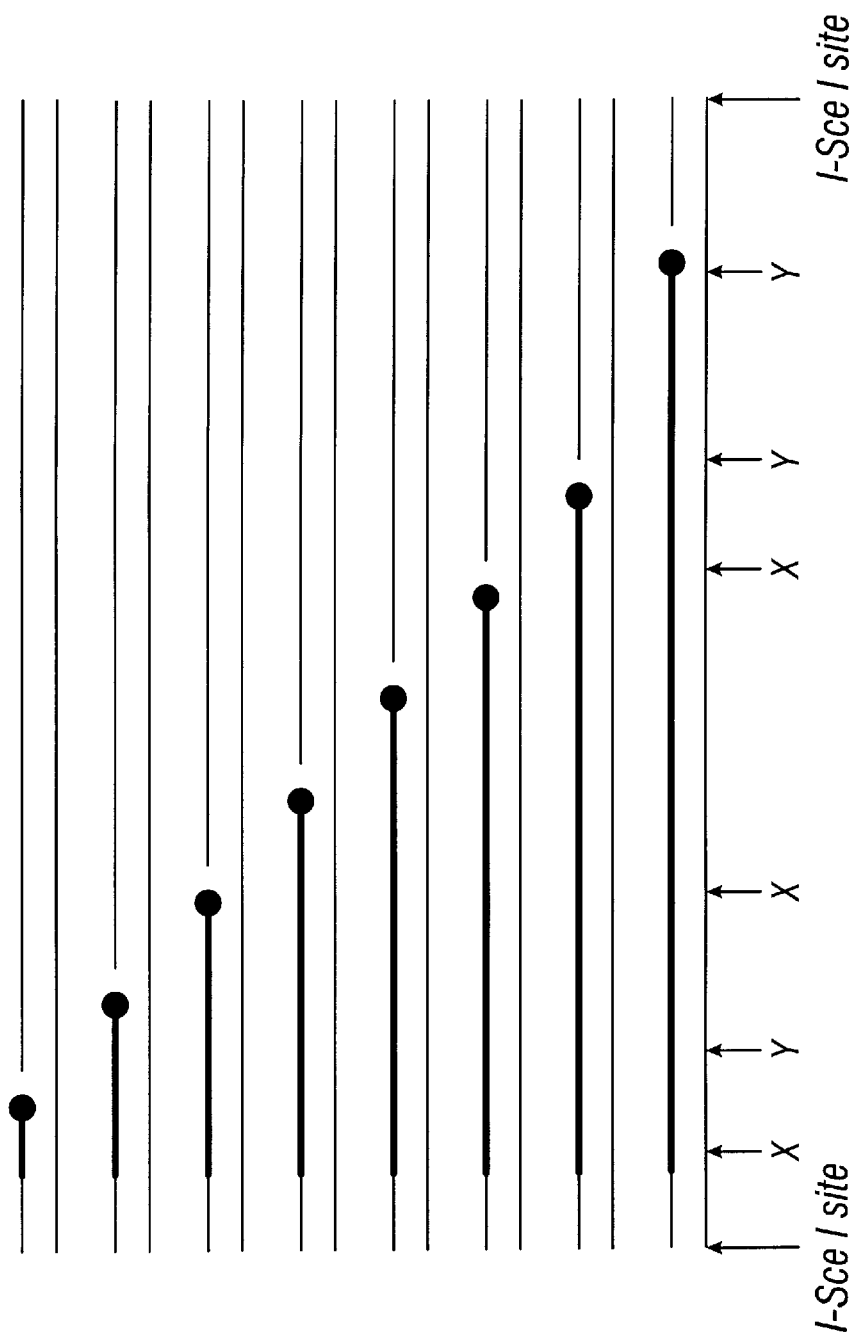
FIG. 3. Schematically shows the products of the stand replacement method when carried out in the presence of termination nucleotides (closed circles). Also shown is the optional step of restriction digestion at restriction endonuclease sites X and Y.

One embodiment of the invention is schematically shown in FIG. 1, FIG. 2, and FIG. 3. In this embodiment, the DNA to be sequenced is cloned into a special vector having the following features: 1) a relatively rare endonuclease recognition site (I-Sce I sites) on each side of the insert, 2) a single nick site (fl gene II site) on one side of the insert such that the 3' end of the nick is oriented toward the insert, and 3) the insert (i.e. the DNA to be sequenced). In this embodiment, no oligonucleotide primer is used.

The fl gene product II (hereinafter "gpII" or "fl endonuclease") produces a sequence specific, strand-specific nick that can prime DNA synthesis by E. coli pol I (Meyer and Geider, 1979). This process requires a core sequence of about 50 bp on the template DNA (Dotto and Zinder, 1984). In the presence of 5 mM Mg, gpII nicks about 50% of supercoiled plasmid and relaxes the other half. The entire fl intergenic region is the origin of replication of fl phage, and has been cloned into a number of commercially available vectors (e.g. pSPORT available from Life Technologies). A mutant gpII (G73A) has been cloned, overexpressed, and studied (Higashitani et al., 1992). This mutant protein has a relaxed requirement for plasmid supercoiling, produces mainly nicks rather than relaxed circles, and binds more cooperatively to the core site.

The plasmid (FIG. 1) is first digested with an enzyme (e.g., the fl gene II product) which makes a strand-specific nick (i.e., a nick at one site on one of the stands of the double-stranded plasmid) at a specific recognition sequence, and then digested with the restriction enzyme corresponding to the endonuclease recognition sites (e.g., I-Sce I which is a commercially available 18-base specific endonuclease). Taq polymerase, dATP, dTTP, dGTP, and dCTP along with optimized concentrations of the four labeled (e.g. fluorescently-labeled) dideoxyribonucleotides ddATP*, ddTTP*, ddGTP*, and ddCTP* are added and a strand replacement reaction is begun to synthesize a new DNA strand (shown bold in FIG. 2) complementary to one strand of the template DNA. Whenever a ddNTP is incorporated into the DNA, the chain is terminated and labeled with the ddNTP complementary to the one strand of template (shown as large dots in FIG. 3). This produces a distribution of double-stranded fragments, shown in FIG. 3. These molecules are then denatured and a sequencing ladder generated using standard automated sequencing gels and ddNTP detection systems.

In the case where the insert is too long to be sequenced on a single gel, the I-Sce I fragment can be cleaved (after reaction with Taq DNA polymerase) using other restriction enzymes. In the case shown in FIG. 3, two restriction enzymes (X and Y) produce eight restriction fragments to be sequenced. The overlapping sequences from the resolved restriction fragments will determine the entire sequence of the insert. Note that the restriction fragments can be resolved on double-stranded gels as bands of discrete length. The ability to fractionate DNA according to length is not affected by the presence of nicks in the double-stranded DNA. As noted above, it is well-known that double-stranded DNA with nicks or other flexible joints forms sharp bands during electrophoresis (Higashitani et al., 1992). Only at the step that a denaturing sequencing gel of each restriction fragment is performed will a ladder of bands at single-base intervals be produced.

Alternative procedures could be used for many of the steps. The strand replacement reaction could be performed by a different polymerase, such as $E. coli$ polymerase I. The restriction fragments produced by enzymes X and Y could be separated by capillary or slab electrophoresis. The ddNTP-terminated nucleic acids could be labeled with different colored dyes or with radioactivity.

An example of the steps necessary to do the sequencing of a large insert would be: 1) make the nick with fl gene II product and cleave with I-Sce I; 2) add polymerase (e.g., Taq DNA polymerase) and nucleotide triphosphates (dNTPs and ddNTPs) for a fixed time; 3) restrict half of the sample with enzyme X and the other half with enzyme Y; 4) in parallel, separate the X and Y restriction fragments by capillary electrophoresis; 5) denature each of the isolated restriction fragments and sequence in a conventional sequencing apparatus. Steps 1–3 can be performed successively in the same tube. In principle, steps 4 and 5 could be done automatically within the sequencing device.

b. Parallel Sequencing Of Multiple Restriction Fragments From Linear DNA

Figure 4A:
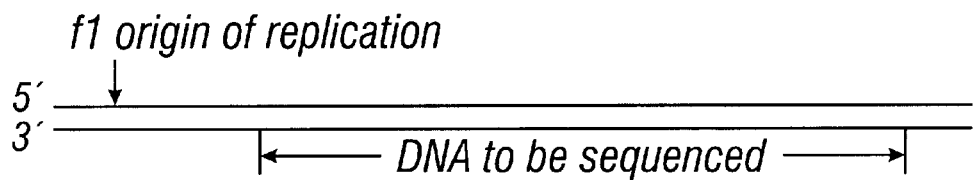
FIG. 4A, FIG. 4B, FIG. 4C, FIG. 4D, FIG. 4E, FIG. 4F, FIG. 4G, FIG. 4H, and FIG. 4I. Schematically shows one embodiment of the strand replacement method of the present invention used to map the positions of bases along DNA of multiple restriction fragments.
Figure 4B:
Figure 4C:
Figure 4D:
Figure 4E:
Figure 4F:
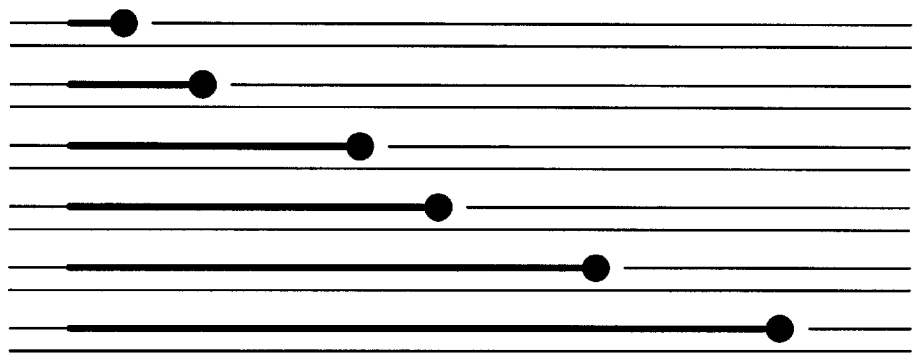
Figure 4G:
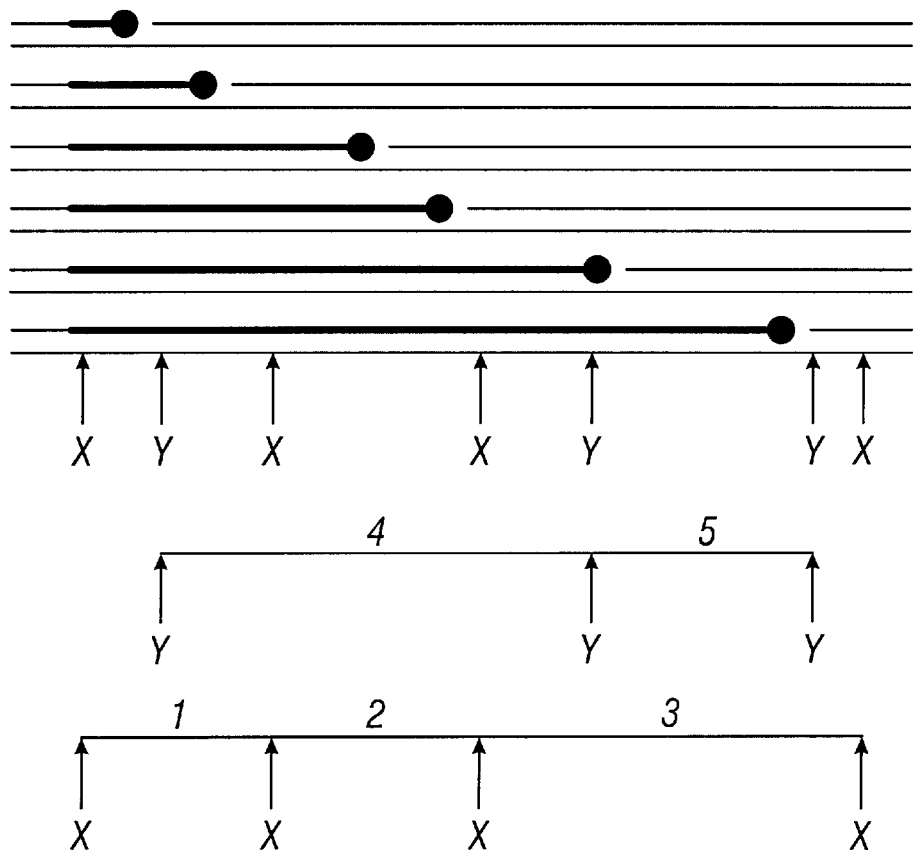
Figure 4H:
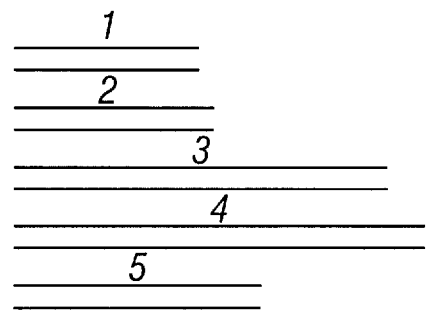
Figure 4I:
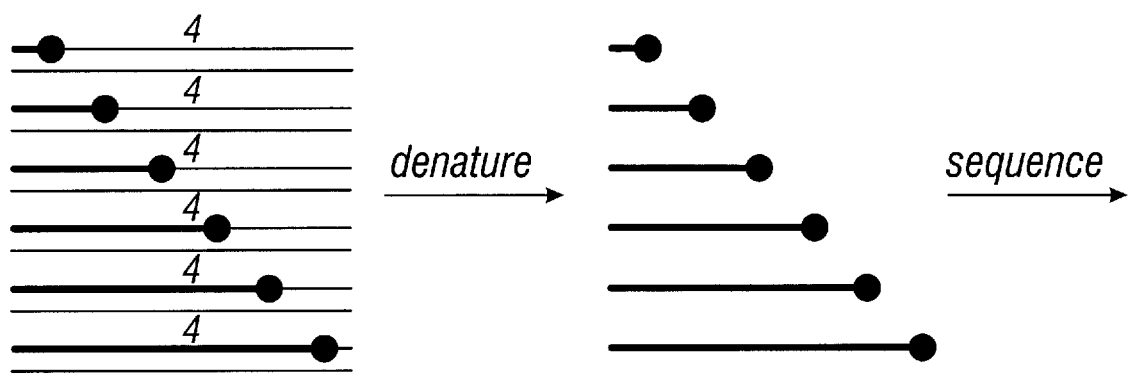

In one embodiment, the strand replacement method of the present invention is used to map the positions of bases along DNA of multiple restriction fragments. A double stranded DNA template is used (FIG. 4A). A nick is made in one of the strands (FIG. 4B). A strand replacement reaction is initiated (FIG. 4C). The products are generated in the presence of termination nucleotides (4 ddNTPs) (FIG. 4D) and elongation is thereby terminated (FIG. 4E). The products represent nucleic acid terminated at different sites (e.g. different adenine sites) (FIG. 4F). Two restriction endonuclease cleavage reactions of the products are performed with different enzymes (X and Y) (FIG. 4G). The restriction fragments are fractionated according to size (FIG. 4H). Thereafter, each fragment can be denatured and sequenced (FIG. 4I, illustrative results are shown for strand #4 from FIG. 4H) using conventional denaturing sequencing gels.

c. Sequencing DNA Adjacent To A Series Of Restriction Sites

Figure 5:
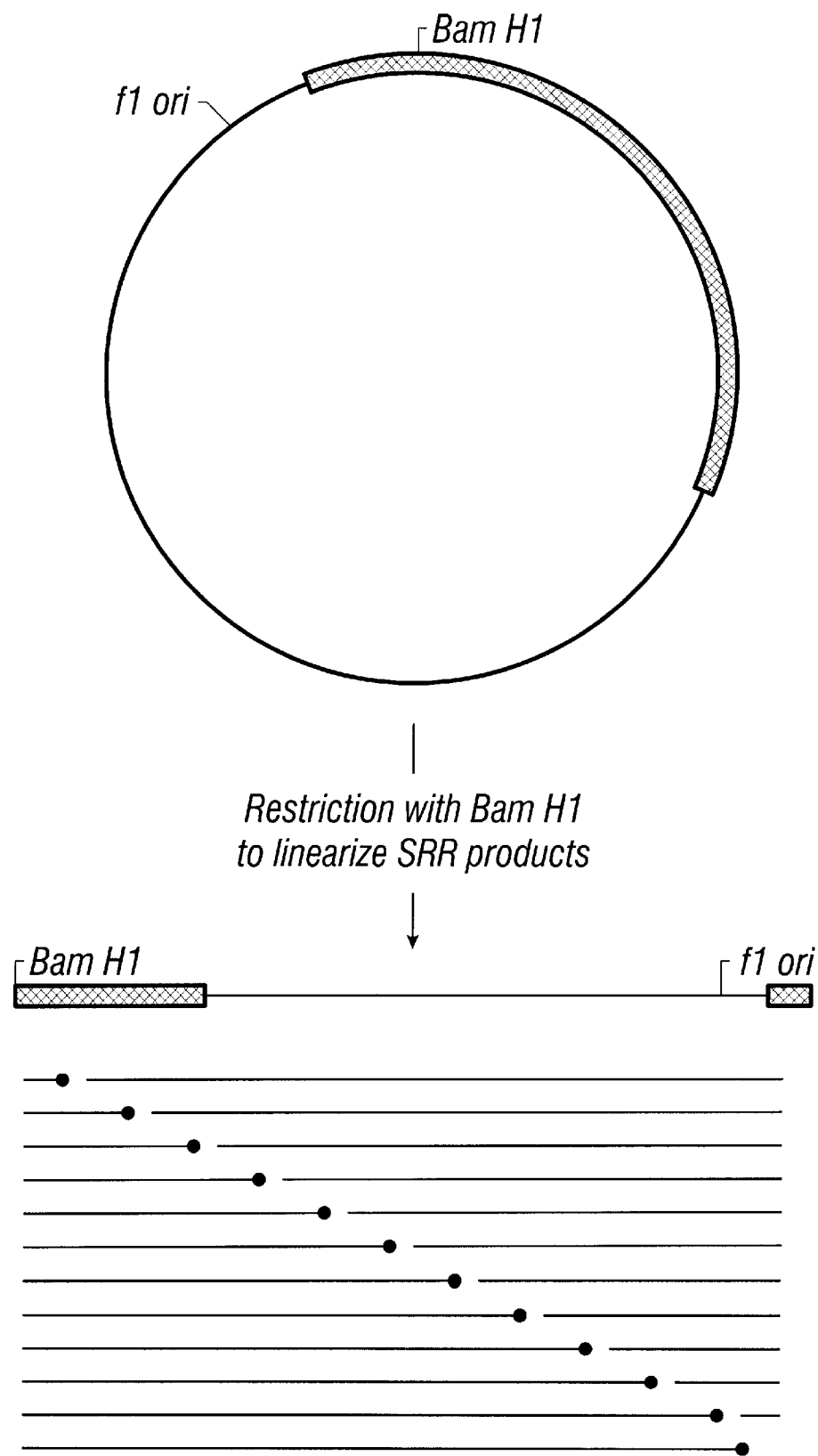
FIG. 5. Schematically shows one embodiment of the strand replacement method of the present invention whereby sequencing can be performed directly on restriction fragments, without size fractionation. The top panel shows a plasmid having a single BamHI restriction endonuclease site. Strand replacement reaction is initiated at the fl origin of replication (fl ori), and proceeds through the DNA to be sequenced (bold line). The products of the strand replacement reaction are cut with BamHI, which produces a population of fragments with the strand replacement reactions terminated at different positions (closed circles; bottom panel).

In certain cases, expected to occur often in DNA molecules less than about 5 kb in length, a number of restriction enzymes can be found that will cleave the DNA only once within the unknown sequence. In these cases only one restriction fragment will be formed, and sequencing can be performed directly, without size fractionation. This is illustrated in FIG. 5 for a circular plasmid having an insert containing a single Bamr H1 site. Strand replacement begins at the nick site (fl origin site) and proceeds clockwise. By making nicks in different strands, the sequences adjacent to the restriction sites in both directions can be determined. A double stranded strand replacement product can be subjected to digestions with different restriction enzymes. The products from each restriction digestion can be subjected to sequencing reactions to get sequence information from many sites. For example, after linearization with the restriction enzyme Bam H1, the products can be sequenced starting from the Bam H1 site. This method will also work with linear DNA as long as the end of the DNA behind the strand replacement polymerization is long enough (e.g. >1000 bp), such that the synthesized strand containing the sequences of the fl origin is too long to interfere with the bands produced adjacent to the restriction site.

d. Bidirectional Sequencing Adjacent To A Series Of Restriction Sites

In another embodiment, both sides of a single internal restriction site (clockwise and counterclockwise) are sequenced in a covalently-closed circular DNA molecule. In the presence of ethidium bromide (Kovacs et al., 1984) many restriction endonucleases are able to nick DNA at the recognition site. After the initial nick, no further digestion takes place, so that most molecules have a single nick. Half of the molecules will have a nick in the top strand, and the other half a nick in the bottom strand. After removal of ethidium bromide using standard techniques, the mixed population of DNA molecules is subjected to the strand replacement sequencing reaction of the present invention. Those molecules nicked in the top strand will synthesize products in a clockwise direction; those nicked in the bottom strand will synthesize products in the counterclockwise direction. Those rare molecules that are not nicked or have undergone double-strand scission will not initiate the SR reaction. By controlling the reaction time the strand replacement sequencing reaction will be allowed to proceed long enough to progress about twice the critical length for sequencing by gel electrophoresis (~2,000 bp). Some of the strands will terminate at ddNTP sites and others will terminate at ~2,000 bp (for example).

Alternatively after removing the ethidium bromide, the template DNA can be restricted at a rare restriction site located far from the insert that is being sequenced (the external restriction site). After the SR reaction, the products are cleaved again with the first restriction site, which cuts at the internal site, and also at the external site (if not cut previously). Now the sample consists of a mixture of two double-stranded restriction fragments, one carrying the strand replacement products synthesized clockwise from the internal restriction site and the second carrying the strand replacement products synthesized counterclockwise from the same internal restriction site. In principle, these fragments can be separated by molecular weight; however, because it is a binary mixture, any of a number of simpler, affinity techniques could be used. For example, the vector sequence to the left of the DNA insert can contain a sequence that will bind to a special triplex forming oligonucleotide or other sequence-specific DNA binding molecule (Hacia et al., 1994; Pilch et al., 1996; Trauger et al., 1996) that contains a chemical tag that can be affinity immobilized. The chemical tag allows for immobilization of the DNA binding molecule and attached DNA (in this case, the double-stranded restriction fragment to the left of the restriction site). In the case of a specific tag, such as a triplex-forming biotinylated oligonucleotide, one of the two double-stranded DNA molecules can be immobilized on a streptavidin-coated surface (e.g. beads). The free DNA can be loaded on the one lane of a sequencing gel and analyzed to sequence the bases located clockwise from the internal restriction site; the immobilizing surface (e.g. beads) can be washed to remove unbound DNA, denatured, and loaded on a different lane of the sequencing gel. Such separation has been used previously to separate strands of denatured PCR™-amplified DNA before conventional ddNTP sequencing reactions (Hultman et al., 1990; Lagerqvist et al., 1994).

e. Sequencing Of PCR™ Products

Figure 7A:
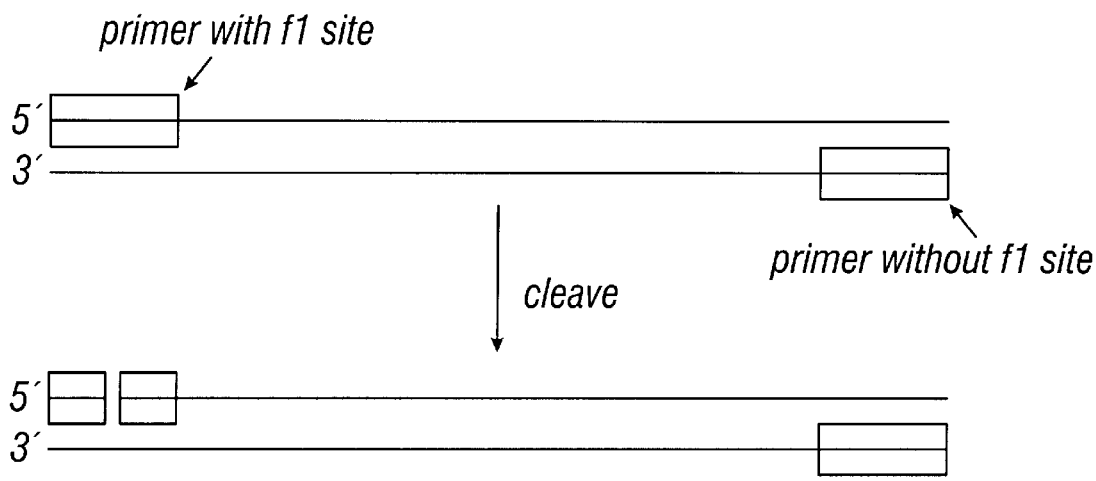
FIG. 7A, FIG. 7B, FIG. 7C, FIG. 7D and FIG. 7E. Schematically shows different embodiment of the strand replacement method of the present invention for sequencing PCR™ products.
Figure 7B:
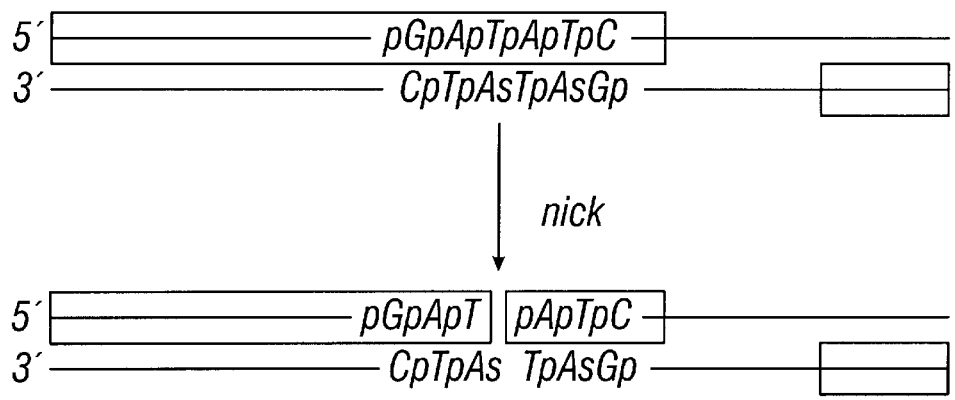
Figure 7C:
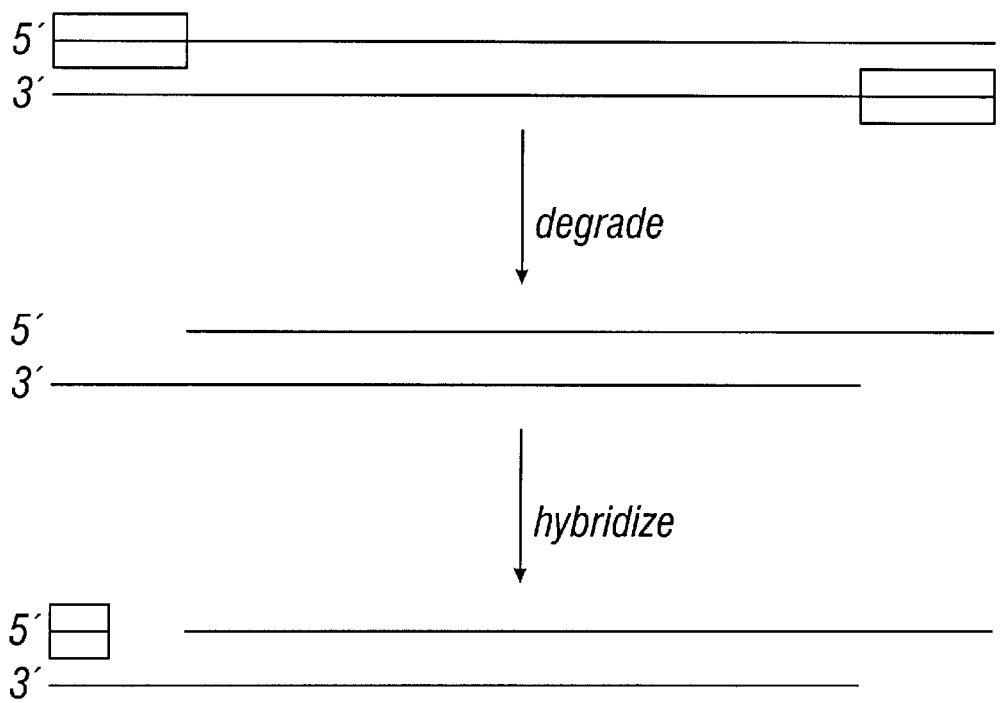
Figure 7D:
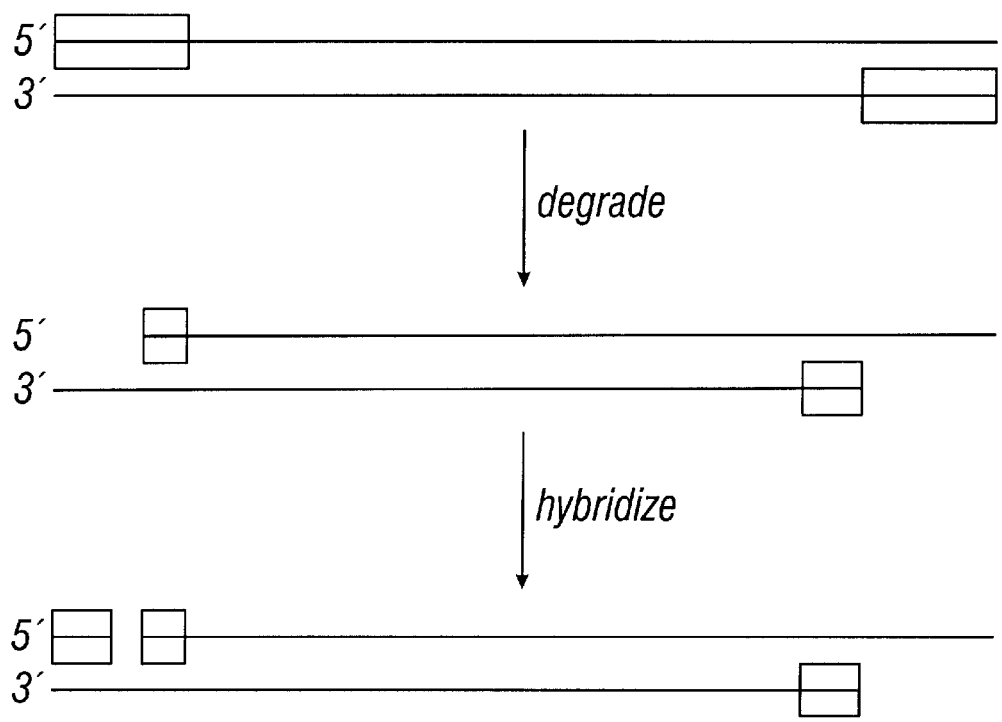
Figure 7E:
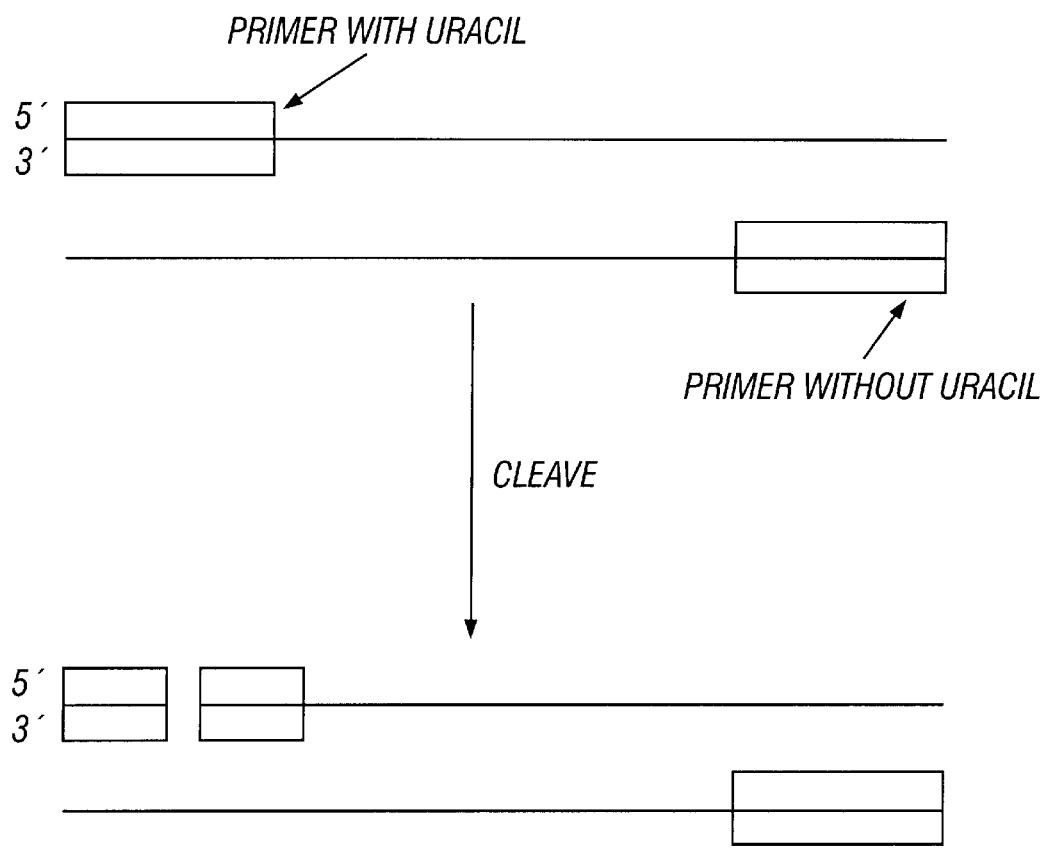

PCR™ products can be subjected to the strand replacement method of the present invention. In one embodiment, PCR™ products are sequenced by incorporating special oligonucleotide primers for the PCR™ reaction that can be later processed to form a nick. For example, one of the two PCR™ primers can contain an fl origin core sequence which can be cleaved with gpII (FIG. 7A). Alternatively, the PCR™ products can be subjected to treatments to degrade a few nucleotides from the 5' termini [e.g., by use of T7 gene 6 exonuclease (FIG. 7C), or by cleavage of dUTP present in one of the primers (FIG. 7D)]. Subsequent hybridization of an oligonucleotide primer under non-denaturing conditions to the 3' tail of the PCR™ products will produce the priming site necessary for initiation of strand replacement.

Alternatively, an asymmetric PCR™ reaction can incorporate a phosphorothiolated nucleotide analog into one of the two DNA strands. Certain restriction enzymes are known to nick the normal strand of hemiphosphorothiolated DNA (Olsen et al., 1990), schematically represented in FIG. 7B.

f. Microchip Oligonucleotide Array Sequencing

Array sequencing involves hybridizing labeled unknown DNA to an array of oligonucleotides with different sequences. If a particular sequence (e.g., TTAGGG) occurs within the DNA, the array position having the CCCTAA oligonucleotide hybridizes to the unknown DNA, thereby immobilizing the label at a specific array position. By examining which array positions become labeled, a computer is able to reconstruct the sequence of the unknown DNA.

Figure 9:
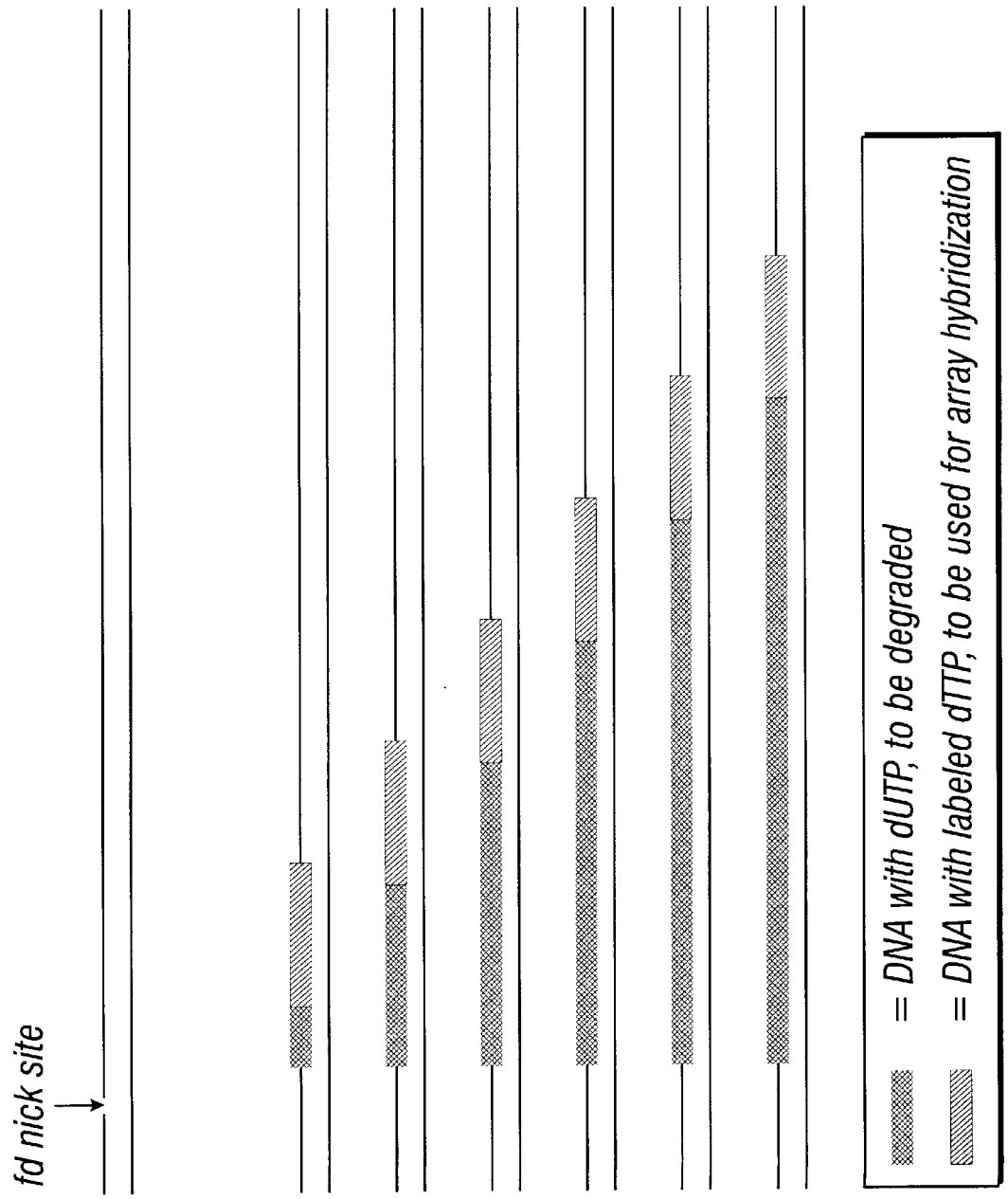
FIG. 9. Schematically shows one embodiment of the strand replacement method of the present invention for producing groups of short DNA molecules at different distances from an initiation site. The top panel shows a DNA molecule having a single fd nick site. The bottom panel shows the products of a strand replacement reaction incorporating dUTP for different amounts of time, followed by incorporation of labeled dTTP for a short, fixed time. The DNA containing dUTP, which can be degraded, is shown as a cross-hatched box, and the DNA containing labeled dTTP, that is stable to degradation and can be used, for example, in array hybridization, is shown as a solid box.

The strand replacement method of the present invention provides a method for overcoming this limitation by producing groups of short DNA molecules at different distances from the gp II nick site, as shown in FIG. 9. In this figure, one embodiment of the method is shown for creating DNA different distances from the nick site. In this example, dUTP, dATP, dGTP, and dCTP are incorporated during an initial, variable period of the strand replacement reaction, followed by a fixed-time pulse of incorporation of dTTP, dATP, dGTP, and dCTP. The dTTP preferably is labeled (e.g., a radioactive label, a fluorescent label, or other suitable label). The incorporation of dUTP is done for variable times, whereas incorporation of dTTP is for a constant time, designed to allow synthesis of a stable oligonucleotide short enough to be used for oligonucleotide array sequencing located specific distances from the fl nick site. After the strand replacement reaction, the dU bases are destroyed with deoxyribouracil glycosylase and heat, leaving the different samples of short, labeled nucleic acid bases to be sequenced on the microchip oligonucleotide arrays. This specific embodiment can be generalized to sequence DNA different distances from any strand replacement initiation site.

2. Primer Extension From Gap or terminal Single-Stranded Region

In certain embodiments of the invention, an oligonucleotide primer can be used to provide the free 3' hydroxyl group to initiate the strand replacement reactions. The primers can be annealed to gaps formed in the nucleic acid, as described in detail herein, or to single-stranded regions at the end of the nucleic acid molecule. These single-stranded regions can be either naturally occurring, for example as found in telomeres, or created, preferably enzymatically, for example through the use of Bal 31 and T7 gene 6 exonuclease.

3. Ligation-Mediated Initiation

Figure 6:
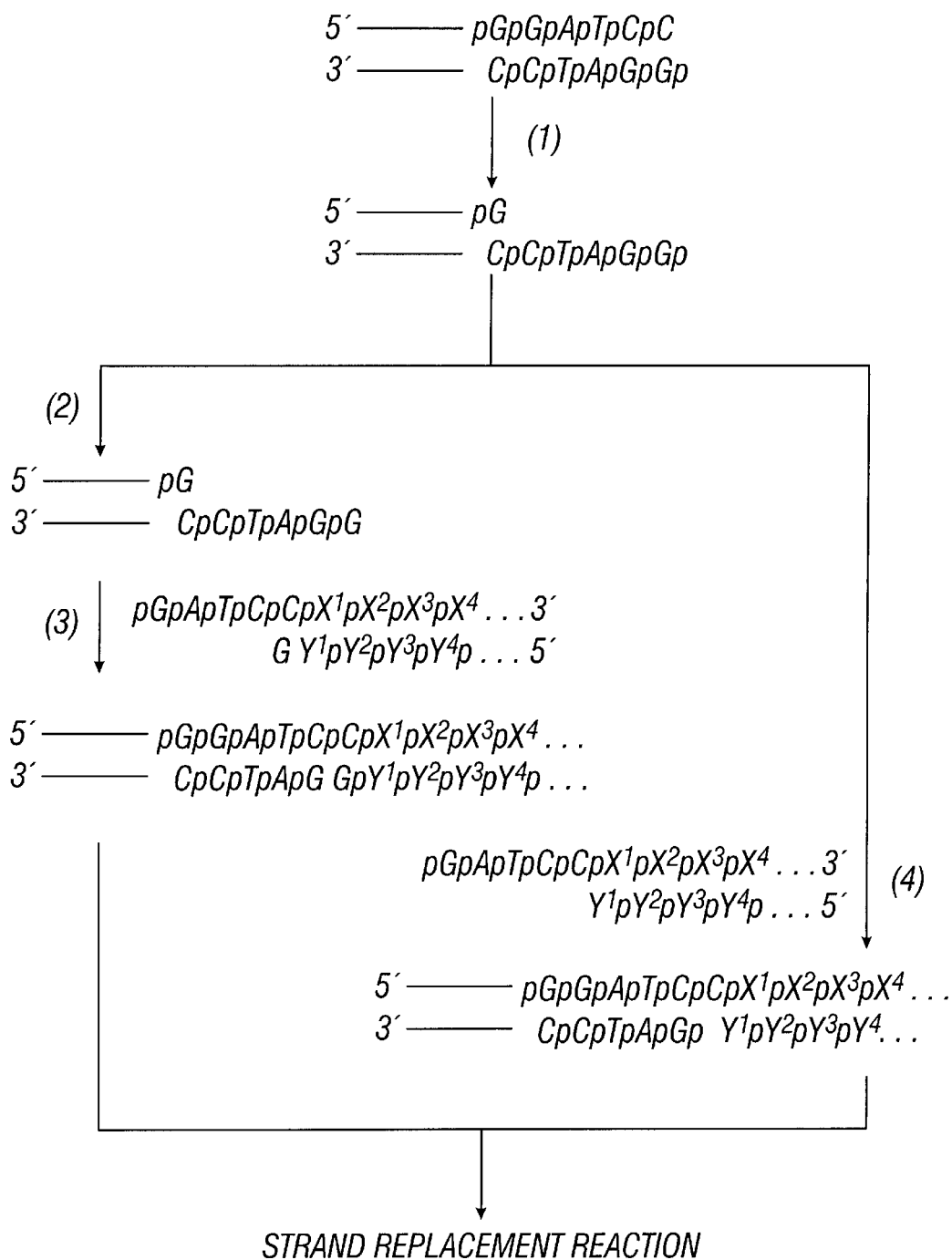
FIG. 6. Schematically shows two embodiments of the ligation-mediated method of the present invention for initiation of strand replacement DNA sequencing. A DNA segment containing a EcoRI restriction endonuclease site is cut with EcoRI (1), which produces a fragment with a 5' extension. Shown are two ways this fragment can be used to produce an initiation site for a strand replacement reaction. The fragment can be treated with phosphatase to remove the terminal 5' phosphate (2), and then annealed to an adaptor (3) having an EcoRI 5' overhang. The annealed product has a single-stranded nick, corresponding to the missing phosphate group removed by the phosphatase reaction. Alternatively, the original fragment can be annealed with an adaptor having an extra base in the 5' overhang (4), producing a product having a one-base nick. Both nicked products can then be used in a strand replacement reaction.

Linear restriction fragments can be produced by restriction of cloned or PCR™ amplified DNA (FIG. 6, step 1). For illustrative purposes, the DNA in FIG. 6 has been cleaved with Bam HI at one end. To create an initiation point for strand replacement at one end of such a molecule, a special double-stranded adaptor DNA molecule is ligated to one end of the restriction fragment using a ligase (including, but not limited to *E. coli* ligase or T4 ligase) in such a fashion that a nick or one base gap is formed. This is achieved, for example, by dephosphorylating the 5' ends of the restriction fragment (for example with calf intestinal phosphatase or shrimp alkaline phosphatase) before the ligation reaction (FIG. 6, steps 2 and 3), or by using a double-stranded oligonucleotide (FIG. 6, step 4) designed with a 3' end one base shorter than required for ligation. The 3' OH within the resulting nick or gap serves as the initiation point for the strand replacement reaction. Sequence information can be gained by analysis of the strand replacement products starting from one terminus or the other, using different nicking strategies for the two ends. In addition, cleavage with different restriction enzymes will allow sequencing to be "read" adjacent to different restriction sites.

B. Random Break Incorporation Sequencing

Random Break Incorporation (RBI) sequencing is distinguished from the Sanger method and all variations thereof by the fact that DNA synthesis is initiated at random sites and terminated after addition of only a few bases (in many cases the first base).

The initiation of sequencing reactions at random breaks enables an entirely new concept of DNA sequence determination and analysis to be achieved. This new method involves determining and analyzing the sequence of dinucleotides, trinucleotides, and longer combinations of bases along DNA. Two distinct methods of determining multiple-base sequences are disclosed, the first method involving one or more steps of direct polymerization of nucleotides from the site of random breaks, and the second method involving an initial degradation step followed by one of more polymerization steps. These two methods use different reagents and reaction steps, yet achieve the same goal of determining the positions of multiple-base sequences along the DNA. Although the advantages of the multiple-base sequencing techniques are discussed in terms of dinucleotide sequencing, similar advantages are also found with trinucleotide, tetranucleotide, and longer nucleotide sequencing.

Dinucleotide sequencing is the determination of the positions of each occurrence of a specific nucleotide pair (e.g., GC) in a DNA molecule. This is achieved by terminating the DNA strands with labeled specific nucleotide pairs. The dinucleotides are "read" after electrophoresis, mass spectrometry, or other size separation step, in the same way that the occurrence of single bases is "read" in the conventional Sanger or Maxim-Gilbert methods of sequencing. Dinucleotide sequencing is very powerful because it increases the length of DNA that can be sequenced in a single gel lane, and increases the accuracy of determination of the sequence. The length of DNA that can be sequenced in a single gel lane is determined by the maximum size of DNA for which successive bands of the sequencing ladder can be resolved.

Successive bands on a single base sequencing gel can be separated by as little as one base. The current practical limits of gel electrophoresis restrict single-base resolution to DNA less than 500–1500 nucleotides, depending upon the type of electrophoresis apparatus used. In contrast, the positions of bands in a dinucleotide ladder can be no closer than two nucleotides. Therefore dinucleotides can be resolved in molecules up to 1000–3000 nucleotides. In practice, the average distance between each band in the dinucleotide sequencing ladder is 16 bases, which is 4 times greater than the average distance between bands in the single base sequencing ladder. This ability to read longer sequences using dinucleotide terminations greatly advances the progress and reduces the cost of DNA sequencing. Dinucleotide sequencing also increases the accuracy of sequencing by reading every base twice. For example, when the sequence AGC is present on the DNA, the central guanine will be read twice, once as the dinucleotide AG and once as the dinucleotide GC.

In certain aspects of this method, dideoxyribonucleotides are not necessary for termination. The basic steps of RBI sequencing of DNA can be summarized as follows:

Preparation of pools of double-stranded DNA molecules with identical sequence. This is achieved by direct isolation of the DNA, by cloning of DNA fragments in a suitable vector such as a virus, prokaryotic cell, or eukaryotic cell, or by amplification using primer extension, strand displacement, or polymerase chain reaction (PCR). An important feature of the DNA is that at least one 5' terminus (or site near the 5' end) is "tagged" with a chemical group for detection or immobilizing the DNA.

Single- or double-stranded breakage of the DNA to create infrequent double- or single-standarded ends at random or substantially random locations. Degradation can be enzymatic (e.g., DNase I), chemical (e.g., hydroxyl radicals), or physical (e.g., hydrodynamic shear, freezing, or radiation). The defects must terminate or be made to terminate with a free 3' hydroxyl end on the product strand, opposed to a complementary template strand. The use of randomly-located priming sites is a key, unique feature of the inventors' method to sequence DNA. All polymerases studied require 3' ends with hydroxyl groups in order to incorporate new nucleotides. Therefore breaks in the DNA that do not originally contain 3' OH groups have to be conditioned to possess 3' OH groups before strand elongation can be done. One method to condition the 3' end is to incubate the DNA in the presence of a 3' exonuclease such as *E. coli* exonuclease III. This invention also contemplates the discovery or engineering of DNA polymerases able to remove nucleotides that do not have 3' OH groups from the 3' ends of DNA strands.

Addition of one or more nucleotide bases to the 3'OH end the product strand, whereby the base(s) added is (are) complementary to the opposed base(s) on the template strand. The base addition is catalyzed using a DNA polymerase capable of adding complementary bases using nucleotide triphosphates added to the reaction mixture. If a single dideoxyribonucleotide base is added, it will be added to 3'OH termini 0 or one times, depending on whether the dideoxyribonucleotide base is complementary to the opposed base on the template strand. If a single deoxyribonucleotide base is added to the reaction, it will be added to the 3'OH termini 0, 1, or more times for as long as the base is complementary to the template strand. As detailed herein, a succession of different complementary deoxyribonucleotide bases can be added by changing the deoxyribonucleotide triphosphates in the reaction buffer. The dideoxyribonucleotide or deoxyribonucleotide terminal bases are "tagged" such that if the 5' end of the primer is tagged for detection, the base added to the 3' termini of the product strands is tagged for immobilization; but if the 5' end of the primer is tagged for immobilization the base added to the 3' termini of the product strands is labeled for detection. When the primer is used for immobilization, several DNA molecules can be simultaneously prepared for sequencing by use of distinguishable immobilization tags.

Separation of the DNA molecules by molecular weight and detection of those fragments that have both tagged 5' ends and tagged 3' ends. After the polymerization reaction some strands will have tagged 5' ends, tagged 3' ends, or both. Those strands with the immobilization tags will be retained on a surface or within a matrix, whereas those strands without the immobilization tags will be removed. The retained strands will be specifically mobilized and separated according to molecular weight by electrophoresis, chromatography, mass spectrometry, or other suitable technique, and identified by virtue of the detection tag. Therefore the only strands identified after size separation are those tagged for both immobilization and detection. If a single dideoxyribonucleotide or deoxyribonucleotide base has been added to the 3' terminus of the product strands then the lengths of the identified DNA fragments (in nucleotides) will give the distance (in nucleotides) of that specific base from one end of the DNA molecule. Combining information about the lengths of the molecules that terminate with adenine, thymine, guanine, and cytosine will give the base sequence of the DNA molecule. These results are similar to the results of the Sanger Sequencing method, and can be called "single-base sequencing." When a succession of different nucleotide bases are added to the 3'OH ends the molecular weights of the detected fragments will represent the positions of specific strings of bases along the DNA (e.g., $A_n T_m Co$, where n is the number of successive A residues, m is the number of successive T residues, and 0 is the number of successive C residues). The results of this approach can be called "multiple-base sequencing."

Random breaks can also be used for sequencing by degradation rather than synthesis at random sites. In this variation, the DNA to be sequenced contains a degradation resistant base, such as an αS dNTP. After random degradation of the DNA, an exonuclease is used to degrade the strand up to the resistant base. This example (called random break degradation sequencing) is discussed further in this disclosure herein below.

The principle of Random Break Incorporation sequencing can be implemented in a number of ways, using different methods for preparing the DNA fragments, degrading the DNA, tagging the DNA, incorporating nucleotides, and separating the products. The inventors will not detail all alternatives to each of the fundamental steps, but will give three main examples designed to achieve single-, double-, and n-base sequencing. In every case the protocols share the common step of priming DNA synthesis at random breaks in the DNA, in contrast to the Sanger method which primes DNA synthesis at unique sites.

1. One Base Sequencing a. Single-base sequencing using single-strand breaks

The strands to be used for sequencing must terminate at a unique site at their 5' ends, and a plurality of base-specific sites at their 3' ends. This can be achieved using multiple strategies. For example, a tag can be incorporated at the 5' end for purposes of detection of the molecule and a different tag incorporated at the 3' end to physically separate the molecules from those that have not been tagged at the 3' ends. Alternatively the separation tag can be placed at the 5' end and detection tag at the 3' end. For purposes of this disclosure the inventors have described physical separation as immobilization on a surface or in a matrix by well-established techniques. In principle other techniques of separation, including but not limited to electrophoresis, chromatography, centrifugation, or enzymatic processing can also be employed.

Figure 15B:
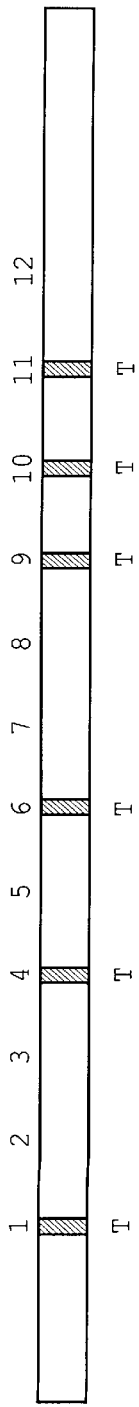
FIG. 15. Schematically sets forth RBI sequencing with detectable primer and biotinylated ddTTP. The top panel shows a PCR™-amplified DNA with a detection tag at the 5' end of primer X (open circle). The numbers show the 12 unknown bases. The next panel shows the population of products of random degradation (nicks shown on upper strand only), with each of the twelve unknown bases being nicked. The next panel represents the products of the random degradation after exposing the 3' hydroxyl group at the damage site. The next panel shows the incorporation of biotinylated ddTTP at positions opposite adenine in the template strand. The next panel shows the immobilization of the biotinylated strands, and removal of the non-biotinylated strands. The bottom panel is a schematic representation of the released biotinylated strands separated by electrophoresis, and detection of the tagged primer. The dark bars represent the position of thymine.

Single-base sequencing employing 5' tags that can be detected and 3' dideoxy nulcleotides with tags that can be immobilized In this first example, the inventors describe the case of detecting the strands with a 5' tag and separation by immobilization of the strands with a 3' tag. The steps of processing the DNA are illustrated in FIG. 15, with the results on sequencing gels shown in FIG. 16.

Preparation of tagged DNA molecules for sequencing

A DNA sequence can be amplified by PCR using two primers, complementary to bases at both ends of the DNA to be sequenced. One of those primers is tagged for detection using one or more fluorescent, radioactive, or chromogenic chemical groups. Detectable primers are available from commercial sources or can be synthesized in individual laboratories. To facilitate later cleavage of the DNA special nucleotide analogs (e.g., dU) can be incorporated into one or both strands during amplification.

Tagged DNA molecules can also be produced from cloned DNA. For example, restriction at a site adjacent to the insert DNA can be followed by radioactive labeling of the 5' terminus using kinase or ligation of a detectable oligonucleotide. Alternatively a site in the vector sequence can be nicked using f1 endonuclease, tagged by incorporation of detectable nucleotides using nick-translation, followed by ligation and recleavage with f1.

Random breakage of DNA to create priming sites for DNA polymerase

Random breaks are introduced into one or both DNA strands using reagents familiar to molecular biologists. For example, DNase I used under different conditions can produce nearly random double-strand or single-strand breaks. These enzymes produce 3'OH groups that can serve as priming sites. Single-strand breaks can also be produced using hydroxyl radicals generated by a number of methods including $Fe^{2+}$/EDTA/$H_2O_2$ or gamma irradiation. The primary products of radical cleavage are randomly-positioned nicks or gaps, usually with 3' phosphate groups. Therefore the DNA must be processed before the sites can be used to prime DNA synthesis. After creation of a low frequency of defects, a suitable phosphatase (e.g., alkaline phosphatase or T4 kinase in the absence of ATP) or a 3' exonuclease (e.g., exo III) is used to create 3' OH groups at the site of the defects. Each of these 3'OH ends constitutes a potential priming site for DNA synthesis. Single-strand breaks can also be made by freezing and thawing DNA, and perhaps by hydrodynamic shear.

Addition of complementary base at the site of the defects

A DNA polymerase without 3' exonuclease activity (e.g., Taq) and a mixture of one or more normal or terminating deoxyribonucleotide triphosphates will be added. FIG. 15 shows the outcome when biotinylated ddTTP is used as the nucleotide triphosphate. All strands having 3' ends opposite adenine in the template strand will be biotinylated, whereas those terminating in adenine, guanine, or cytosine will not contain a 3' biotin. The specificity to the reaction can be optimized, if necessary, by adding non-biotinylated ddATP, ddCTP, and ddGTP to the reaction mix to reduce the probability that the biotinylated ddTTP will be misincorporated at the 3' ends.

Separation of the DNA molecules tagged at the 3' ends

FIG. 15 shows that the reaction contains fragments terminated with biotinylated thymine at the 3' ends, as well as strands without biotinylated bases at the 3' ends. The strands having biotin will be immobilized using streptavidin-coated magnetic particles, beads, or other surface. The low frequency of defects will ensure that most strands will have only a few biotin moieties. The surface will then be washed under conditions that denature the DNA strands but do not release the strands tagged with biotin (e.g., 30 mM NaOH). After all non-immobilized strands of DNA are removed, the immobilized strands can be released by reversing the streptavidin-biotin linkage (e.g., heating in the presence of SDS).

Biotin can be used as a separation tag because of its high affinity for streptavidin. However alternative moieties can be used for separation. For example, digoxigenin can be used because it can be immobilized using specific antibodies, or a sulfhydryl group can be used because it can be immobilized by oxidation with other sulfhydryl groups.

Size-separation and detection of the DNA molecules tagged on both ends

Figure 16A:
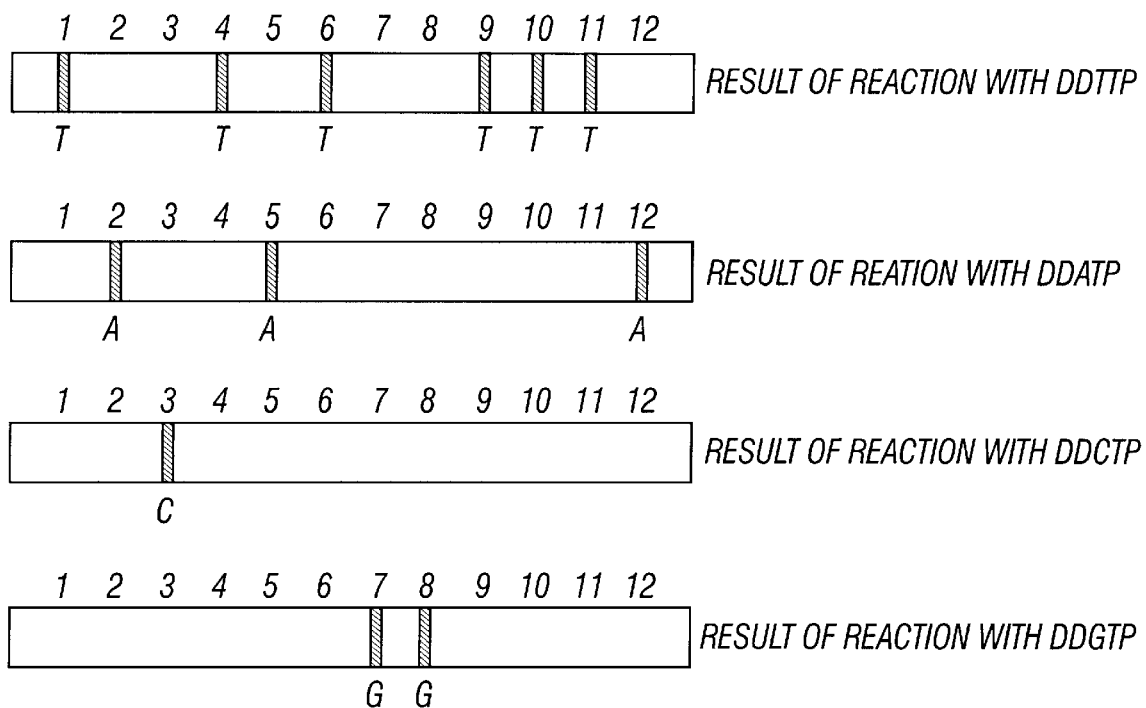
FIG. 16. Schematic depiction of size separation of separate RBI reactions terminated with tagged ddNTPs. The top panel schematically shows the results from the reactions performed as described in FIG. 15 using biotinylated ddTTP, biotinylated ddATP, biotinylated ddCTP and biotinylated ddGTP. The bottom panel shows a schematic representation of the summation of the results from the top panel, showing the complete base sequence.
Figure 16B:
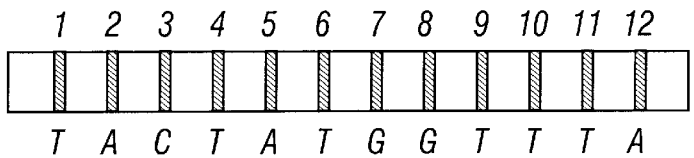

To determine the position of the tagged dideoxythymidine nucleotides along the DNA, the released molecules must be separated according to size (e.g., by electrophoresis on a standard sequencing gel) and the strands having tagged primer DNA at the 5' ends detected on the basis of fluorescence, absorbance, or emission of light, an enzymatic reaction, or detection of radiation. The sequencing ladder produced after incorporation of the ddTTP (FIG. 15) will have bands representing the positions of every thymine in the product strand, analogous to the sequencing ladders found by the Sanger Method. In order to determine the positions of all four bases, four reactions are performed using primers tagged with the same detectable moiety followed by electrophoresis of the products of the four reaction in separate electrophoretic lanes, as shown in FIG. 16. Alternatively the four reactions incorporating the four dideoxynucleotide bases can employ four distinguishable primers (e.g., four different fluorescent dyes) and the products combined into a single gel lane followed by differential detection of the products of the four reactions. Combining the information in all four lanes or from the differentially detected bands in one lane, the exact base sequence will be determined, as shown in FIG. 16.

Figure 17A:
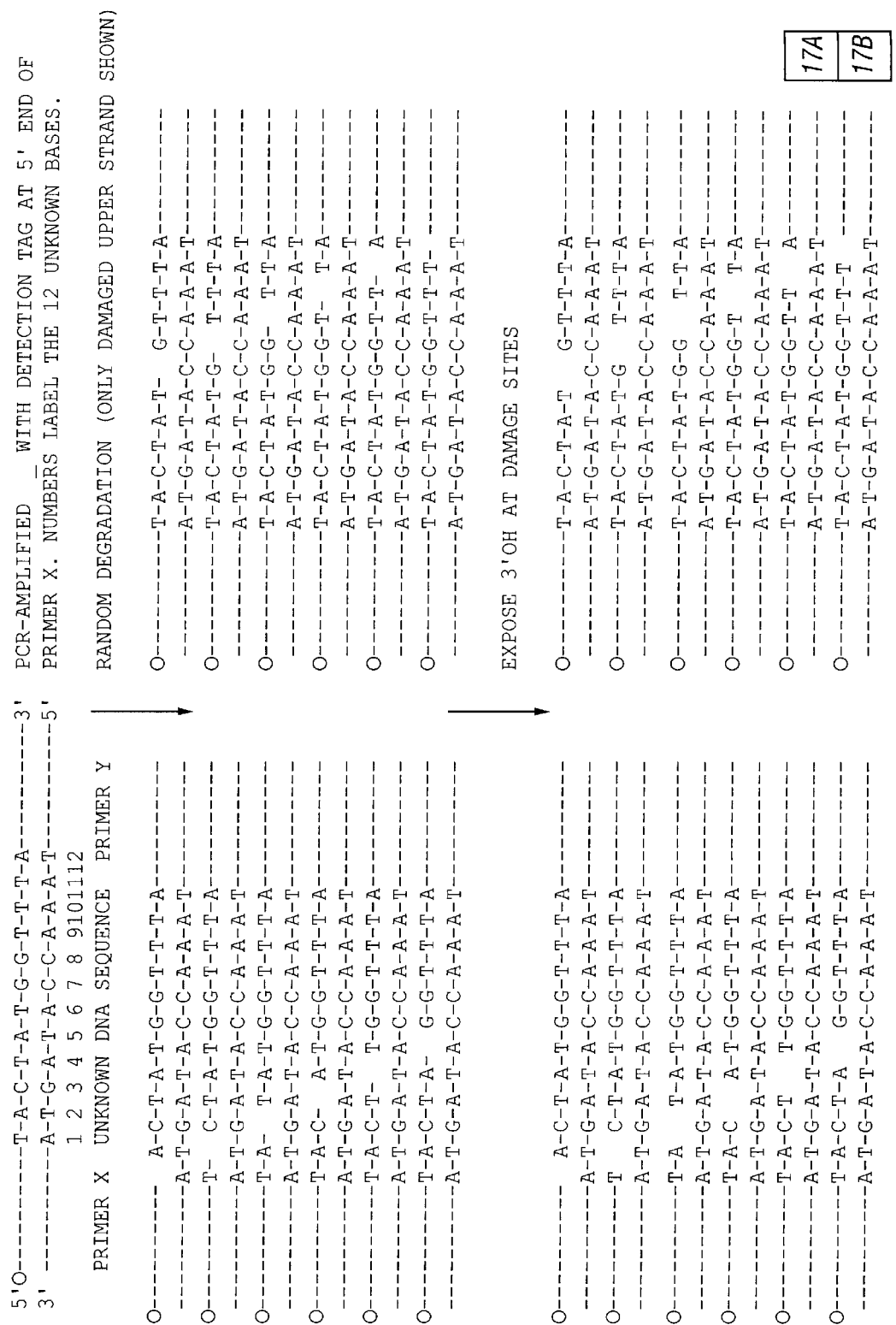
FIG. 17. Schematically sets forth RBI with detectable primer and biotinylated dTTP. The top panel shows a PCR™-amplified DNA with a detection tag at the 5' end of primer X (open circle). The numbers show the 12 unknown bases. The next panel shows the population of products of random degradation (nicks shown on upper strand only), with each of the twelve unknown bases being nicked. The next panel represents the products of the random degradation after exposing the 3' hydroxyl group at the damage site. The next panel shows the incorporation of biotinylated dTTP at positions opposite adenine in the template strand. The next panel shows the immobilization of the biotinylated strands, and removal of the non-biotinylated strands. The bottom panel is a schematic representation of the released biotinylated strands separated by electrophoresis, and detection of the tagged primer. The dark bars represent the position of terminal thymine.
Figure 18A:
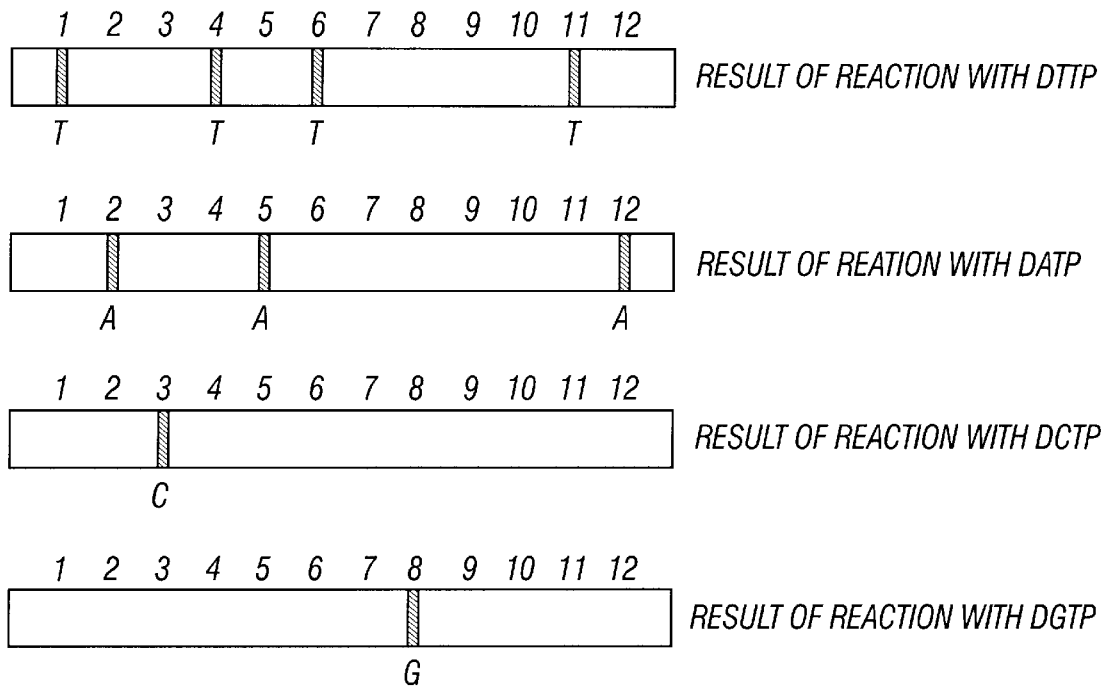
FIG. 18. Schematic depiction of size separation of separate RBI reactions terminated with tagged dNTP. The top panel schematically shows the results from the reactions performed as described in FIG. 17 using biotinylated dTTP, biotinylated dATP, biotinylated dCTP and biotinylated dGTP. The bottom panel shows a schematic representation of the summation of the results from the top panel, showing the complete base sequence. The positions of the bases in parentheses are inferred.
Figure 18B:
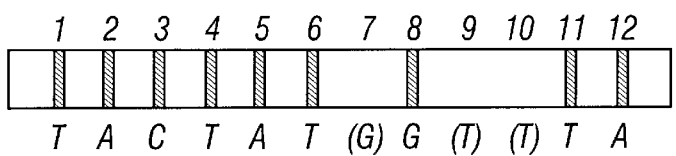

Single-base sequencing employing 5' tags that can be detected and 3' deoxyribonucleotides with tags that can be immobilized The necessary 3' tags can also consist of normal deoxyribonucleotides, as shown in FIG. 17 and FIG. 18. All steps are the same as explained herein above, with the exception that the each polymerization reaction is done in the presence of a single normal deoxyribonucleotide. FIG. 17 shows the case where tagged dTTP is used for the reaction. The sequencing ladder (shown in FIG. 18) will have bands representing the positions of the ends of every succession of one or more thymines in the product strand, similar to the sequencing ladders found by the Sanger Method, except having gaps wherever there is a string of more than one thymine. By combining information from reactions terminated with dTTP, dCTP, dGTP, and dATP, the identity of bases in the gaps of the electropherograms will be the same as that of the base at the 3' end of the gap. For example if guanine is present at base positions 7–8, there will be a guanine band at position 8 adjacent to a gap at position 7. A guanine at position 7 is inferred from the lack of a thymine, cytosine, or adenine band at that position and the presence of a guanine at position 8. Thus the complete base sequence can be determined.

Figure 19A:
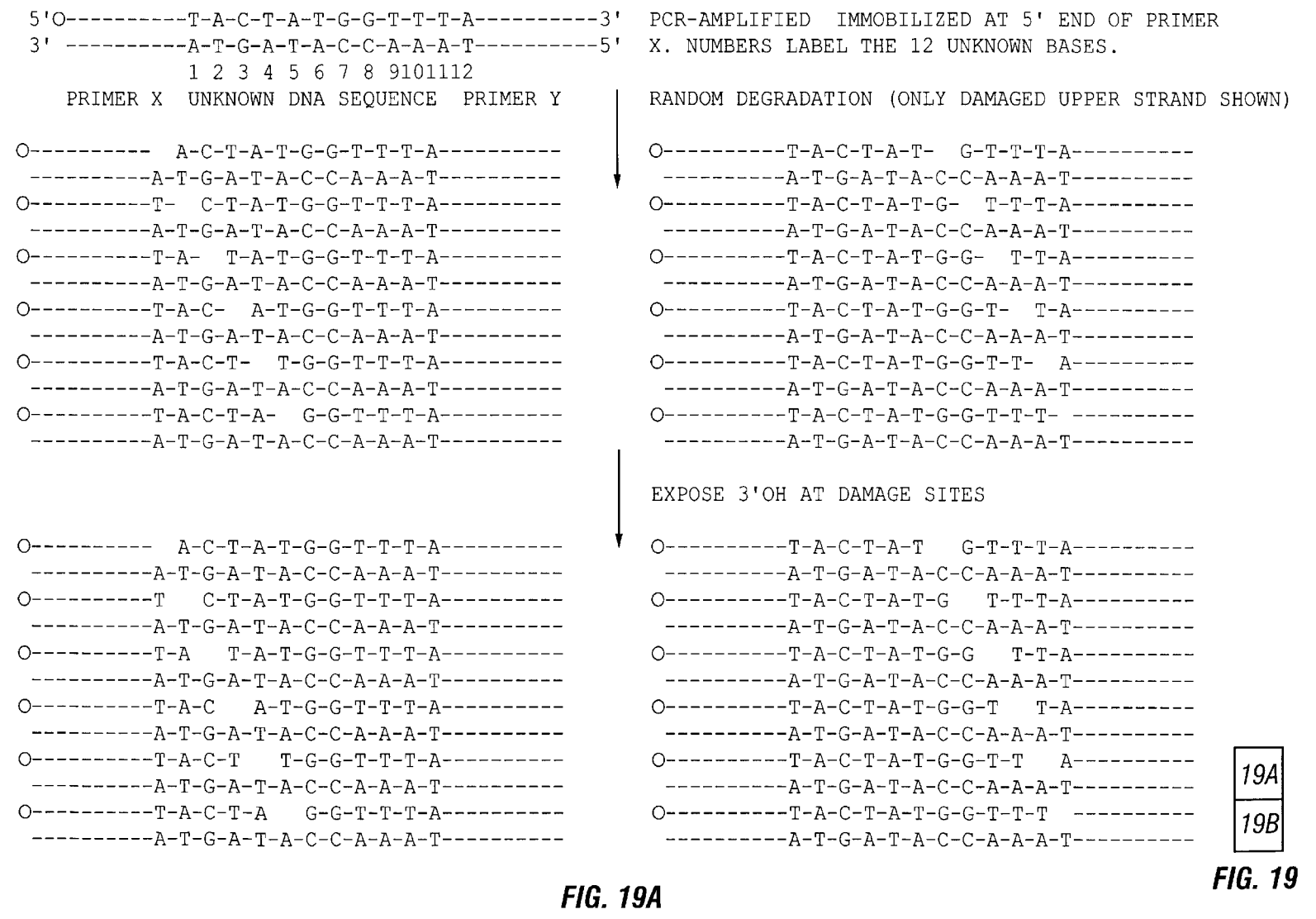
Figure 20A:
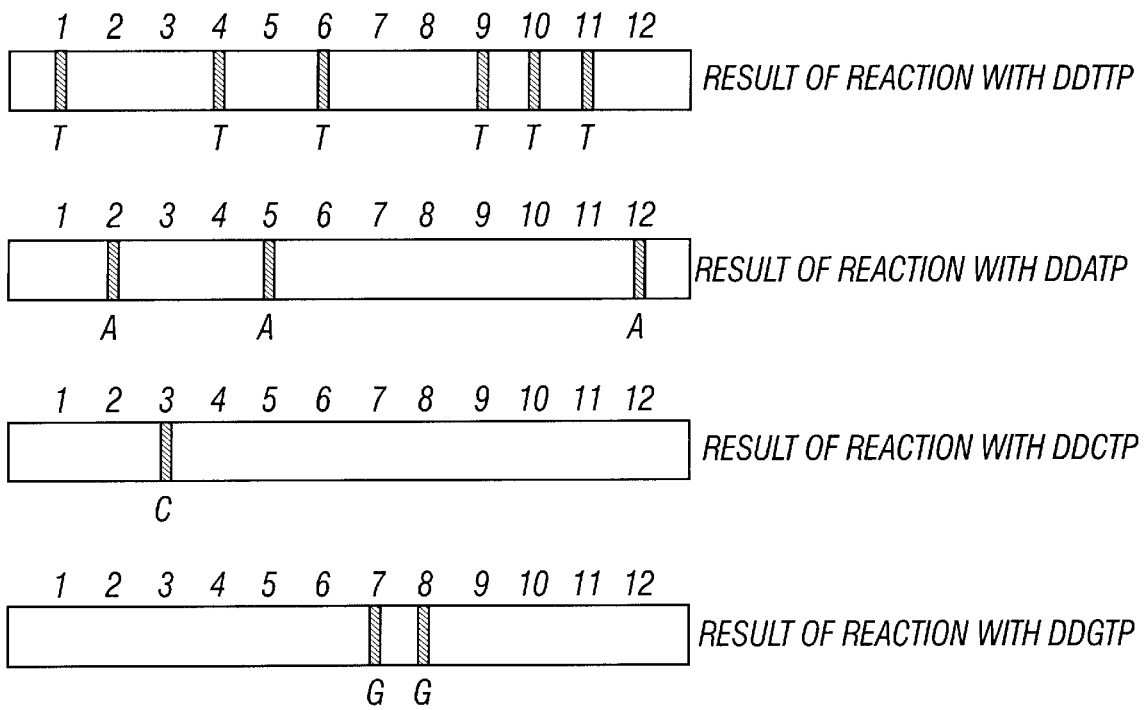
FIG. 20. Schematic depiction of size separation of separate RBI reactions terminated with detectable tagged ddNTP. The top panel schematically shows the results from the reactions performed as described in FIG. 19 using tagged ddTTP, tagged ddATP, tagged ddCTP and tagged ddGTP. The bottom panel shows a schematic representation of the summation of the results from the top panel, showing the complete base sequence.
Figure 20B:
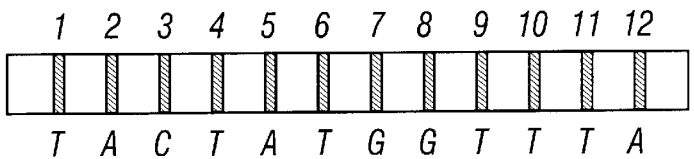

Single-base sequencing employing 5' tags for separation and 3' tags for detection The role of the tags at the 3' and 5' ends can be reversed, which results in less flexibility in design of the tag for detection, but greater flexibility in the tag used for separation. In certain aspects of the present invention, 5' immobilization tags and 3' detection labels are preferred. FIG. 19 shows the situation when the 3' end of the product DNA has been labeled for detection by incorporation of a detectable base analog and the primer has been tagged with biotin for immobilization. In this case the DNA molecules are first immobilized via the biotin or other immobilization moiety at the 5' end of the product strand. Other moieties can be used for immobilization, such as digoxigenin, SH groups, or triplex-forming sequences incorporated into a PCR primer or incorporated into the 5' end of the product strand. The procedures for degrading the DNA, priming synthesis, and size separation have been described herein. Subsequently the DNA is denatured and all the non-biotinylated strands removed by washing. The strands containing the tagged primer can be specifically released using conditions necessary to reverse the biotin-streptavidin bond or by cleaving the primer at an internal site by enzymatic or chemical means. For example, if dUTP has been incorporated into the 5' end of the molecules it can be degraded using uracil glycosylase in combination with enzymes such as endonuclease IV or endonuclease V, base treatment or heat, preferably endonuclease V. Alternatively, if a ribonucleotide is incorporated into a specific location in the primer, cleavage can be effected by raising the pH. Also, a restriction endonuclease recognition site can be engineered into the primer, serving as a substrate to form a break. The released strands will be separated on the basis of molecular weight. If labeled ddTTP has been incorporated by DNA polymerase, then the ladder of fragment lengths will correspond to the positions of every thymine along the product DNA strand. Four such ladders can be produced from four separate reactions with each the four different ddNTPs, as shown in FIG. 20. Combining the information in all four ladders will completely determine the base sequence of the DNA. Alternatively if the polymerization reaction has been performed with four ddNTPs with distinguishable labels (as a combined reaction or as four separate reactions) then the sequence of all four bases can be determined by distinguishing the different labels within a single ladder. Of course sequencing can also be done by incorporation of deoxyribonucleotides at the 3' ends, as shown in FIG. 17 and FIG. 18.

b. Single-base sequencing at random double-strand breaks

All these approaches can be performed on DNA having double-strand breaks by using a DNA polymerase with "proofreading" 3' exonuclease activity, such as T4 DNA polymerase or *E. coli* Klenow fragment. After breakage the DNA might have a very short 3' overhang, 5' overhang, blunt, or a mixture of terminal structures. Any of these ends will serve as substrate for the proofreading DNA polymerase. If a specific tagged ddNTP and the three remaining, untagged dNTPs are added the polymerase will add the dideoxyribonucleotide base at the first complementary position adjacent to the break. The base-specific tag can then be used for sequencing as proposed herein. If, instead, four ddNTPs with distinguishable tags are simultaneously added to the reaction, the polymerase will incorporate all four at complementary terminal positions.

c. Sequencing starting from base-specific single-strand breaks

It is not necessary to break the DNA at totally random sites. For instance, if a cleavage-sensitive base analog is incorporated into one or both DNA strands during synthesis these base positions can later be cleaved. For example, if a small fraction of the thymines are replaced by deoxyribouridines during PCR amplification, those sites can be converted to one base gaps by the concerted action of dU glycosylase and endonuclease V. Separation of the DNA according to molecular weight will give the sizes of all DNA molecules terminated before thymine. Addition of a polymerase and ddTTP or dTTP will tag the thymine-containing sites. To label the DNA at sites containing any of the other three bases a combination of three normal dNTPs and one ddNTP can be used. For instance, to label the DNA at guanine, polymerase plus dTTP, dATP, dCTP, and ddGTP can be added.

2. Two Base Sequencing

This technique allows the display of all positions of a specific doublet of bases. Determination of the positions of the 12 possible doublets with non-identical bases will give sufficient information to determine the sequence of every base. As above, the 5' ends can be tagged for immobilization or detection, and the 3' terminal bases can be tagged for detection or immobilization, respectively. The only step different from those presented for single-base sequencing is the polymerization step, which must achieve the sequential addition of two bases. The method for doing this is shown in FIG. 21 for the determination of the positions of the doublet TA. In this example the DNA is assumed to be immobilized via a tag on the 5' end of the PCR primer strand and detected via a tag incorporated onto the 3' end of the product strand. In principle, the positions of the tags for immobilization and detection can be interchanged.

The DNA is first isolated, immobilized, and randomly degraded as outlined above. Next, the immobilized DNA is incubated in the presence of DNA polymerase and the dideoxyribonucleotides ddATP, ddGTP, and ddCTP. This will block every 3'OH end that incorporates any of those bases (i.e. those opposite T, C, or G in the template strand). However, all ends opposite A in the template strand will remain unblocked, that is still available to prime DNA synthesis. After removal of the ddNTPs by washing, dTTP and polymerase are added to the immobilized DNA in order to add one or more thymidines to the unblocked 3'OH ends opposite one or more adenines on the template strand. One such cycle of blocking the ends opposite three of the bases and incorporating one or more nucleotides opposite the fourth base is called a "walk," in this case a "T-walk," because thymine is added to the free 3'OH ends. The unincorporated dTTP is then removed by washing, and polymerization continued with DNA polymerase and ddATP tagged for detection. The tagged adenine dideoxyribonucleotide will only be incorporated at the unblocked 3'OH ends opposite thymidine on the template strand. This second step is therefore called an "A-termination." The samples are then subjected to conditions that denature the DNA and washed to remove all fragments that are not immobilized via the 5' tags. Subsequently the 5' tagged strands are released by reversing the link used to immobilize the 5' tagged DNA and separated according to size by electrophoresis or other suitable method. Detection of all fragments with the 3' tags will produce a ladder of fragment lengths representing all positions of the TA doublet, as shown in FIG. 21.

Figure 22A:
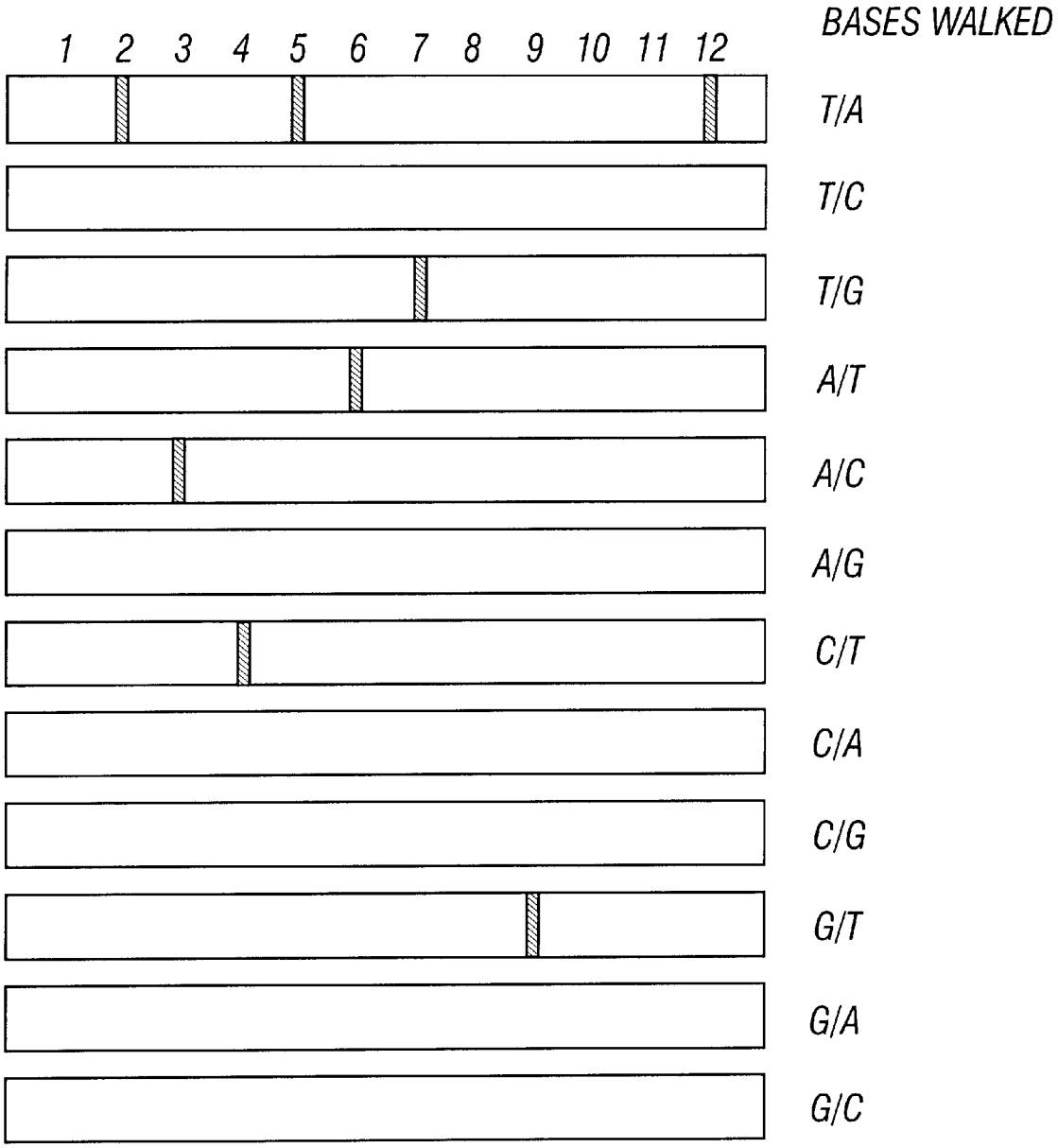
FIG. 22. Schematic depiction of size separation results from twelve 2-base walks put together in complete sequence. The top panel schematically shows the results from the reactions performed as described in FIG. 21 using a T/A walk, a T/C walk, a T/G walk, a A/T walk, a A/C walk, a A/G walk, a C/T walk, a C/A walk, a C/G walk, a G/T walk, a G/A walk, and a G/C walk. The bottom panel shows a schematic representation of the summation of the results from the top panel, showing the complete base sequence. The inferred bases are shown in parentheses.
Figure 22B:
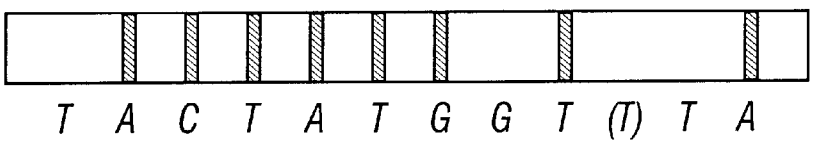

This technique can be used to map the positions of known important doublets such as CG in order to localize CG islands that precede many genes, to locate and measure the length of repetitive DNA tracts (e.g., doublet and triplet repeats involved with genetic diseases), or to sequence DNA. In order to determine the complete DNA sequence the information from all 12 possible hetero-nucleotide doublets can be combined to determine the position of each (as shown in FIG. 22). The sequence of the DNA in regions where homo-nucleotide strings (e.g., AAA) are present can be inferred from the nature of the doublets adjacent to the gaps. Double-base sequencing has advantages over single-base sequencing in that: 1) the sequence is determined with two-fold redundancy, increasing the accuracy of base assignments, and 2) the base sequence can be determined for longer pieces of DNA, because the bands present in the electropherograms are separated by 2 or more nucleotides and thus can be distinguished over a wider range in molecular size than if single-base resolution is required. Thus the "read-length" of the DNA sequencing gels should be significantly longer than possible with single-base sequencing.

Doublet sequencing requires the use of only eight polymerization solutions, each containing DNA polymerase, but differing in the nucleotide triphosphates.

3. Three Base Sequencing and N-Base Sequencing

Figure 23B:
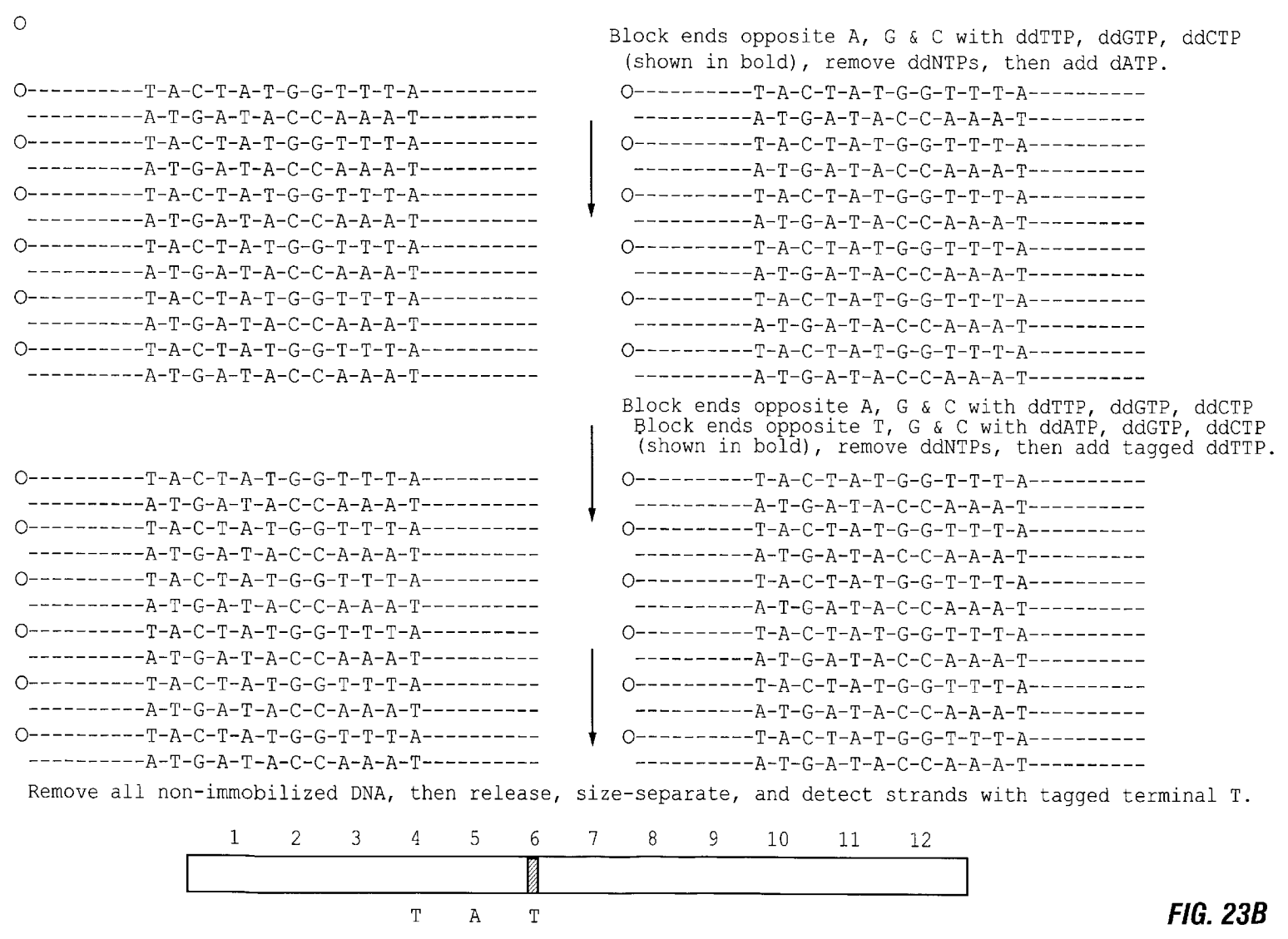

The base walking method described in section 1, c can be extended to determine the location of any succession of bases. For example, a succession of three bases can be symbolized by the string $X_aY_bZ_c$, where X, Y, and Z are types of bases with the properties that X is a different base than Y, Y is a different base than Z, and a, b, and c, are the number of sequential bases of the type X, Y, and Z, respectively. FIG. 23 shows the example determining the positions of the nucleotide succession TaAbT using a two-base walk and a one-base termination. In this example the DNA is assumed to be immobilized via a tag on the 5' end of the PCR primer strand and detected via a tag incorporated onto the 3' end of the product strand. In practice, the positions of the tags for immobilization and detection can be interchanged.

The DNA is first isolated, immobilized, and randomly degraded as outlined above. The DNA can be immobilized before, during, or after any of these steps. Next, the immobilized DNA is incubated in the presence of DNA polymerase and ddATP, ddGTP, and ddCTP to block every 3'OH end opposite T, C, or G in the template strand. After removal of the ddNTPs by washing, dTTP and polymerase are added to the immobilized DNA in order to add one or more thymidines to those unblocked 3' ends opposite one or more adenines on the template strand. This completes the first "T-walk." The unincorporated dTTP is then removed by washing. The immobilized DNA is then reacted with DNA polymerase and ddCTP, ddGTP, and ddTTP to block all 3' ends except those opposite thymidine on the template strand. (ddTTP normally cannot be incorporated, but is included to minimize the number of different reaction mixtures necessary to complete all steps). After completion of the reaction the ddNTPs are removed by washing. Next, the immobilized DNA is reacted with DNA polymerase and dATP to added one or more adenosines to every 3'OH end that is opposite a thymine in the template strand. This completes the "A-walk." Finally, tagged ddTTP is added and the reaction with DNA polymerase continued to add a single thymine dideoxyribonucleotide to those unblocked 3'OH ends that are opposite thymidine in the template strand. This completes the "T-termination." The samples are then subjected to conditions that denature the DNA and washed to remove all fragments that are not immobilized via the 5' tags.

Subsequently the 5' tagged strands are released by breaking the link used to immobilize the 5' tagged DNA and separated according to size by electrophoresis or other suitable method. Detection of the 3' tags will produce a ladder of fragment lengths representing all positions with the 3-base succession $T_aA_bT$, where a and b are integers greater than zero. This method can be modified slightly to detect all occurrences of $T_aA_bT_c$ by substituting tagged dTTP for tagged ddTTP at the terminal "T-termination" step.

By "walking" a number of steps before addition of the tagged nucleotides the positions of any succession of an arbitrary number of bases can be determined, e.g., $T_aA_bT_cG_dC_eG$. The complete sequence of the DNA can be determined with almost n-fold redundancy by analyzing the results of all possible combinations of walks (e.g., 36 reactions for 3-base sequencing). N-base sequencing requires the use of only eight polymerization solutions, each containing DNA polymerase, but differing in the nucleotide triphosphates.

5. Sequencing of multiple restriction fragments after a single Random Break Incorporation reaction The examples of Random Break Incorporation described above employ immobilization to separate one strand to be sequenced from other strands in order to sequence one piece of DNA immediately adjacent to the primer. However because the DNA remains double-stranded after the polymerase reaction, the DNA can be cleaved with restriction enzymes and separated into many fragments that can be sequenced according the procedures shown herein above, or using other techniques. As the result very long pieces of DNA can be sequenced without the need to subclone DNA.

6. Application of RBI sequencing to double-stranded RNA or RNA-DNA hybrids

In principle any double-stranded nucleic acid can be sequenced using the above techniques, using appropriate RNA-dependent DNA or RNA polymerases and appropriate nucleotide triphosphates. Such sequencing might be useful for determination of the sequences of RNA virus genomes, and products of RNA polymerase or reverse transcriptase.

C. Primer-Based Sequencing Methods

Initiation can also be accomplished with an oligonucleotide primer. Such methods include, but are not limited to 1) introduction of one or more oligonucleotide primers at the end or within the template DNA by local disruption of the DNA helix, and 2) introduction of one or more oligonucleotide primers at the end or within the template DNA by removal of a few bases from one strand (e.g. by digestion of the end of DNA by T7 gene 6 exonuclease).

D. Random Break Degradation Sequencing

The present invention provides another powerful method to create DNA molecules that terminate at a specified base. This method employs strand degradation rather than polymerization. The general principle involves incorporation of a degradation-resistant base analog at selected positions in a DNA strand, followed by exonuclease or chemical degradation to produce molecules terminated at the selected base. Separation of the DNA strands according to molecular weight produces a Sanger-like ladder of fragments that terminate at positions that have incorporated the base analog.

This method has been employed by substituting deoxyribonucleoside phosphorothioates (Labeit et al., 1986, 1987; Nakamaye et al., 1988; Olsen and Eckstein, 1989) or deoxyribonucleoside boranophosphates (Porter et al., 1997) at a fraction of the sites for a specific base. This incorporation can be done, for example, during PCR amplification by adding one boronated or thioloated deoxyribonucleotide triphosphate along with the 4 normal deoxyribonucleotide triphosphates. Subsequent degradation of the strand with snake venom phosphodiesterase and/or exonuclease III (exo III) causes the 3' end of the strand to be degraded until the boronated or thiolated linkage is reached. Alternatively chemical degradation of the thiolated linkages are able to terminate the strands at base-specific breaks. These methods for degrading DNA to produce sequencing ladders are related in principle to the Maxim-Gilbert methods of sequencing by chemical degradation using base-specific chemicals.

However, despite the apparent simplicity of the degradative methods for sequencing, they are not commonly used to sequence DNA. Chemical degradation is not ideal because of the sequence specificity of the reactions and background cleavage at non-specific sites. Exonuclease degradation is not ideal because the 3' termini can have mixed chemical composition, and exonucleases can have difficulty degrading long strands of DNA without sequence-specific accumulation or "read-through" of certain termination sites. As a result the sequencing ladders can have extra bands or missing bands, and the band intensities are not uniform (Porter et al., 1997). Initiating the exonuclease digestions from random breaks overcomes these difficulties by overcoming the need to do long-distance exonuclease degradation. In addition, degradation from random sites followed by DNA polymerization can be used to achieve dinucleotide, trinucleotide, and n-nucleotide sequencing.

The application of random break degradation to sequencing of single nucleotides is described first. PCR amplification is used to incorporate a resistant base analog into a fraction of the normal base positions in the DNA. Different fractions of incorporation of the resistant base have utility in various aspects of the invention, from incorporation of a single resistant base analog to 100% incorporation. In principle any base analog partially resistant to exonuclease degradation (such as phosphorothiolates or boranophosphates) can be used. As in previous applications one of the strands can be tagged by the use of a labeling or immobilization moiety attached to one of the primers. Alternatively both strands can be differentially labeled or immobilized using distinguishable chemical moieties on the two primers. Random single- or double-strand breakage by any of the methods previously described for Random Break Incorporation sequencing will produce a distribution of molecules cleaved at every or nearly every base site. Alternatively, deoxyribouracil can be incorporated at a fraction of the thymine base sites during PCR amplification, in the presence of dATP, dCTP, dGTP, dTTP mixed with a small amount of dUTP. These molecules can be cleaved by incubation with dU glycosylase and endonuclease IV (endo IV) or endonuclease V (endo V). Treatment of the DNA with exo III, snake venom phosphodiesterase, or other exonuclease that pauses or stops when reaching the resistant base will produce a spectrum of fragments terminated at resistant bases at the 3' ends.

Those fragments with tagged 5' ends and specifically terminated 3' ends can be separated by immobilization of the 5' immobilization tags, or specifically identified by detection of the 5' labeled tags. When immobilization tags have been used the molecules with specific 5' ends can be immobilized on a surface, washed free of other molecules, released into solution by reversal of the attachment to the surface, and separated according to size by electrophoresis, mass spectrometry, or other method. When the primers have been labeled with fluorescent, radioactive, or other detectable groups, the mixture of all fragments can be separated according to size and the molecules with tagged 5' ends that are terminated at the resistant bases can be detected in order to determine the positions of the resistant base analogs relative to the end of the original amplified DNA. By repeating this process with each of the four resistant base analogs, the entire sequence of the amplified DNA can be determined.

Random break degradation can also be used as the first step in dinucleotide, trinucleotide, and n-base sequencing. For example, to determine the positions of all dinucleotides of the sequence AT, PCR products are created having one tagged primer (able to be immobilized) and a fraction (e.g., 10–100%) of the adenines replaced by phosphorothiolated adenine. Random single- or double-strand breakage of the DNA followed by exonuclease treatment produces the spectrum of tagged DNA strands terminating with adenine. Addition of labeled ddTTP and DNA polymerase selectively labels those fragments that terminate with AT. When ddATP is added with polymerase, fragments terminated with AA are labeled. When resistant ddNTPs are used, the exonuclease does not need to be inactivated or removed before adding the polymerase. In the absence of resistant ddNTP analogs, the exonuclease can be removed by washing, inactivated by heating, or inhibited by changing ionic conditions or by adding a chemical inhibitor.

The tagged fragments are immobilized at any time during this process, washed free of the fragments with untagged 5' ends, size-separated by electrophoresis or other means, and the labeled terminal bases detected by fluorescence, radioactivity, or other means to determine the distances of the selected dinucleotides from one end of the amplified DNA molecules. When all four ddNTPs with distinguishable fluorescent labels are used, four dinucleotide sequences (e.g., AA, AT, AC, and AG) can be determined from the same nuclease/polymerase reaction and size-separation. Analysis of all 16 dinucleotide sequence combinations allows reconstruction of the complete nucleotide sequence of the DNA molecule. The advantages of this method of determining dinucleotide sequences (relative to the dinucleotide sequencing produced by polymerization without degradation) include: the dinucleotide sequence can be determined with only a single polymerization reaction; and the positions of homodinucleotides (e.g., AA) can be determined. Determination of trinucleotide and n-nucleotide sequences can be determined by adding one or more cycles of nucleotide "walks" between the exonuclease degradation step and the termination step.

Multiple base sequencing by random break degradation has an additional advantage over existing methods of sequencing by degradation in that only those molecules that have been degraded to leave a 3' OH terminus will become labeled and therefore will be detected. Those molecules that have been degraded to other chemical sites will not be extended by DNA polymerase and therefore will not be labeled and detected, thus reducing background. Further aspects of this method involve the direct sequencing of the degraded products, without base addition, and incorporation of four nondiscriminating ddNTPs to make the products of the degradation reaction suitable for direct sequence analysis.

E. Polymerases

In principle any DNA polymerase can be used under a wide variety of conditions so long as the polymerase can 1) initiate synthesis at the 3' end adjacent to the DNA break, 2) incorporate nucleotide bases complementary to the opposed, template strand, and 3) terminate synthesis at a selected base. Different polymerases are required to carry out the reaction under different circumstances, including the nature of the break and nature of the terminating base. For example, if the break consists of a single-strand nick, the polymerase must have a 5' to 3' exonuclease activity, a strand displacement activity, and/or a 3' to 5' exonuclease activity in order to incorporate new nucleotides onto the 3' end.

For incorporation of nucleotides during a net synthesis of DNA to move the 3' end forward to elongate the synthesized strand, enzymes exemplified by, but not limited to, *T. aquaticus* (Taq) DNA polymerase, *M. tuberculosis* DNA polymerase I, and other polymerases with 5' exonuclease activity can elongate the strand by adding new nucleotides to the 3' end while degrading existing nucleotides from the 5' end. These enzymes can incorporate bases at single-strand nicks and gaps. Enzymes such as *E. coli* DNA polymerase I Klenow fragment, Sequenase (modified T7 DNA polymerase), Thermosequenase, Vent DNA polymerase, and other many other enzymes without 5' exonuclease activities can incorporate new nucleotides by displacing the DNA on the 5' side of a nick or gap in the DNA. Enzymes such as T4 polymerase that lack 5' exonuclease activity and strand displacement activity require a gap in the DNA in order to elongate the 3' end.

In contrast to all the reactions that produce net synthesis of DNA at the 3' end (described in detail herein), polymerases with proofreading activities are also able to terminate synthesis after removing one or more nucleotides from the 3' ends. For example, Vent DNA polymerase, *E. coli* DNA polymerase I, *E. coli* DNA polymerase I Klenow fragment, and T4 polymerase have proofreading activities that can remove bases from the 3' ends and replace them with new nucleotide bases. The removal reactions are favored at low concentrations of deoxyribonucleotide triphosphates, and the polymerization reactions are favored by high concentrations of the nucleotide triphosphates. During these nucleotide replacement reactions the strands can be made to terminate at selected bases by 1) incorporation of selected dideoxyribonucleotides or 2) termination due to addition of only three of the four natural nucleotides such that all strands terminate one base before the selected base. These replacement synthesis reactions are especially valuable for terminating DNA synthesis at selected bases near the site of double-strand breaks, because a template strand is not available for strand elongation from the site of the break.

F. Detection Methods

Separation of sequence-specific double-stranded DNA fragments can be achieved by fractionation according to size using electrophoresis through media, including agarose, polyacrylamide, and polymer solutions. The physical form of the media can include flat layers, tubes and capillaries. Size fractionation can also be achieved by flow of solution through chromatographic media by the techniques of HPLC and FPLC. Mass spectroscopy is also contemplated for use in certain embodiments. The ability to fractionate DNA according to length is not affected by the presence of nicks in the double-stranded DNA. For example, it is well-known that nicked double-stranded DNA forms sharp bands during electrophoresis (Higashitani et al, 1992). Preparative collection of the DNA after separation can be performed manually by cutting pieces from gels, allowing the samples to flow into collection vessels, or by automatically sorting liquid samples. Typically, the fractions containing DNA fragments are detected by absorption spectrophotometry, fluorescence, radioactivity, or some other physical property.

In specific cases size fractionation before sequencing gels is not required for sequencing a specific restriction fragment. These cases include those where (a) only one restriction site is present in the DNA to be sequenced, (b) only one restriction fragment is long enough or short enough to give a good sequencing gel, and (c) two restriction fragments are produced, but one is removed from the reaction using an affinity immobilization or separation, e.g., based on the presence of biotin, digoxigenin, or a triplex-forming nucleotide on one of the fragments that leads to immobilization on magnetic beads, surfaces, or matrices, and d) only one restriction fragment is labeled.

Chip-Based Methods

The present invention contemplates carrying out the novel sequencing method described above using microscale devices. Thus, sequencing reactions using double-stranded template are contemplated to take place in microfabricated reaction chambers. The present invention contemplates that suitable microscale devices comprise microdroplet transport channels, reaction regions (e.g., chambers), electrophoresis modules, and radiation detectors. In a preferred embodiment, these elements are microfabricated from silicon substrates according to those methods known in the art. As a mechanical building material, silicon has well-known fabrication characteristics. The economic attraction of silicon devices is that their associated micromachining technologies are, essentially, photographic reproduction techniques. In these processes, transparent templates or masks containing opaque designs are used to photodefine objects on the surface of the silicon substrate. The patterns on the templates are generated with computer-aided design programs and can delineate structures with line-widths of less than one micron. Once a template is generated, it can be used almost indefinitely to produce identical replicate structures. Consequently, even extremely complex micromachines can be reproduced in mass quantities and at low incremental unit cost—provided that all of the components are compatible with the silicon micromachining process. While other substrates, such as glass or quartz, can use photolithographic methods to construct microfabricated analysis devices, only silicon gives the added advantage of allowing a large variety of electronic components to be fabricated within the same structure.

The principal modern method for fabricating semiconductor integrated circuits is the so-called planar process. The planar process relies on the unique characteristics of silicon and comprises a complex sequence of manufacturing steps involving deposition, oxidation, photolithography, diffusion and/or ion implantation, and metallization, to fabricate a "layered" integrated circuit device in a silicon substrate (U.S. Pat. No. 5,091,328).

For example, oxidation of a crystalline silicon substrate results in the formation of a layer of silicon dioxide on the substrate surface. Photolithography can then be used to selectively pattern and etch the silicon dioxide layer to expose a portion of the underlying substrate. These openings in the silicon dioxide layer allow for the introduction ("doping") of ions ("dopant") into defined areas of the underlying silicon. The silicon dioxide acts as a mask; that is, doping only occurs where there are openings. Careful control of the doping process and of the type of dopant allows for the creation of localized areas of different electrical resistivity in the silicon. The particular placement of acceptor ion-doped (positive free hole, "p") regions and donor ion-doped (negative free electron, "n") regions in large part defines the interrelated design of the transistors, resistors, capacitors and other circuit elements on the silicon wafer. Electrical interconnection and contact to the various p or n regions that make up the integrated circuit is made by a deposition of a thin film of conductive material, usually aluminum or polysilicon, thereby finalizing the design of the integrated circuit.

Of course, the particular fabrication process and sequence used will depend on the desired characteristics of the device. Today, one can choose from among a wide variety of devices and circuits to implement a desired digital or analog logic feature.

It is not intended that the present invention be limited by the nature of the reactions carried out in the microscale device. Reactions include, but are not limited to, sequencing according to the present invention, restriction enzyme digests, nucleic acid amplification, and gel electrophoresis.

Continuous flow liquid transport has been described using a microfluidic device developed with silicon (Pfahler et al., 1990). Pumps have also been described, using external forces to create flow, based on micromachining of silicon (Van Lintel et al., 1988). Discrete droplet transport in silicon is also contemplated.

III. Mapping Techniques

Often it is desirable to map sequence information in very long pieces of DNA (e.g., cosmids, YACs, and within or at the ends of intact chromosomes). The landmarks that can be mapped using long-range SR reactions include (a) specific known sequences, such as those associated with a particular genes, (b) restriction sites, (c) anonymous sequences present in a library of cloned or PCR™ amplified genomic or cDNA sequences, (d) repetitive sequences such as Alu repeats, CpG islands, dinucleotide and trinucleotide repeats, SINES, LINES, and telomere repeats, (e) unusual secondary structures such as triplex DNA, quadruplex DNA, cruciform DNA, and (f) specific types of lesions, such as thymidine dimers. Present techniques are unable to map these types of features because (1) many of the features are characteristic of double-stranded DNA, and (2) mapping usually requires a nearly synchronous progression of the synthesis of new DNA. Neither of these conditions seem to be met by enzymes utilizing a single-stranded template. The present invention contemplates using the strand replacement method with a highly processive SR polymerase, such as Taq DNA polymerase, for this task.

Figure 8:
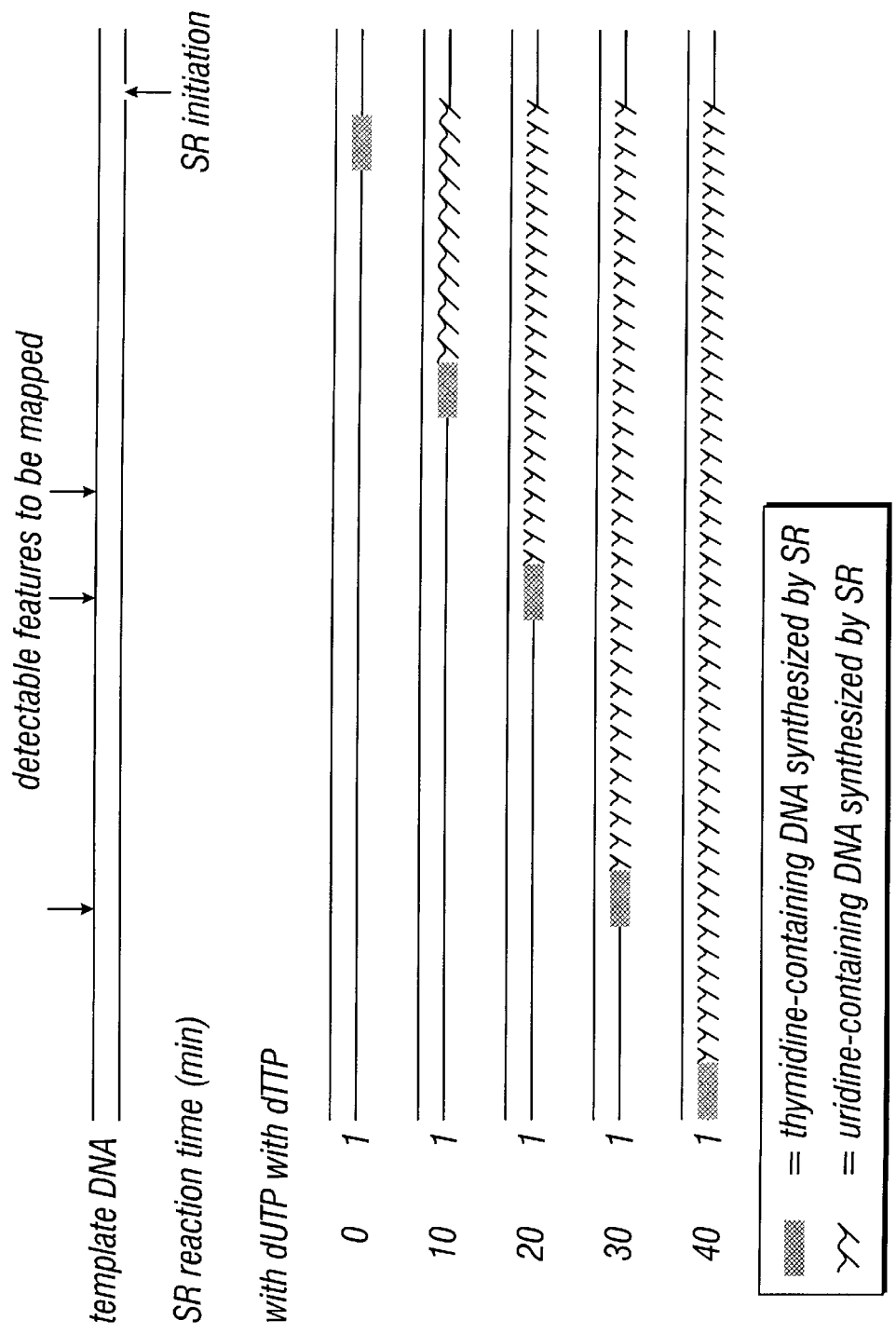
FIG. 8. Schematically shows one embodiment of the strand replacement method of the present invention for mapping the distance of genetic sites from the strand replacement initiation site. A template DNA molecule having detectable features to be mapped and a strand replacement initiation site is shown in the top panel. The bottom panel shows the products of strand replacement reactions with dUTP incorporation times of 0, 10, 20, 30 and 40 minutes, followed by a 1 minute strand replacement reaction incorporating dTTP. The thymidine-containing DNA synthesized by the strand replacement reaction is shown as a cross-hatched box, and the uridine-containing DNA synthesized by the strand replacement reaction is shown as a hatched line.

In one embodiment, SR synthesis initiates at a unique site using an excess of processive polymerase, which incorporates dATP, dGTP, dCTP, dUTP (or any other labile base) into the DNA (FIG. 8). After a controlled period of incorporation of the labile base, conditions are changed to incorporate only the stable bases dATP, dGTP, dCTP, and dTTP, with one of the stable bases being labeled, in this example labeled dTTP. The labeled base can be, for example, radioactively labeled, fluorescently labeled, or chemically labeled with biotin, among others. The uracil bases can be removed using dU glycosylase (Boehrenger Mannheim), and the sites efficiently converted to nicks by heating the DNA, treatment with base, or enzymatic cleavage with endo IV or endo V. After destruction of the dUTP-substituted DNA, the labeled DNA from the different SR reaction times (representing DNA sequences located at different distances from the initiation site) can be hybridized to a sequence of interest (e.g., telomeric sequences, dinucleotide repeats, Alu sequences, cloned or PCR™-amplified sequences, expressed sequences from a cDNA library, etc.).

In the example shown schematically in FIG. 8, positive hybridization would be detected for the samples from SR reactions carried out for about 15 min, 20 min, and 30 min. If the measured rate of SR elongation was 250 nucleotides per min, those features would be mapped as being 3.75 kb, 5.0 kb, and 7.5 kb from the initiation site. To map the positions of restriction fragments the fragments would be separated by electrophoresis in agarose, transferred to a filter, and hybridized to the labeled SR products formed at different distances from the initiation sites. By hybridizing to restriction fragments transferred from an agarose gel, the order of the restriction fragments can be easily mapped. This information is very useful in large-scale sequencing projects to order the restriction fragments in cosmids and YACs.

As the time of polymerization increases the polymerases can lose synchrony, which causes the width of the band of stable DNA to increase, reducing resolution. To overcome this problem agents can be introduced to reversibly halt the polymerase molecules at specific sequences. When the arrest is reversed all of the polymerases will regain their initial synchrony. For example, triplex-forming oligonucleotides can bind to recognition sequences along DNA and can arrest the progress of Klenow fragment (Hacia et al., 1994). The arrest by oligonucleotides should be reversed by mild heating or changes in pH.

The technique described can also be used to map features in the DNA that terminate SR, such as unusual secondary structure, triplex formation, and specific protein binding. In this case the SR reaction would be performed using dATP, dGTP, dCTP, and dTTP and the products separated by molecular weight using electrophoresis. Sites of pausing of the polymerase would be detected by increase in product concentration or the onset of hybridization to a specific DNA probe.

Dinucleotide/Trinucleotide Strings

The information gained by multiple nucleotide sequencing as discussed above in Section III is also very useful for mapping the sequence information in a long DNA molecule. The map of positions of specific dinucleotides or trinucleotides serve as a fingerprint to identify overlapping parts of different DNA molecules, much the same as restriction fragment analysis and STS hybridization has been used to map overlapping DNA clones. The multiple base ladders contain more information and are more easily interpreted than the patterns of restriction fragment lengths or STS hybridization, because the ladders can be directly related to positions along the DNA molecule and can be directly related to even partial base sequence information. The multiple base ladders can also give information about the underlying structure or function of the DNA over long distances. For example, high frequencies of the dinucleotide CG can signal the presence of so-called "CpG islands" that are associated with genes.

IV. Telomere Analysis

The present invention overcomes many of the problems inherent in the art with regards to telomere analysis, including the lack of the ability to determine the sequence of the subtelomeric region, quantitation of the amounts of single-stranded overhangs present on chromosomes. Details of the present methods are presented below.

A. Sequencing

The present invention contemplates that the above-described sequencing method can be applied to a variety of double-stranded templates, including but not limited to telomeric DNA. Telomeres are special DNA structures at the ends of eukaryotic chromosomes, which are necessary for genome stability. In humans telomeres progressively shorten during somatic cell proliferation, perhaps eventually leading to chromosome instability. The rate and extent of shortening depends upon the type of tissue, and individual factors such as genetic background, age, and medical condition.

In human germ line and tumor cells, telomere metabolisis is different from that of somatic cells, leading to stabilization of the length of telomeres, which is believed to be due to de novo extension of 3' overhangs by the enzyme telomerase recombination, and perhaps other factors such as nucleases. Currently, the only parameter of telomere structure that can be measured is the length of the terminal restriction fragments. Measurements of the rate of telomere shortening cannot be performed in human tissues in less that ten years, or in selected human cultured cells in less than one month. Telomere shortening in most plants and animals cannot be measured due to excessive telomere length. The only existing test of the state of an individual's telomeres is a PCR™ assay of the in vitro telomerase activity, which is correlated with cell proliferation but not a measure whether telomeres are eroding or growing.

The present invention contemplates that the sequencing method of the present invention can provide a quantitative mapping of the DNA structure at the ends of telomeres. Indeed, preliminary results from the use of the novel sequencing method reveals long 3' overhangs at the ends of human chromosomes, suggesting a third important factor for regulating telomere length and function. The present invention contemplates that such mapping allows for the diagnosis of chromosome instabilities caused by telomerase, nucleases, recombination, and other effects important to aging and cancer.

B. Two-Dimensional Techniques and Analysis of Single-Stranded Overhangs

The present invention provides a variety of methods to analyze telomeres, including two-dimensional gel techniques, and hybridization and quantification of labeled oligonucleotides to the single-stranded regions of telomeres. Examples 1–5 below present details regarding these techniques.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

In some of the examples below fibroblasts were used. For these studies, three derivative cultures of female human fetal lung fibroblasts were purchased and grown strictly according to instructions from the NIA Aging Cell Repository (Coriell Institute for Medical Research, Camden, N.J.). Normal IMR-90 primary cells (catalog #190 P04 and #190 P10, after 4 and 10 laboratory passages) and post-crisis immortal SV40 virus-transformed IMR-90 (#AG02804C) were harvested at about 80% confluence. The IMR-90/P04 and IMR-90/P10 cells were harvested after −33 and −63 post-fetal population doubling, respectively.

In some studies human umbilical vein endothelial (HUVE) cells and human leukocytes were used. HUVE cells were grown as described (Dixit et al. 1989) and harvested after 11 passages. Human leukocytes were separated from fresh blood by isotonic lysis (Birren et al., 1993). 1–2×10$^8$ cells were harvested by centrifuging 3× for 10 min at 800×g in 15 ml cold PBS followed by resuspension in PBS (−12× 10$^8$/ml).

A number of the examples below involve the use of nucleic acid isolated from nuclei. Nuclei were prepared using centrifugations at 4° C. as above: 1–2×10$^8$ washed cells were centrifuged once in 15 ml of nuclear buffer (60 mM KCl, 15 mM NaCl, 15 mM HEPES pH 7.4, 3 mM MgCl$_2$, 6 μM leupeptin, 1 mM iodoacetate, 1 mM phenyl-methyl sulfonyl fluoride), once in 1.5 ml nuclear buffer, twice in 15 ml nuclear buffer with 0.1% digitonin, and once in nuclear buffer with digitonin without iodoacetate; nuclei were resuspended in 1 ml of nuclear buffer without iodoacetate, diluted to 10$^7$ cells/ml with nuclear buffer without iodoacetate prepared with 50% glycerol, and frozen in liquid N$_2$.

A variety of commercially available reagents were employed. Tissue culture supplies were from Sigma (St. Louis); restriction enzymes, S1 nuclease, DNA polymerase I, T4 DNA ligase, and random labeling kit from GibcoBRL; Hinf I from BioLabs; Bal 31 nuclease, T4 DNA polymerase, dU-glycosylase, proteinase K and Agarase from Boehrenger Mannheim; Klenow fragment (exo) from Ambion; T7 gene 6 exonuclease from Amersham/USB; agarose from Gibco-BRL and FMC; ZetaProbe GT membrane and PCR™ rules from BioRad; radioisotopes from Amersham. Oligonucleotides were synthesized at the University of Michigan Biomedical Research Core Facility. Oligonucleotide (CCCUAA)$_4$ (SEQ ID NO:1; TelC) was used as a primer for strand replacement reactions. Oligonucleotides (CCCTAA)$_3$ CCC (SEQ ID NO:2), (UUAGGG)$_4$ (SEQ ID NO:3; TelG), CCCTCCAGCGGCCGG(TTAGGG)$_3$ (SEQ ID NO:4) and (CCCUAA)$_4$ (SEQ ID NO:1) were used for probe preparation.

For DNA purification, a protocol for isolation of high molecular weight DNA in solution was used (Birren et al., 1993). Tissue culture and fresh blood cells were washed 3 times at 800×g in PBS, and 10$^8$ washed cells were resuspended in 0.5 ml PBS. Then 0.125 ml 20 mg/ml proteinase K solution, 1.625 ml 0.25 M EDTA, pH 8.0, and 0.25 ml 10% SDS were added in the indicated order, gently mixed and incubated at 50° C. Frozen nuclei were washed three times with nuclear wash buffer (15 mM NaCl, 15 mM Tris-HCl pH 7.5, 60 mM KCl, 3 mM MgCl$_2$), resuspended at 300–400 μg/ml, and gently mixed with an equal volume of digestion buffer (30 mM Tris HCl pH 7.5, 100 mM EDTA pH 8, 2% SDS, 2 mg/ml proteinase K), and placed at 50° C. Equal amounts of fresh proteinase K solution were added every 12 h, and incubation continued to 36 h. DNA was extracted with buffered phenol, followed by phenol/chloroform and chloroform extractions. The clear, viscous DNA solutions were dialyzed against TE. DNA concentrations were determined by spectrophotometry (usually 100–200 μg/ml) and DNA solutions were stored at 4° C. for several months without detectable loss of integrity. For certain critical studies (e.g. for G-overhang length analysis) the DNA was digested with RNase. Telomere molarity was calculated assuming 75×10$^6$ bp per telomere (or 3.4×10$^9$ bp per haploid genome).

EXAMPLE 1

Oligonucleotide Primer Dependent Strand Replacement on Double-Stranded Template Having Single-Stranded Regions Created by Nuclease Digestion Telomere DNA is difficult to sequence due to the repetitive sequences involving DNA strands that are either rich in guanine or cytosine. Single-stranded GC rich DNA forms intramolecular and intermolecular secondary structure that causes premature termination of DNA polymerization. In addition, G-rich DNA is able to form non-Watson-Crick hydrogen bonding involving G:G base pairs that are often more stable than Watson-Crick double-stranded DNA. In vitro, single-stranded G-rich telomere DNA can form a variety of non-canonical structures including G-quartets, triple helices and G:G base pairing.

Figure 10:
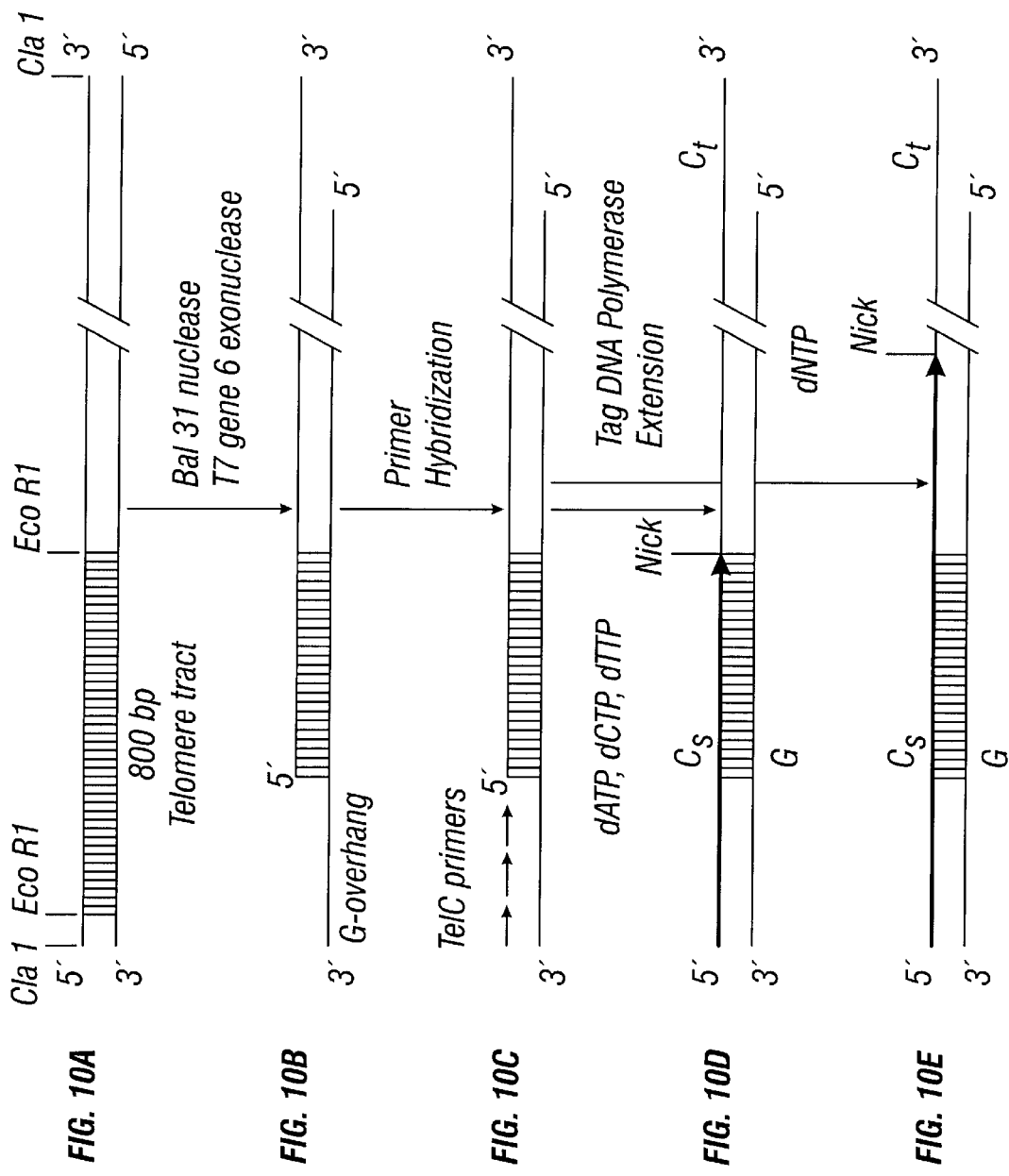
FIG. 10A, FIG. 10B, FIG. 10C, FIG. 10D and FIG. 10E. Schematically shows the introduction of single-stranded regions in a model telomere double-stranded construct, and PENT reactions using the TelC primers.

In this example, the primer-dependent strand replacement method of present invention was used to measure human telomere DNA. FIG. 10 shows the strand replacement approach as applied to the detection and quantitation of G-tails in human chromosomes. The oligonucleotide (CCCTAA)$_4$ (SEQ ID NO:5; TelC$_7$) is hybridized under non-denaturing conditions to available G-rich tails and extended using Taq polymerase. The polymerase fills the gap between the primer and 5'-end of the C-strand and then propagates the nick in the 3' direction. If several molecules of TelC bind to the overhang, all but the last one will be degraded during the reaction. When electrophoresed on a denaturing alkaline agarose gel and probed with both the G-rich and C-rich telomeric sequences, the reaction products should appear as three bands: C, corresponds to the newly-synthesized extension products; $C_t$ corresponds to the trimmed original C-rich strands; and $C_o$ corresponds to the original G-rich strands and untrimmed C-rich strands from any telomeric ends without overhangs or with such short overhangs that they cannot bind the primer.

In this example, the reaction was carried out on a model linear telomere construct. The construct with 520–700 bp of double-stranded human telomere DNA and 100–200 b of G-rich overhang was constructed from plasmid Sty11. Sty 11 was cut with ClaI which leaves 10 bp of polylinker DNA at the end of a 800 bp telomere tract. The linearized plasmid was digested with Bal 31 for 30 seconds at 30° C. using 2 units of enzyme with 10 µg DNA in 100 µl of 600 mM NaCl, 12.5 mM CaCl$_2$, 12.5 mM MgCl$_2$, 20 mM Tris-HCl pH 8.0, and 1 mM EDTA. The DNA was extracted and resuspended in TE. EcoR I restriction and electrophoretic analysis determined that the Bal 31 had trimmed about 60 bp from each end, sufficient to expose the telomeric repeat. To produce a 3' overhang 5 µg of linearized or linearized/Bal 31 treated DNA was incubated with 100 units of T7 gene 6 exonuclease in 50 µl of 40 mM Tris-HCl pH 7.5, 20 mM MgCl$_2$, 50 mM NaCl at 20° C. for different times, extracted, and resuspended in TE. The average G-tail length and length distribution were determined by digestion with EcoRI, electrophoresis in 1.5% agarose/40 mM NaOH and analysis of the length of the C-strand. It was determined that, following the above treatment, one end of the construct had a 650 bp terminal tract of double-stranded telomeric DNA with a 100 b G-tail.

The strand replacement reaction was performed using Taq DNA polymerase. The optimized reaction was performed in 50 µl of the standard Taq polymerase buffer [composed of 20 mM Tris-HCl pH 8.3, 50 mM KCl, and 2 mM MgCl$_2$ containing 50 µM dNTPs, 5–10 nM TelC primer, 0.1–1 fool of DNA telomere ends (5–50 µg of human DNA or 0.1–1 ng of Sty11 telomere construct) and 2 units of Taq polymerase] and was carried out at 55° C. To insure the hybridization of the TelC primers to all single stranded telomere ends, the ingredients of the reaction (except Taq polymerase) were placed into 0.5 ml thin-wall PCR™ tubes, mixed, covered with mineral oil, and incubated at 45° C. for 1 h in a DNA Thermal Cycler 480 (Perkin-Elmer, Cetus). The temperature was increased to 55° C. for 5 min, and Taq DNA polymerase was added. Aliquots were removed at the desired times and quenched on ice with 10 mM EDTA. All DNA samples were incubated with dU-glycosylase (1 µl enzyme 50 µl reaction) at 37° C. for 1–2 h, ethanol precipitated, washed and dried. The dU-glycosylase promoted primer degradation during alkaline electrophoresis, greatly reducing the background on Southern blots.

The results of the strand replacement reaction using the model construct show that the size of the $C_s$ strand increased at the same rate as the size of the $C_t$ strand decreased, ruling out strand displacement (Henderson et al., 1988). In the presence of four dNTPs the nick-translation reaction proceeded to the opposite end of the linear construct. In the presence of only dATP, dTTP and dCTP the reaction proceeded only to the end of the telomeric tract, producing a discrete 750 b C-rich strand. Substitution of dTTP with dUTP and incubation of the reaction products with dU-glycosylase followed by alkaline treatment led to complete elimination of the $C_s$ strand. After long reactions the $C_t$ strand hybridized with the random-primed plasmid, but not (TTAGGG)$_4$ (TelG).

A 100 b overhang is long enough to initiate multiple strand replacement reactions, however the terminal $C_s$ strand should destroy and replace internally-located primers and products. Thus the $C_s$ product made without dGTP had the same size as the C-rich fragment without T7 gene 6 treatment. No strand replacement products were found (a) without primers, (b) with TelG primers, (c) with non-telomeric primers, or (d) on constructs without G-tails.

In sum, the strand replacement signal is dependent upon the presence of the TelC primer showing that products are not formed from internal nicks or gaps. In the model system, the strand replacement reaction with (TTAGGG) overhangs is specific for a primer containing the (CCCTAA) repeat, and blunt-ended telomeric ends are not detected.

EXAMPLE 2

Oligonucleotide Primer Dependent Strand Replacement on Double-Stranded Template Having Naturally Occurring Single-Stranded Regions In this example, the strand replacement method was used to detect naturally occurring single-stranded regions of telomeric DNA. Specifically, the strand replacement method was used to detect G-tails in IMR-90 normal primary human fibroblasts. These telomeres are from fetal lungs and therefore have very long telomeres (approximately 12 kb). High molecular weight (>100 kb) IMR-90 DNA was subjected to the strand replacement reaction and the products were analyzed by I-D alkaline gel electrophoresis.

Specifically, high molecular weight primary IMR-90 cell DNA was subjected to strand replacement for 5, 10 and 15 min and electrophoresed. Alkaline electrophoresis was performed in 0.8–1% agarose with 40 mM NaOH. The gel was prepared with 50 mM NaCl, and 1 mM EDTA, solidified, and soaked in 2 liters of alkaline electrophoretic buffer (40 mM NaOH and 1 mM EDTA). Dried DNA samples were dissolved in alkaline loading buffer (2.5% Ficoll, 50 mM NaOH, 1 mM EDTA, and 0.025% Bromocreosol green), loaded and run at 1 V/cm (250–300 mA) for 12–16 hours at room temperature with buffer circulation. The gel was neutralized by soaking in 1×TBE buffer for 1 h and vacuum blotted onto the nylon membrane. The material transferred to the membrane was thereafter probed with radioactive TelG. Reactions were conducted with four dNTPs with TelC; with four dNTPs without TelC primer; and with three dNTPs with TelC primer.

The time course of the reactions with TelC primer and four dNTPs showed that the rate of $C_s$ synthesis was approximately 250 b/min. DNA fragments of similar size were synthesized when dGTP was omitted, indicating the telomeric origin of the products and the absence of guanine blocks in the terminal 4 kb of the human telomere C-strands.

Incorporation of dUTP followed by incubation with dU-glycosylase and alkaline treatment caused loss of the $C_s$ products. Reactions with equal numbers of human and rat telomeres gave nearly identical amounts of $C_s$ product, even though the rat telomeres are 10 times longer (Makarov et al., 1993), consistent with priming only at termini. These results demonstrate that the strand replacement synthesis with Taq DNA polymerase can proceed in a controlled fashion at least 4 kb along double-stranded native DNA.

The results are interpreted as synthesis of new DNA strands beginning at the telomere termini. Several alternative explanations can be ruled out. First, no products were generated in the absence of the TelC primer, showing that there are not significant numbers of gaps or nicks in the C-rich strands. Discontinuities in the G-rich strands are ruled out by the fact that the products were of high molecular weight.

To further confirm the nature of the reaction, alkaline agarose electrophoresis analysis and detection by filter hybridization was investigated when the naturally occurring G-tails were removed. To remove G-tails 10 mg of IMR-90 DNA was incubated with 300 units/ml S1 nuclease for 15 min at 37° C. in 50 mM NaAc pH 4.5, 1 mM $ZnCl_2$, and 200 mM NaCl, or with 20 units/ml Bal 31 nuclease for 5 min at 30° C. in Bal 31 buffer. For the same purpose, 2 ng of plasmid construct, 10 mg of IMR-90 DNA, or a mixture of the two was incubated with 10 units of T4 DNA polymerase for 10 min at 37° C. in 50 mM Tris-HCl pH 8.8, 15 mM $(NH_4)_2SO_4$, 7 mM $MgCl_2$, 0.1 mM EDTA, 10 mM 2-mercaptoethanol, and 100 µg/ml bovine serum albumin DNA was extracted and resuspended in buffer.

T4 DNA polymerase trimming reduced the amount of product by more than 10-fold in reactions with (a) the plasmid construct, (b) IMR-90 DNA, or (c) a mixture of IMR-90 DNA and construct ("+" indicates treatment and "−" indicates no treatment). Treatment of IMR-90 DNA with S1 nuclease or with Bal 31 nuclease completely eliminated the reaction. These data strongly indicate that the strand replacement synthesis requires a 3' G-rich terminus.

G-tails do not seem to be generated or lost during DNA isolation. Concentrations of proteinase K and EDTA were increased during DNA isolation, without effect on the signal. The isolation protocols were changed in an attempt to test the sensitivity of the assay to formation of unusual secondary structure (e.g., exposure of a G-tail due to strand slippage, or concealment of a G-tail due to formation of G-quartets). Cells and nuclei were incubated with the digestion buffer at 45, 37, and 25° C. to reduce the chance of thermally-induced conformational transition. $K^+$ and $Na^+$ ions were excluded and replaced by $Li^+$ or $Tris^+$ in all isolation steps to reduce the possibility of G-quartet formation. Extractions with phenol and chloroform were replaced by dialysis to avoid organic solvents and precipitation. None of the protocols tested had qualitative or quantitative effects on the strand replacement reaction or on non-denaturing hybridization (see below). Thus the assays for G-tails are robust and not sensitive to changes in treatment.

EXAMPLE 3

Strand Replacement Synthesis to Measure the Abundance and Length of Telomere 3' Overhangs In this example, the strand replacement method of the present invention was combined with non-denaturing hybridization to determine the average lengths of 3' tails in humans. Hinf I digested human DNA, plasmid constructs with 100 b, 170 b and 220 b overhangs, or a nearly equimolar (in terms of telomere ends) mixture of human and plasmid DNA were hybridized at 50° C. with 1 nM $^{32}$P-TelC in 20–30 µl of hybridization buffer (50 mM NaCl, 1 mM EDTA and 50 mM Tris-HCl, pH 8.0) for 12–16 h. Some of the samples were subjected to strand replacement (100 mM dNTP, 5 units Taq DNA polymerase; 10 min at 55° C.), then all samples were electrophoresed on a 1% agarose/TAE gel, electroblotted onto a nylon membrane for 16 h and quantitated. The absolute telomere molarity of the IMR90/P04 DNA solution was approximated by spectrophotometry. The molarities of plasmid constructs and telomeres from different human cells were determined by CCD analysis of fluorescence of ethidium bromide stained gels; the signal intensities of plasmids and telomeres were normalized to the signal intensities of a DNA Mass Ladder (GIBCO BRL) and IMR90/P04 DNA, respectively. $^{32}$P-labeled TelC was hybridized under native conditions to the same numbers of human telomeres and control DNA constructs with known lengths of 3' overhangs. The telomeres and constructs were electrophoresed to remove unbound TelC, and the average length of G-tails determined by two independent methods.

Figure 11:
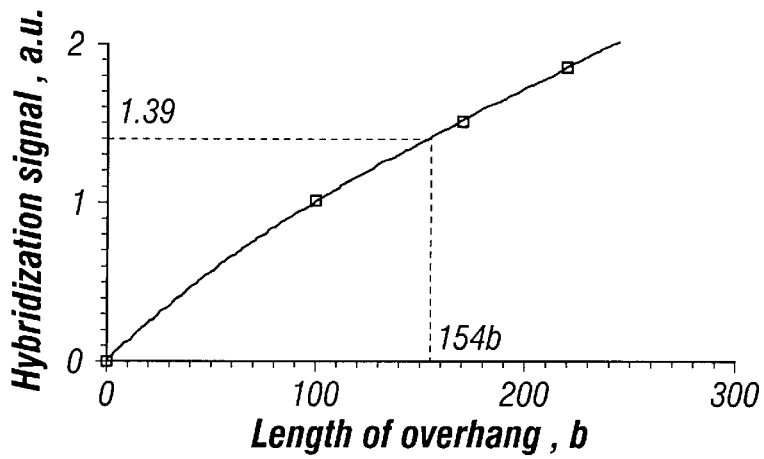
FIG. 11. A plot used to calculate the estimated telomere overhang length. The vertical axis shows the magnitude of the nondenaturing hybridization signal for constructs with 100 bp, 170 bp and 220 bp G tails (hybridization signal, a.u.), and the horizontal axis shows the length of the overhang (bp).

An autoradiogram of DNA samples from blood, HUVE, and primary IMR-90 cells showed broad bands of radioactivity at 10–12 kb, coinciding with the telomere terminal restriction fragments found by denaturing hybridization, except for the absence of the sharp bands due to the interstitial $(TTAGGG)_n$ tracts. Treatment of the human and construct DNA with S1, mung bean, or Bal 31 nucleases, or with T4 DNA polymerase led to elimination or significant reduction (after T4 polymerase) of the non-denaturing hybridization signal without affecting the size or intensity of the denaturing hybridization signal. The strength of the TelC hybridization was the same for DNA isolated from both cells and nuclei, prepared by phenol extraction or by only proteinase K/SDS digestion and dialysis. Non-denaturing hybridization with TelG was 20–30 times lower than with TelC for both human and plasmid DNA, consistent with the absence of single-stranded $(CCCTAA)_n$ and a very low level of G:G hydrogen bonding. DNA constructs with $(CCCTAA)_n$ overhangs hybridized strongly to TelG and showed no binding to TelC. The low efficiency of hybridization of telomeres with TelG is strong evidence that the G-tails are covalent extensions (i.e., different lengths of the C- and G-rich strands) rather than conformational extensions (i.e., slippage of the C- and G-rich strands producing G-overhangs and C-loops). TelC hybridizes to the constructs with weight-average G-tail lengths of 0, 100, 170, and 220 b showed that the TelC hybridization signals were nearly proportional to the average lengths of the G-overhangs (FIG. 11). Thus, quantitation of the amount of TELC hybridization under these non-denaturing conditions can be used to determine the abundance of single stranded telomere DNA at the ends of chromosomes.

The lengths of the G-tails were first measured by comparing the hybridization signal of TelC to genomic DNA with that of TelC to DNA constructs having G-tails of known lengths. Using non-denaturing hybridization of Hinf I-digested IMR-90/P04 DNA mixed with an equimolar amount of telomeric ends from the construct with a 100 b G-tail, the hybridization signal of the human DNA was 1.25 times greater than that of the plasmid control. To accurately determine the relative molarity of the human and plasmid overhangs, the same samples were subjected to a 10 min strand replacement reaction, which should destroy all but the terminal TelC. The relative hybridization signals for the human and plasmid DNA were easily measured, because of the low background in the plasmid-only control. Assuming that the same number of labeled oligonucleotides remained bound to the ends of the human and plasmid DNA, the molarity of the plasmid ends was 11% greater than that of the human DNA. This similarity in the estimated molarities of the telomere ends and G-overhangs is consistent with the inventors' finding that most or all telomeres have G-tails. Thus, the non-denaturing hybridization signal for the human DNA was 1.39 times greater than to the same number of moles of plasmid with 100 b overhang. Using the experimental dependence of hybridization upon G-tail length, the inventors calculate that the IMR-90/P04 overhangs were 154 b long (FIG. 11).

In a separate study Tel C was hybridized under non-denaturing conditions to IMR-90/P04, IMR-90/P10, immortal IMR-90, leukocyte, and HUVE cells. The relative amounts of DNA were determined from ethidium bromide fluorescence, and the relative amounts of hybridization by autoradiography. The lengths of the G-tails were between 130 and 210 b long, assuming that the IMR-90/P04 overhangs were 154 b long (Table 3).

The lengths of the IMR90-P04 G-tails were also estimated from the fraction of hybridized TelC that is removed by the strand replacement reaction. SR decreased the radioactivity of the human and plasmid DNA by factors of 6.2 and 4.5, respectively, leading one to conclude that the human and plasmid ends bound an average of 6.2 and 4.5 oligonucleotides. Assuming that Tel C saturated the G-tails, the size of the overhangs can be estimated to be 149 in human and 108 bases in the construct. The consistency of these numbers with the earlier results increases the confidence in the estimates of the length and abundance of telomere G-tails.

templates that the functional parts of telomeres (FIG. 12) include regions C and D only, and that exposure of regions A or B to the termini of one or more chromosomes as the result of telomere shortening in normal or precancerous human cells will result in dysfunction of the telomeres, specifically arrest of growth and/or chromosome instability. Evidence that the sequences in region B are not functional comes from studies showing that cells cannot survive with new telomeres made with telomere-like sequences such as (TTGGGG)n and that cell-free extracts are not able to prevent such sequences from non-covalently attaching to each other. Such non-covalent attachments in human cells might lead to the non-clonal telomere associations that characterize the cells of elderly humans and certain human diseases such as ATM and giant cell osteogenic sarcoma. It is critical to directly measure the average and the shortest lengths of region C in human cells and to determine the DNA sequences in region B in order to definitively test the telomere hypothesis of aging and cancer. If the proposed mechanism is correct, such measurements could find clinical applications to test individual humans to accurately measure the rate of telomere shortening or lengthening, predicting future chromosome instabilities, predicting the future behavior of tumor cells or lymphocytes in HIV positive or Alzheimer's individuals, and predicting the efficacy of telomere-modifying therapies.

In one embodiment, the steps of the method of the present invention for mapping sequence defects in telomeres comprises: 1) initiation of the synthesis of a new DNA molecule beginning at or near the chromosome terminus, 2) elongation of the synthesis of a new DNA molecule with the repetitive sequence (CCCTAA)n, which is characteristic of a functional vertebrate telomere, and 3) termination of

TABLE 3

Measured Fractions And Lengths Of G-rich Tails In Human and Control DNA

| DNA Sample | Control Plasmid | IMR-90/ P04 | IMR-90/ P10 | IMR-90 Immortal | HUVE | Leukocyte |
|---|---|---|---|---|---|---|
| Fraction of strands with detectable G-tails[a] | 0.85 (N = 1) | 0.86 ± 0.03 (N = 17) | 0.89 ± 0.03 (N = 4) | 0.88 ± 0.03 (N = 3) | 0.87 ± 0.03 (N = 3) | 0.82 ± 0.05 (N = 3) |
| Average length of G-tail (bases)[b] | 100[c] (108)[d] | 154 (149)[d] | 210 | 130 | 150 | 200 |

EXAMPLE 4

Measuring Telomere Defects

The current method of studying telomere shortening is inaccurate in determining the average length of telomeres, unable to determine the distribution of telomere lengths (particularly the lengths of the shortest telomeres) and is insensitive to defects in the sequences of the telomeric DNA. The present invention provides methods to overcome these limitations. These methods can measure the potential that individuals (particularly those with age-related conditions such as cancer, AIDS, Alzheimer's, atherosclerosis, and the progerias) will experience a "telomere crisis" due to telomere shortening, and in predicting or evaluating the efficacy of anti-telomerase therapy or other therapies designed to control telomere function in the treatment of those diseases.

Figure 12:
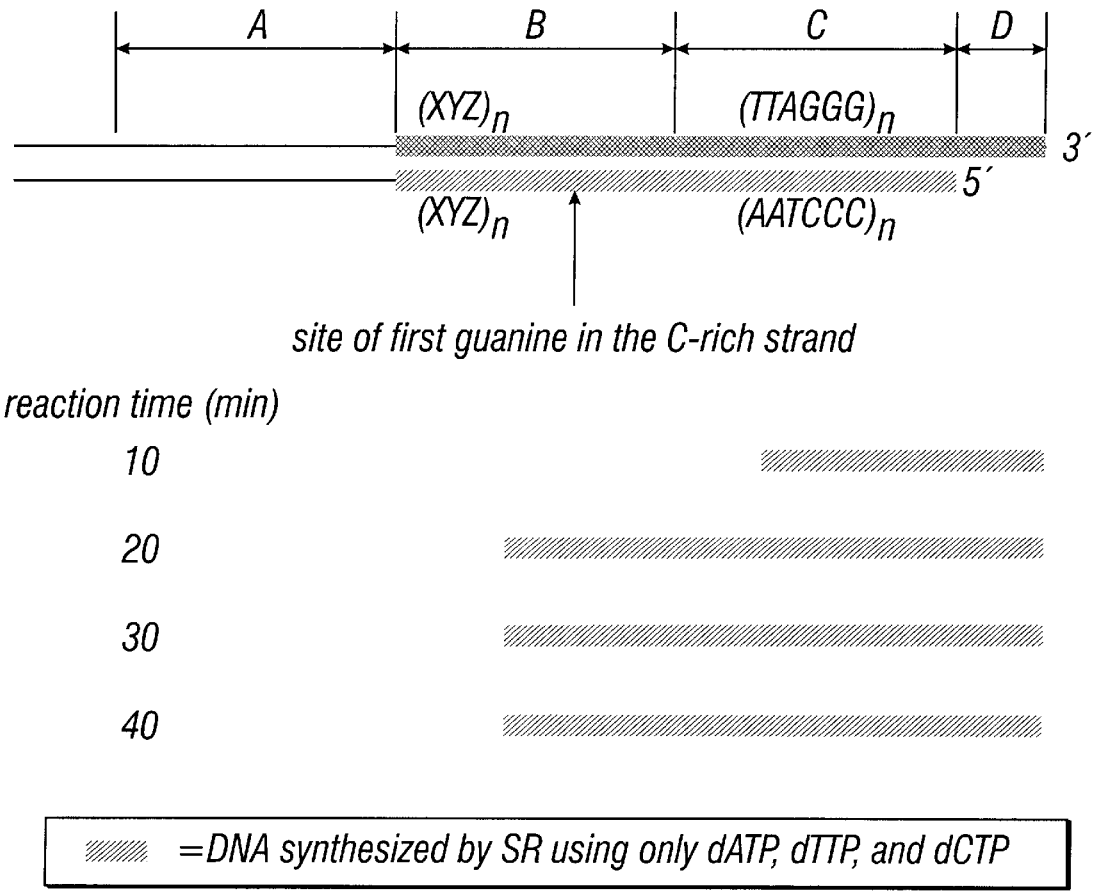
FIG. 12. Schematically shows the functional parts of telomeres, and determination of telomere length by using the PENT reaction. The top panel shows a terminal restriction fragment of a chromosome containing a telomere, with A representing the region of the chromosome that does not contain restriction sites and does not contain repetitive DNA; B representing the region that contains some repetitive DNA and that might include variants of the telomeric sequence (this region is not thought to be a functional part of the telomere); C representing the functional telomeric sequence, with the repetitive sequence $(TTAGGG)_n$; and D representing the single-stranded G-tail $(TTAGGG)_n$. The subtelomeric region is classified as regions A and B. The site of the first guanine in the C-rich strand is indicated. The bottom panel shows the DNA synthesized by the PENT reaction using only dATP, dTTP and dCTP, carried out for 10, 20, 30 and 40 minutes.

While the successful use of the methods of the present invention does not depend on a precise understanding of the mechanism of telomere shorting, the present invention contemplates synthesis at an unexpected base, specifically at the first point at which a guanosine is present in the "C-rich strand" within the unique sequence adjacent to the telomeres near the right-most end of fragment A, or within region B (see the arrow in FIG. 12). This mapping reaction has the same basic characteristics of the sequencing reactions, described above, except that termination is achieved when the polymerase is directed to incorporate a guanine into the growing strand, and the analysis is performed by low resolution electrophoresis of high molecular weight DNA product on an agarose gel, as opposed to sequencing which employs single base-resolved electrophoresis on a polyacrylamide gel.

More specifically, when only three natural nucleotides is provided to the polymerase, specifically dATP, dTTP, and dCTP, elongation will proceed unimpeded, copying all of the G-rich strand of the telomeric sequence, (TTAGGG)n. Termination will occur however, the first time that a guanosine appears in the C-rich strand, which will happen within a few bases of unique-sequence DNA, in region A, or perhaps within the telomere-like sequences that might exist in region B (FIG. 12). In other words, elongation will stop only when a specific type of defect occurs in the sequence. When such a cytosine is present the polymerase will be unable to add a new base due to the fact that dGTP is not present in the reaction, or an incorrect base will be incorporated. To optimize the reaction with Taq or to use other enzymes, with proofreading activities, a certain concentration of ddGTP (to be optimized) can be added to the reaction mixture to insure a full stop of elongation.

The length of the synthesized DNA is measured in order to determine how far from the chromosome terminus the termination event has occurred. The advantage of this general technique is that it can determine the total length of regions C+D+(a fraction of region B), without being sensitive to the chromosome-specific variations in the length of regions A and B. The reaction products are electrophoresed on a denaturing alkaline agarose gel to separate them according to molecular weight and detected by standard methods. If a label is incorporated only into the oligonucleotide primer, into the initial few bases of the strand replacement reaction, or into ddGTP, the distribution of number of telomeres of different molecular weights can be determined. This provides a relatively easy means to measure the lengths and abundance of telomeres with very short C+D regions, as might be found in geriatric individuals or in cancer cells.

EXAMPLE 5

Mapping of Telomere-Like Sequences in Region B

Figure 13:
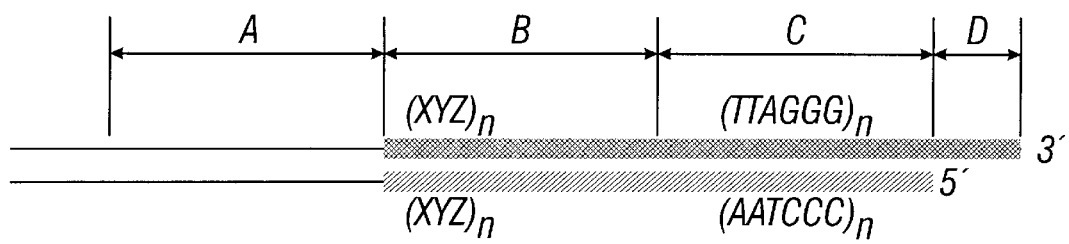
FIG. 13. Schematically sets forth one embodiment of the strand replacement method for measuring different distances from the termini of chromosomes. The top panel is reproduced from FIG. 12, showing the different regions of the terminal restriction fragment of a chromosome containing a telomere. The bottom panel shows the products of the PENT reactions with dUTP incorporation times of 0, 10, 20, 30 and 40 minutes, followed by a 1 minute PENT reaction incorporating dTTP. The thymidine-containing DNA synthesized by the PENT reaction is shown as a cross-hatched box, and the uridine-containing DNA synthesized by the PENT reaction is shown as a hatched line.

When all 4 dNTPs are present during a DNA polymerase replacement synthesis initiated from the end of chromosomes (as described above) the distance of the polymerase from the end will depend upon reaction time. As longer products are made, they will have 3' ends in regions D, C, B, and then A. There are many ways to use the strand replacement method of the present invention to determine the properties of the telomeric sequences specific distances from the terminus. For example, the strand replacement reaction can be initiated with a variable time of incorporation of dUTP, dGTP, dCTP, and dATP, followed by removal of the dUTP and replacement with dTTP and continuation of the strand replacement reaction for a fixed time. The products are schematically shown in FIG. 13. Subsequently, the uridine bases can be destroyed using deoxyribouridine glycosylase and heat, leaving only the DNA bases added at the end of the reaction, which are different distances from the termini of the chromosomes. This DNA can be hybridized to probes containing $(TTAGGG)_n$ and washed at different stringencies to detect whether the DNA has the $(TTAGGG)_n$ sequence, or a variant sequence. Alternatively oligonucleotide probes with different sequences can be hybridized to the SR products and washed under stringent conditions to search for specific variant sequences. In principle the products of strand replacement reactions for different times can be combined in the same sample, electrophoresed under denaturing conditions to separate the products according to molecular weight (i.e., with 3' ends located different distances from the chromosome termini), the DNA blotted to filter, the dUTP sites destroyed, and the remaining DNA hybridized to different probes to determine the nature of the DNA sequences different distances from the end. In principle, even single-base variations in the sequences of the glycosylase-resistant fragments could be detected by hybridizing the SR products to labeled telomere sequence oligonucleotides such as $(TTAGGG)_4$ (SEQ ID NO:6), followed by cleavage of the oligonucleotide at any mismatched sites using any one of a number of single-base mutation detection reagents, such as E. coli endo IV. The cleaved oligonucleotides can be detected by gel electrophoresis or by loss of energy transfer between fluorescent groups at the ends of the oligonucleotides. This type of reaction lends itself to automation.

In one embodiment, the strand replacement reaction is performed from the beginning in the presence of the 4 normal dNTPs. All that is required is the separation of the SR products from the genomic DNA. As in the previous paragraph, the products of many times of strand replacement can be combined into one sample, which can be separated by molecular weight, hybridized to the oligonucleotide, transferred to a filter, washed to remove unbound oligonucleotides, and cleaved for detection of mismatched bases located at different distances from the ends of the telomeres. Alternatively, the sequence purity at a specific distance from the end can be mapped by detecting variations from the exact 6 base repeat of thymine along the SR product strand. In this assay, after a controlled time of strand replacement in the presence of dCTP, dATP, dGTP, and a controlled ratio of dUTP to dTTP, the nucleotides are removed and replaced with dCTP, dATP, dGTP, and a controlled ratio of dTTP and radioactively- or fluorescently-labeled ddTTP. All SR products would then terminate with a labeled 3' dideoxy thymidine. Degradation of the DNA using deoxyribouridine glycosylase and heat would then terminate the other ends of the products at positions containing thymidine. For reactions terminating in regions of the chromosomes with pure $(TTAGGG)n$ tracts the labeled DNA fragments would form a 6 base ladder on a sequencing gel. For regions with sequence variations that did not retain the perfect 6 base repeat of thymidine, the sequencing gels would exhibit loss of the 6 base ladder. The best method to detect sequence variations within the telomeres will depend upon the nature of the variations found, whether they involve occasional guanines in the 5' strands, non-guanine substitutions for the normal repeat, or variations in the number of bases within some of the repeats. The nature of the actual sequence defects in human telomeres has not been studied in any detail. The methods of mapping of the present invention can be applied to determining the types of sequence defects present within telomeres in normal and abnormal human cells. For example, the DNA synthesized different distances from the ends of telomeres can be cloned and sequenced by standard methods to discover the actual sequence variants present.

EXAMPLE 6

Sequencing Double-Stranded DNA Using ddNTP-Terminated Strand Replacement Reaction A strand replacement sequencing reaction was performed on a linear, double-stranded plasmid template using Taq polymerase, $^{32}P$ radioactively labels, and polyacrylamide electrophoresis. The study involved a) DNA preparation, b) strand replacement, c) and gel electrophoresis.

A) DNA Preparation

40 µg of plasmid pUC19 (New England Biolabs) was digested 2.5 h at 37° C. with 200 units of Bam H1 (Boehringer Mannheim Biochemicals, "BMB") in 200 µl of 0.1 × BMB "restriction buffer B." The fraction of linearized plasmid was checked by electrophoresing 2 µl of the restricted DNA solution on a 1% agarose gel. The termini of the restricted plasmid were dephosphorylated in a 30 min reaction at 37° C. with 188 µl of the restricted DNA (39.5 µg), 23 µl of 10× alkaline phosphatase buffer (BMB), 5 µl of shrimp alkaline phosphatase (BMB), and 2 µl $H_2O$. The solution was then heated to 70° C. for 15 min to inactivate the alkaline phosphatase. The DNA was precipitated by adding 5 μl glycogen (10 μg/μl), 23 μl 3 M sodium acetate (pH 5.2), and 2.5 volumes 100% ethanol, and stored overnight at −70° C. The DNA was pelleted 15 min at 13,000 g and the pellet washed twice with cold 70% ethanol. The DNA was resuspended in 70 μl H$_2$O.

The DNA in 67.8 μl was mixed with 7.2 μl of double-stranded adaptor oligonucleotide (25 pmol/μl), 20 μl of 5× ligation buffer (BMB), and 5 μl (1 unit/μl) T4 DNA ligase (BMB). The ligation reaction took place overnight at 14–16° C. The ligase was inactivated at 70° C. for 15 min. The ligation substrates and products had the following structure:

```
Before ligation: pUC19      Bam HI - Adaptor

5'---GTACCCGGG-OH           P-GATCGACGAUACCGUGGACCUCGTTTTT 3'OH

3'---CATGGGCCCCTAG-OH       OH-TGCTATGGCACCTGGAGCAAAA 5'OH

After ligation:

5'------GTACCCGGGGATCGACGAUACCGUGGACCUCGTTTTT 3' OH

3'------CATGGGCCCCTAG TGCTATGGCACCTGGAGCAAAA 5' OH

*1 nucleotide gap
```

After ligation, 98 μl (39 μg) pUC19 was digested for 2.5 h at 37° C. with 16 μl (10 units/μl) Pst I, 30 μl buffer H (buffer H from BMB), and 156 μl H$_2$O, in order to remove the adaptor oligonucleotide from one end of the molecule. This insured that the strand replacement reaction would initiate at one end of the template. Aliquots of the DNA were analyzed to insure that ligation and restriction had been complete. The 2.7 kb ligated BamH I/Pst I pUC19 fragment was purified on 1% low melting agarose. The gel band (1.6 ml) was excised from the gel and incubated for 10 min at 65° C., and then incubated with 2 h at 45° C. with 10 μl agarase (1 unit/μl), 66 μl 25× agarase buffer (BMB). The sample was mixed with 166 μl of 3 M sodium acetate (pH 5.2), mixed, and spin at 13,000 g for 10 min. The supernatant was spun a second time for 10 min and the DNA extracted with phenol/chloroform once and chloroform twice. DNA was precipitated as above and suspended in 40 μl H$_2$O. Final yield was 15 μg DNA.

B) Strand Replacement

Two protocols were used for the SR sequencing reactions. The solutions and reagents for the sequencing reactions were as follows. The Buffers were: Buffer A: 100 mM Tris HCl, pH 8.0, 100 mM MgCl$_2$; and Buffer B: 500 mM Tris HCl, pH 8.9, 100 mM KCl, 25 mM MgCl$_2$. The Labeling Mix was 10 μM dGTP, 5 μM dCTP, 5 μM dTTP, 10 μM Tris HCl, pH 8.0. The Polymerization/Termination Mixes were as follows: G-terminating mix: 30 μM dNTP; 0.25 mM ddGTP; 0.37 mM MgCl$_2$; A-terminating mix: 30 μM dNTP; 1.0 mM ddATP; 1.12 mM MgCl$_2$; T-terminating mix: 30 μl M dNTP; 1.5 mM ddTTP; 1.62 mM MgCl$_2$; and C-terminating mix: 30 μM dNTP; 0.5 mM ddCTP; 0.62 mM MgCl$_2$; where 30 μM dNTP represents 30 μM of each of dGTP, dCTP, dATP and dTTP. The Labeling Solution was 2 μl $^{32}$P-dATP [3000 Ci/mmol (3.3 μM), Amersham], 2 μl 10 μM dATP, 1 μl 50 mM Tris HCl, pH 8.0. The Taq DNA Polymerase Dilution Buffer was 10 mM Tris HCl, pH 8.3, 50 mM KCl, 0.5% Tween 20, 0.5% Nonidet P40. The Stop/Loading Solution was 95% formamide, 20 mM EDTA, 0.05% Bromphenol Blue, 0.05% Xylene Cyanol. The Taq DNA Polymerase was AmpliTaq, (Cat.# N801-0060, Perkin Elmer), and the nucleotides were GeneAmp dNTPs, 10 mM, (Cat.# N808-0007, Perkin Elmer) and ddNTPs (Cat.# 775 304, Boehringer Mannheim).

The first protocol details sequencing using [α-$^{32}$P] dATP for the incorporation of label. To insure that all the strands were bound to primer, the DNA was hybridized under non-denaturing conditions to the primer oligonucleotide 5'-AAAACGAGGTCCACGGTA TCGT-3' (SEQ ID NO:7). To do this 0.2 pmol pUC19 DNA (0.17 pmol/μl or 0.3 μg/μl) was added to 0.4 pmol primer (0.1 pmol/μl), 1 μl Buffer A or 2 μl of Buffer B, and H$_2$O to make a total of 10 μl. The mixture was heated at 65° C. for 5 min, then at 37° C. for 30 min. To one tube was added 2 μl of the labeling mix, 2 μl of the labeling solution, 1 μl Taq DNA polymerase (diluted 2 times with Taq dilution buffer), and 5 μl H$_2$O. The mixture was incubated at 37° C. 5 μl aliquots were taken after 1 min, 2 min, 5 min, and 10 min of the labeling reaction. Then 2 μl of the "A"-terminating mix were added to 4 μl of labeled DNA (after 1, 2, 5 and 10 min reaction) in a 0.5 ml tube, covered with mineral oil and incubated at 55° C. for 10 min. The reaction was stopped by adding 4 μl of the Stop/Loading solution. Samples were heated at 95° C. for 3 min, cooled at 4° C. and loaded on the sequencing gel.

The second protocol details sequencing using a kinase $^{32}$P-labeled primer, end labeled using [γ-32P] ATP. Prior to initiating strand replacement, a mix was made comprising 3 μl pUC19 DNA (0.5 pmol), 2 μl of $^{32}$P-kinase labeled primer (1 pmol), 1 μl Buffer A or 3 μl Buffer B, 9 μl 10 mM Tris HCl, pH 8.0 (if Buffer A) or 11 μl H$_2$O (if Buffer B). The mixture was heated at 65° C. for 5 min, and then at 37° C. for 30 min. To initiate strand replacement, 1 μl of Taq DNA polymerase (diluted 2 times with the dilution buffer) was added to the mixture at room temperature to create a second mixture. Thereafter, the following solution were added to 4 μl of this second mixture: 2 μl of the "G-terminating mix" ("G"-tube); 2 μl of the "A-terminating mix" ("A"-tube); 2 μl of the "T-terminating mix" ("T"-tube); 2 μl of the "C-terminating mix" ("C"-tube); and 2 μl of the 30 mM dNTP mix ("dNTP"-tube). The "G", "A", "T", "C" and "dNTP"-tubes were incubated at 55° C. for 10 min. The reaction was stopped by adding 4 μl of the Stop/Loading solution, and the reaction was heated at 95° C. for 3 min, cooled at 4° C., and loaded on sequencing gel.

C) Gel Electrophoresis

Figures 14A, 14B:
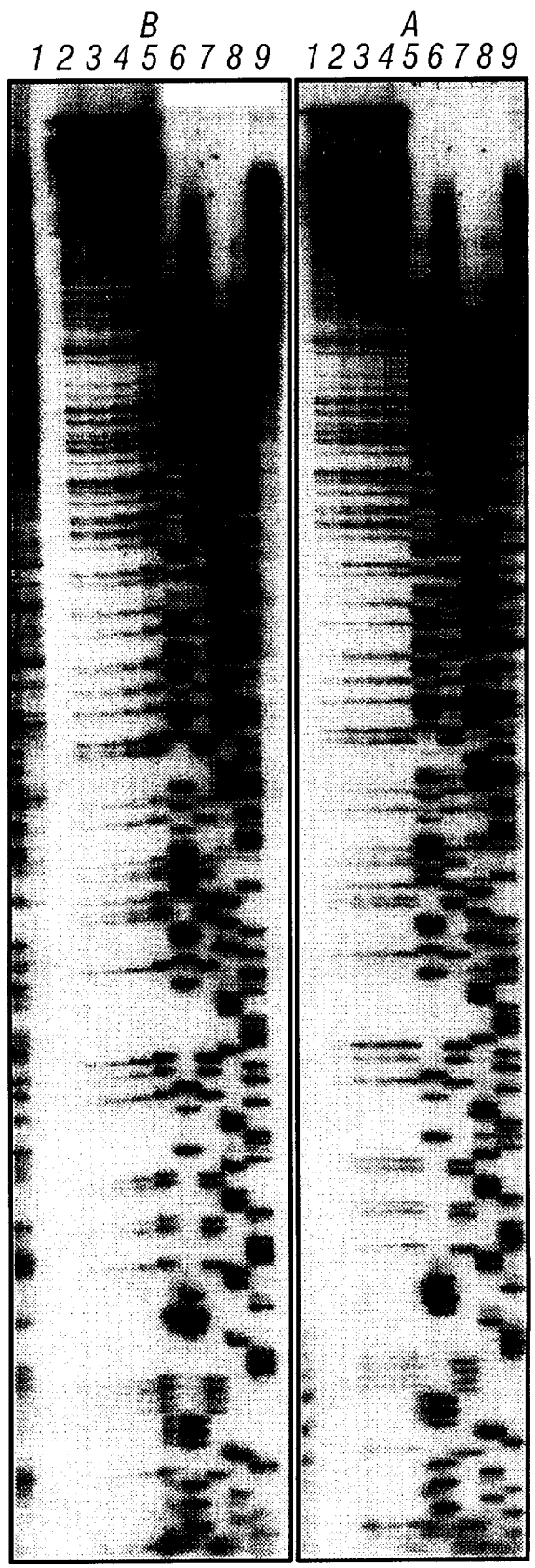
FIG. 14A and FIG. 14B. Shows the sequencing gel results following strand replacement performed according to the present invention.

A standard denaturing 6% polyacrylamide sequencing gel was run under standard conditions (Ausubel et al., 1991). The $^{32}$P-labeled SR products were detected by autoradiography on film, exposed ~8 h at room temperature. FIG. 14A and FIG. 14B are images of the autoradiograms. FIG. 14B represents the reactions performed in buffer B. Lanes 1–4 represent DNA labeled with $^{32}$P dATP for 1 min, 2 min, 5 min, and 10 min, respectively. Each of these reactions incorporated ddATP. The bands are at the positions expected for adenines in the pUC19 sequence. Very little background is found between bands and the bands have uniform intensity. At this ratio of ddATP to dATP, the strand replacement reaction continued on to high molecular weight, beyond the resolution of the gel. Lanes 5–8 correspond to DNA labeled using kinase-labeled primer from different termination tubes, "G-tube", "A-tube", "T-tube", and "C-tube", respectively. Each of these lanes had bands corresponding to ddNTP termination at the cognate base position in the double-stranded template DNA. The ddNTP mixes have not been optimized to give the same radioactivity in each lane, however all lanes show termination at the ddNTP sites without detectable background between lanes due to premature termination of the SR sequencing reaction. Band intensities are very uniform from site to site within lanes, except where bands overlap due to homopolymeric tracts. Lane 9 corresponds to DNA labeled using kinase-labeled primer in the reaction of the "dNTP tube." This reaction shows no termination of the strand replacement reaction at low molecular weights, illustrating lack of detectable premature termination of the product. FIG. 14A represents the same reactions seen in the left panel, with the exception that the reactions were run in buffer A. Under these conditions there are detectable amounts of premature termination, even in lane 9, which represented the "dNTP tube." Thus the strand replacement synthesis from a double-stranded template can be used to sequence DNA.

EXAMPLE 7

"Base Walking" Sequencing Reactions

Multiple base sequencing involves specifically labeling DNA molecules with 3' ends terminated at specific combinations of two or more bases. This process involves one or more cycles of "base walking" with a specific series of bases followed by a "termination" reaction with a selected labeled nucleotide. For example, to label strands terminated with the dinucleotide AT, there would be a single A-walk reaction followed by a T-termination reaction. The two critical steps of an N-walk (where N is one of the four base types) are a "dd(-N)-blocking" (dideoxy minus N-blocking) reaction, followed by removal of unincorporated nucleotides, and then followed by an "N-extension" reaction. The dd(-N)-blocking reaction consists of reacting the 3' OH ends with polymerase and all three of the dideoxyribonucleotide bases except the specified N base. The N-extension reaction consists of reacting the 3' OH ends with the specified N base.

Single N-extension reactions with different dNTPs and blocking reactions with mixtures of three different ddNTPs were performed on model oligonucleotide templates DNA using ThermoSequenase™ (Amersham), $^{32}$P radioactively labeled primers, and polyacrylamide electrophoresis. The single-base extension reactions were performed using phosphorothiolated bases, which are incorporated with the same efficiency and fidelity as normal nucleotides by DNA polymerase. Therefore, the same results are obtained if normal nucleotide bases are used. The experiments involved reagent preparation, N-extension reactions, dd(-N) blocking reactions, and gel electrophoretic analysis of the products. The results directly show that the blocking and extension reactions are highly specific and efficient. The high specificity of the blocking reactions show that termination reactions are also specific and efficient. Thus the results show that the basic steps of multiple-base sequencing have been achieved.

A. Reagent Preparation

The oligonucleotides used for preparation of the model constructs had the following structure: Oligo-template, 5'-CAGGATGTGACCCTCCAGCACATAGGTCTACG-3' (SEQ ID NO:8); Primer A, 3'-GGTCGTGTATCCAGATGCCAG-5' (SEQ ID NO:9); Primer G, 3'-GAGGTCGTGTATCCAGATGCCAG-5 (SEQ ID NO:10); Primer T, 3'-GGGAGGTCGTGT ATCCAGATGCCAG-5' (SEQ ID NO:11); Primer C, 3'-ACTGGGAGGTCGTGTATCCAGA TGCCAG-5' (SEQ ID NO:12). 10 pmol of each oligonucleotide primer A, T, G and C were separately 5'-end labeled for 10 min at 37° C. using 10 U T4 kinase (BRL), 10 μCi γ-ATP (Amersham) and 1×T4 kinase buffer (BRL) in 25 μl volume. Reaction was terminated by adding 0.5 μl of 0.5 M EDTA and 74.5 μl H$_2$O and heating for 10 min at 90° C. (final concentration—100 nM). 10 μl (1 pmol) of each $^{32}$P-labeled primer A, T, G, and C were mixed with 40 μl of 10 μM oligo-template, 10 μl of GeneAmp 10×PCR buffer II (500 mM KCl, 100 mM Tris-HCl, pH 8.3; Perkin Elmer), 6 μl 25 mM MgCl$_2$, and 4 μl H$_2$O. The mixture was heated to 85° C. and then annealed during slow overnight cooling to room temperature. The mixed construct was stored at −20° C.

The buffers used were as follows: 1×Walk buffer (50 mM KCl, 10 mM Tris-HCl, pH 8.3, 1.5 mM MgCl$_2$); TE buffer (10 mM Tris-HCl, pH 7.5, 0.1 mM EDTA); "Stop" solution (2.25 M sodium acetate, 63 mM EDTA, 2.5 mg/ml glycogen (Boehringer Mannheim Biochemicals, "BMB")). The dNTP mixes used were: "10 μM α-S-dATP": 10 μM α-S-dATP in 1×Walk buffer; "10 μM α-S-dTTP": 10 μM α-S-dTTP in 1×Walk buffer; "10 μM α-S-dGTP": 10 μM α-S-dGTP in 1×Walk buffer; and "1 μM α-S-dCTP": 1 μM α-S-dCTP in 1×Walk buffer.

The Balanced dd(-N) mixes were as follows: Balanced stock "dd(-A) mix": 400 μM ddTTP, 400 μM ddGTP, 50 μM ddCTP in 1×Walk buffer; Balanced stock "dd(-T) mix": 1000 μM ddATP, 400 μM ddGTP, 50 μM ddCTP in 1×Walk buffer; Balanced stock "dd(-G) mix": 1000 μM ddATP, 400 μM ddTTP, 50 μM ddCTP in 1×Walk buffer; and Balanced stock "dd-C) mix": 1000 μM ddATP, 400 μM ddTTP, 400 μM ddGTP in 1×Walk buffer. To prepare "1/10 dd(-N)", "1/100 dd(-N)", "1/1000 dd(-N)", and "1/10000 dd(-N)" mixes balanced stock dd(-N) solutions were diluted 1:10, 1:100, 1:1000, and 1:10,000 with 1×Walk buffer. The Unbalanced dd(-N) mixes were as follows: Unbalanced "dd(-A) mix": 200 nM ddTTP, 200 nM ddGTP, 20 nM ddCTP in 1×Walk buffer; Unbalanced "dd(-T) mix": 200 nM ddATP, 200 nM ddGTP, 20 nM ddCTP in 1×Walk buffer; Unbalanced "dd(-G) mix": 200 nM ddATP, 200 nM ddTTP, 20 nM ddCTP in 1×Walk buffer; and Unbalanced "dd(-C) mix": 200 nM ddATP, 200 nM ddTTP, 200 nM ddGTP in 1×Walk buffer.

B. N-extension Reactions

Single-base polymerase extension reactions were demonstrated using the labeled mixed construct, ThermoSequenase (Amersham), dNTPs and α-S-dNTPs (Amersham). 45 μl of the mixed construct was supplemented with 67.5 μl of 1×Walk buffer and 7 μl of ThermoSequenase (diluted 1:32 with ThermoSequenase dilution buffer, Perkin Elmer). 25 μl aliquots of this solution were placed into four 0.5 ml PCR tubes, preheated for 2 min at 45° C. and combined with 25 μl of preheated "10 μM α-S-dATP", "10 μM α-S-dTTP", "10 μM α-S-dGTP", or "1 μM α-S-dCTP" solutions. The reaction was performed for 10 min at 45° C., stopped by adding 8 μl of "Stop" solution and the constructs were ethanol precipitated. Recovered oligonucleotide pellets were dissolved in 10 μl of TE buffer.

C. dd(--N)-blocking Reactions and Subsequent Walking

"dd(-N)-blocking" reactions were demonstrated using the same mixed construct, ThermoSequenase and 4 mixtures of three ddNTPs (BMB). In the first experiment, 36 µl of the mixed labeled construct was supplemented with 414 µl of 1×Walk buffer, and 18 µl of ThermoSequenase (diluted 1:32). 25 µl aliquots of this solution were placed into sixteen 0.5 ml PCR tubes, preheated for 2 min at 45° C. and combined with 25 µl of preheated balanced "dd(-N) mixes" of different concentration (1/10, 1/100, 1/1000, and 1/10,000 of stock concentration). The reactions were performed for 5 min at 45° C., stopped by adding 8 µl of "Stop" solution and the constructs were ethanol precipitated.

In the second experiment 22.5 µl of the mixed labeled construct was supplemented with 90 µl of 1×Walk buffer and 8 µl ThermoSequenase (diluted 1:32). 25 µl aliquots of this solution were placed into four 0.5 ml PCR tubes, preheated for 2 min at 45° C. and combined with 25 µl of preheated non-balanced "dd(-N) mixes." The reactions were performed for 10 min at 45° C. and processed as described before. Recovered oligonucleotide pellets were washed with 80% ethanol, dried, and dissolved in 10 µl of TE buffer.

To complete the N-walk reaction cycle, extension reactions were performed on the dd(-N)-blocked oligonucleotides. To show that the unblocked DNA ends could be extended by DNA polymerase, one half (5 µl) of each product of the blocking experiment above was supplemented with Walk buffer, 100 µM dATP, 100 µM dTTP, 100 µM dGTP, and 10 µM dCTP, and 1 U of ThermoSequenase, incubated for 15 min at 45° C., and stopped by adding 1 µl of 100 mM EDTA.

D. Gel Electrophoretic Analysis

Figure 24:
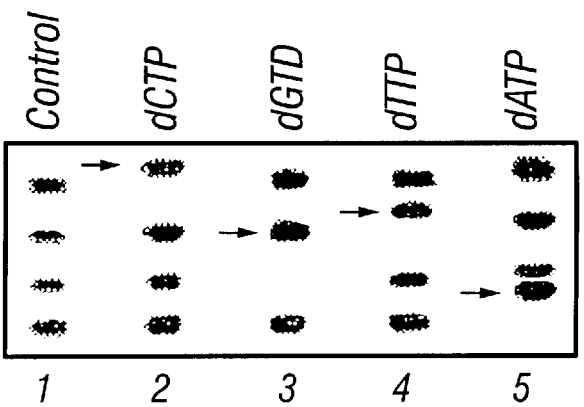
FIG. 24. The results of single-base extension experiment analyzed by polyacrylamide gel electrophoresis. Lane 1 represents primer A (21 bases), primer G (23 bases), primer T (25 bases), and primer C (28 bases) before extension. Lanes 2–5 represent products of single-base extension reactions in the presence of 1 µM α-S-dCTP, 10 µM α-S-dGTP, 10 µM α-S-dTTP, and 10 µM (α-S-dATP, respectively. Arrows indicate the positions of elongated products.

A standard denaturing 16% polyacrylamide sequencing gel was run under standard conditions (Ausubel et al,. 1991). The $^{32}$P-labeled oligonucleotide polymerase extension products were detected and quantitated using a Molecular Dynamics 400 A PhosphoImager and ImageQuant software. FIG. 24 shows the results of single-base extension experiment. Lane 1 represent primer A (21 bases), primer G (23 bases), primer T (25 bases), and primer C (28 bases) before extension. Lanes 2–5 represent products of single-base extension reactions in the presence of 1 µM α-S-dCTP, 10 µM α-S-dGTP, 10 µM α-S-dTTP, and 10 µM α-S-dATP, respectively. Arrows indicate the positions of elongated products. As expected primer G incorporated two guanine bases and migrates as a 25-mer, while each of the other primers were extended by a single base. The results presented in FIG. 24 show that under specific conditions a single-base extension can be performed near completion without any noticeable misincorporation into incorrect positions.

Figure 25:
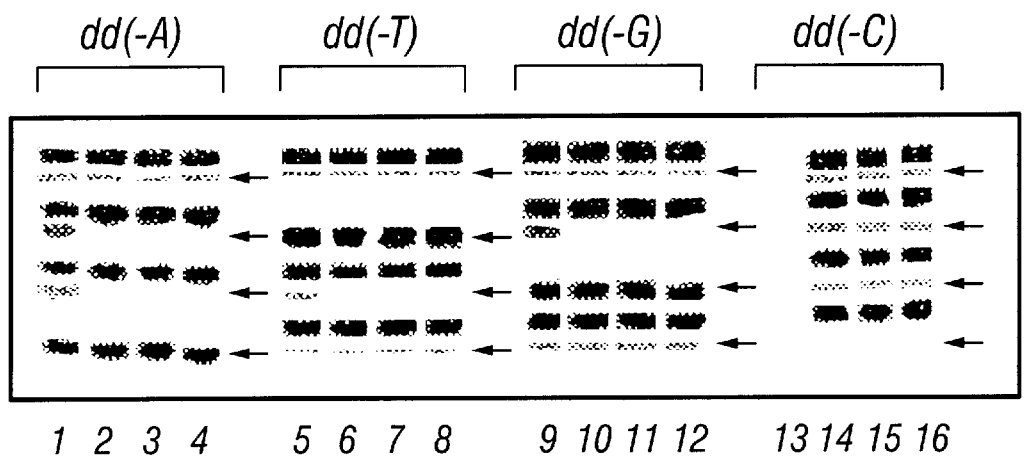
FIG. 25. The results of the dd(-N)-blocking reactions using different concentrations of "dd(-A) mix" (lanes 1–4), "dd(-T) mix" (lanes 5–8). "dd(-G) mix" (lanes 9–12), and "dd(-C) mix" (lanes 13–16) analyzed by polyacrylamide gel electrophoresis. Lanes 1, 5, 9, and 13 correspond to 1/10,000 of stock concentration; lanes 2, 6, 10, and 14 correspond to 1/1000 of stock concentration; lanes 3, 7, 11, and 15 correspond to 1/100 of stock concentration; and lanes 4, 8, 12, and 16 correspond to 1/10 of stock concentration of "dd(-N) mixes."

FIG. 25 shows the results of the dd(-N)-blocking reactions using different concentrations of "dd(-A) mix" (lanes 1–4), "dd(-T) mix" (lanes 5–8), "dd(-G) mix" (lanes 9–12), and "dd(-C) mix" (lanes 13–16). Lanes 1, 5, 9, and 13 correspond to 1/10,000 of stock concentration; lanes 2, 6, 10, and 14 correspond to 1/1000 of stock concentration; lanes 3, 7, 11, and 15 correspond to 1/100 of stock concentration; and lanes 4, 8, 12, and 16 correspond to 1/10 of stock concentration of "dd(-N) mixes." The results indicate that the dd(-N)-blocking reactions are highly specific and very efficient. Practically no primers remain unblocked except the selected primers, which, in turn, show no detectable misincorporation of ddNTPs.

Figure 26:
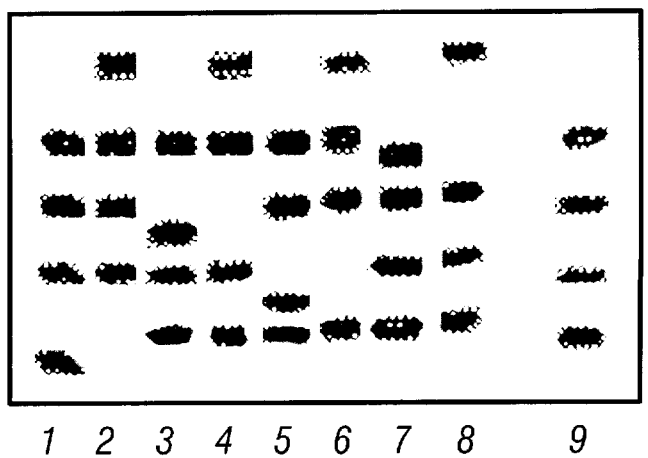
FIG. 26. Extension of those primers that should still have 3' OH groups after the blocking reactions. Lanes 1, 3, 5, and 7 contain the oligonucleotide mixture after the blocking reactions with "dd(-A)", "dd(-T)", "dd(-G)", and "dd(-C)" mixes, respectively. Lanes 2, 4, 6, and 8 contain the products of polymerase extension of the DNA in lanes 1, 3, 5, and 7, respectively. Lane 9 contains unextended primers.

FIG. 26 shows extension of those primers that should still have 3' OH groups after the blocking reactions. Lanes 1, 3, 5, and 7 contain the oligonucleotide mixture after the blocking reactions with "dd(-A)", "dd(-T)", "dd(-G)", and "dd(-C)" mixes, respectively. Lanes 2, 4, 6, and 8 contain the products of polymerase extension of the DNA in lanes 1, 3, 5, and 7, respectively. Lane 9 contains unextended primers. Each of the primers that was not blocked with the dideoxyribonucleotide mix could be efficiently extended to the end of the template strand by DNA polymerase. Taken together with the results of the N-extension reactions shown in FIG. 24 and FIG. 25, the results shows that base walking and termination (and therefore multiple base sequencing reactions) are feasible.

EXAMPLE 8

DNA Random Nicking using Fe/EDTA and DNase I

Random nicking reactions were performed on a circular, double-stranded plasmid and linear PCR DNA molecules, using a chemical Fenton reaction for creation of hydroxyl radicals (Hertzberg and Dervan, 1984; Price et al., 1992), and enzymatic treatment with DNase I in the presence of $Mn^{++}$ cations (Campbell et al, 1980). The radioactively labeled products of cleavage were analyzed by gel electrophoresis.

A. DNA Preparation

A 489 bp pUC19 DNA fragment (bp 1714–1225) was amplified from pUC19 plasmid DNA (New England BioLabs) using $^{32}$P labeled pUC19 primer 2 (5'-TTATCTACACGAA GGGGAGTCAGA-3'; SEQ ID NO:14) and biotinylated pUC19 primer 1 (5' Biotin-GGTAACA GGATTAGCAGAGCGAGG-3'; SEQ ID NO:13). To radioactively label primer 2, 1 µl of 10 µM pUC19 primer 2 was combined with 2.5 µl 10×Kinase buffer (BMB), 4 µl $^{32}$P γ-ATP (Amersham), 16.5 µl $H_2O$, and 1 µl T4 kinase (BMB), incubated at 37° C. for 1 h, stopped by adding 3 µl 100 mM EDTA, heated for 10 min at 75° C. and adjusted with 22 µl $H_2O$ to final volume of 50 µl.

To perform PCR amplification, 50 µl of $^{32}$P labeled primer 2 was combined with 4 µl of 10 µM biotinylated primer 1, 20 µl of GeneAmp 10×PCR buffer (500 mM KCl, 100 mM Tris-HCl, pH 8.3, 15 mM $MgCl_2$, and 0.01% gelatin; Perkin Elmer), 3 µl pUC19 DNA (1 ng/µl), 8 µl 2.5 mM dNTP, 114 µl $H_2O$ and 1 µl AmpliTaq (5 U/µl; Perkin Elmer). Amplifications were performed in two 100 µl volumes using DNA Thermo Cycler (Perkin Elmer) and 20 cycles of polymerization reaction comprising of: 30 sec of denaturing at 94° C., 30 sec of primer annealing at 62° C., 1 min of extension at 72° C. Amplified DNA was precipitated with ethanol, dried and dissolved in 50 µl TE buffer.

To immobilize DNA, 50 µl of paramagnetic streptavidin-coated beads (Dynabeads M-280 Streptavidin; Dynal) were washed 3 times using magnetic separator (Life Technologies) and 1×B & W buffer, resuspended in 50 µl of 2×B & W buffer, mixed with 50 µl of PCR amplified DNA fragment, and incubated at 37° C. for 1 h using occasional mixing by gently tapping the tube. Immobilized DNA was washed 3 times with 1×B & W buffer and finally resuspended in 50 µl of TE buffer.

The buffers used are as follows. GeneAmp 10×PCR buffer: 500 mM KCl, 100 mM Tris-HCl, pH 8.3, 15 mM $MgCl_2$, and 0.01% gelatin; Perkin Elmer). 2×B & W buffer: 10 mM Tris-HCl, pH 7.5, 1 mM EDTA, 2.0 M NaCl. TE buffer: 10 mM Tris-HCl, pH 7.5, 0.1 mM EDTA. 1×DNase I buffer: 50 mM Tris-HCl, pH 7.5, 1 mM $MnCl_2$, 100 mg/ml BSA. "Stop" buffer: 100 mM thiourea, 1 mM EDTA.

B. Chemical Nicking of Immobilized DNA with Fe/EDTA

25 µl of immobilized DNA was additionally washed 2 times with 50 µl of 10 mM Tris-HCl buffer, pH 7.5, and resuspended in 75 µl of the same buffer at the bottom of 1.5 ml Eppendorf tube. 5 µl were taken as a control. 10 µl of freshly-prepared Fe/EDTA complex (20 mM ammonium iron(II) sulfate/40 mM EDTA), 10 μl of 10 mM sodium ascorbate and 10 μl of 0.3% $H_2O_2$ were mixed quickly on the tube wall and combined with 70 μl of the immobilized DNA (Price and Tullius, 1992). The reaction was performed at room temperature and 25 μl aliquots were removed after 15 sec, 30 sec, 1 min, and 2 min of incubation with Fe/EDTA. The reaction was stopped by adding 100 μl of "Stop" buffer. The suspension was washed 3 times with "Stop" buffer followed by 2 washes with TE buffer.

C. Enzymatic Nicking of Immobilized DNA with DNase I

25 μl of immobilized DNA was additionally washed 2 times with 50 μl of DNase I buffer and resuspended in 105 μl of the same buffer. 5 μl were taken as a control; 100 μl of the immobilized DNA was preincubated at 15° C. DNase I (1 mg/ml; BMB) was diluted 1:1,000,000 with DNase I buffer and 5 μl (50 pg) was added to DNA. The reaction was performed at 15° C. and 25 μl aliquots were removed after 1 min, 2 min, 5 min, and 10 min of incubation with DNase I and mixed with 25 μl of 100 mM EDTA. The suspension was washed 2 times with 1×B & W buffer followed by 2 washes with TE buffer.

D. Electrophoretic Separation and Analysis

Figure 27:
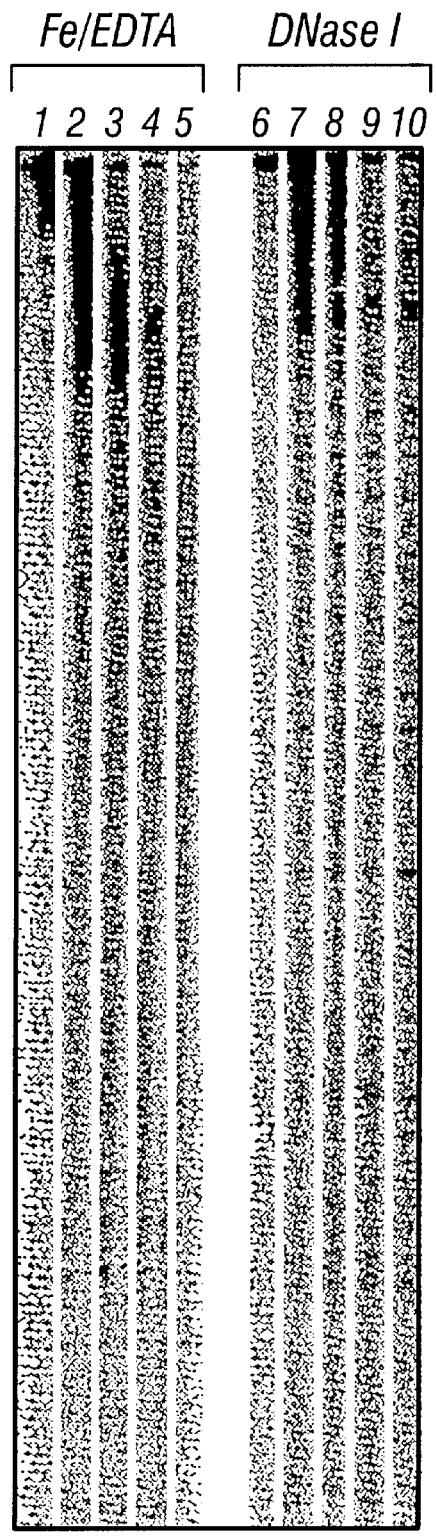
FIG. 27. Patterns of DNA degradation caused by Fe/EDTA and DNase I treatment are nearly random. Lanes 1, 2, 3, 4, and 5 correspond to 0, 15 sec, 30 sec, 1 min, 2 min of incubation of immobilized DNA with Fe/EDTA. Lanes 6, 7, 8, 9, and 10 correspond to 0, 1 min, 2 min, 5 min, 10 min of incubation of immobilized DNA with DNase I.

A standard denaturing 6% polyacrylamide sequencing gel was run under standard conditions (Ausubel et al., 1991). The $^{32}$P-labeled and nicked DNA products were detected and quantitated using a Molecular Dynamics 400A PhosphoImager and ImageQuant software. FIG. 27 shows that the patterns of DNA degradation caused by Fe/EDTA and DNase I treatment are nearly random. Lanes 1, 2, 3, 4, and 5 and 6, 7, 8, 9, and 10 correspond to 0, 15 sec, 30 sec, 1 min, 2 min, and 0, 1 min, 2 min, 5 min, 10 min of incubation of immobilized DNA with Fe/EDTA and DNase I, respectively.

EXAMPLE 9

Efficient Conditioning of Fe/EDTA Introduced Breaks and Random DNA Sequencing

Fe/EDTA treatments introduce 1 base DNA gaps with a phosphate group at the 3' end of the defect (Hertzberg and Dervan, 1984; Price and Tullius 1992). Different enzymatic reactions were tested, and it was found that the combined action of T4 DNA polymerase and exonuclease III can be efficiently used to repair the 3' ends and expose 3' hydroxyl (OH) groups effective for DNA polymerases.

A. Fe/EDTA Treatment of PCR Amplified and Plasmid DNA

Immobilized PCR amplified DNA (1 pmol) was processed with Fe/EDTA as described above in Example 8. 1 mg of pUC19 plasmid DNA was supplemented with 65 ml of 10 mM Tris-HCl, pH 7.5, placed at the bottom of 1.5 ml Eppendorf tube, and combined quickly with 10 ml Fe/EDTA (0.25 mM/0.5 mM), 10 μl 10 mM sodium ascorbate and 10 μl 0.3% $H_2O_2$. The reaction was performed at room temperature for 15 sec and stopped by adding 100 μl of "Stop" buffer (see Example 8). DNA was washed 2 times with "Stop" buffer and 2 times with TE buffer using Microcon 100 microconcentrator (Amicon) and recovered in 20 μl volume of $H_2O$.

B. Conditioning of Fe/EDTA-Introduced Breaks with Exonuclease III and T4 DNA Polymerase Four 1 μl (100 ng) aliquots of pUC19 DNA after Fe/EDTA treatment were mixed at 4° C. with 4 μl 5×T4 polymerase buffer (BMB), 1 μl 2.5 mM dNTP mix, 1 μl T4 DNA polymerase (1 U/μl; BMB), supplemented with 0, 0.1 U, 0.3 U, or 1 U of diluted exonuclease III (exo III; 100 U/μl; BMB), adjusted with $H_2O$ to 20 μl and incubated at 37° C. for 30 min. After inhibition of exo III by heating the samples for 10 min at 70° C., 1 μl of fresh T4 DNA polymerase was added and the reactions performed at 12° C. for 1 h. The reactions were stopped by adding 2.5 μl 100 mM EDTA and TE buffer to 200 μl, extracted with phenol/chloroform and ethanol precipitated. DNA pellets were recovered, washed with 70% ethanol, dried and dissolved in 10 μl of TE buffer.

In the second study, 1 pmol of immobilized PCR amplified DNA that had been Fe/EDTA treated for 15 sec (prepared as in the Example 8) was washed with 50 μl of 1×T4 DNA polymerase buffer (BMB) and resuspended in 100 μl of 1×T4 DNA polymerase buffer supplemented with 125 mM dNTP and 0.1 U of exo III. DNA was incubated for 20 min at 37° C. and, after adding 1 μl of fresh T4 DNA polymerase, for another 20 min at 15° C. The reaction was stopped by adding 2 μl 0.5 M EDTA and the DNA suspension was washed 2 times with 100 μl of 1×B & W buffer and 2 times with TE buffer.

C. Polymerase Extension Reactions

10 μl pUC19 DNA samples after Fe/EDTA treatment and conditioning with different amounts of exo III were supplemented with 20 μl of GeneAmp 10×PCR buffer, 8 μl 25 mM $MgCl_2$, 25 pmol (80 μCi) of $^{32}$P α-dCTP (Amersham), 53 μl $H_2O$ and 1 μl of AmpliTaq (Perkin Elmer). The reaction proceeded 5 min at 45° C. and 5 min at 55° C. and was stopped by adding 3 μl of 10×DNA loading buffer.

50 μl (1 pmol) of immobilized, Fe/EDTA treated and conditioned DNA was washed with 50 μl of GeneAmp 1×PCR buffer and aliquoted (15 μl) into tubes #2, 3 and 4. Tube #1 contained about 300 fmol of immobilized and washed but not treated PCR DNA. After removing the buffers with magnetic separator, tubes 1–4 were supplemented with 30 μl of GeneAmp 1×PCR buffer, containing 0.75 U AmpliTaq and 100 nM $^{32}$P α-dATP, 100 nM $^{32}$P α-dATP/200 nM cold α-dATP, 100 nM $^{32}$P α-dATP, and 33 nM $^{32}$P α-dATP, respectively. Samples were incubated at 45° C. for 10 min and then terminated with 1 μl 0.5 M EDTA, washed once with B & W buffer, once with TE and 2 times with 0.1 M NaOH. DNA was released from magnetic beads by heating at 95° C. in 10 μl of standard sequencing loading buffer and fast separation from the beads by magnetic separator.

D. Electrophoretic Analysis pUC19 DNA samples after Fe/EDTA treatment, conditioning and DNA polymerase labeling were run on 1% agarose gel in 1×TAE buffer, stained with ethidium bromide and analyzed using a cooled CCD camera. After this the DNA was electroblotted onto ZetaProbe (BioRad) nylon membrane and analyzed using PhosphoImager.

FIG. 28 shows the stained gel (panel A) and autoradiogram (panel B). Lanes 1 and 7 contain non-conditioned Fe/EDTA treated DNA; lanes 2 and 8 contain DNA conditioned with T4 DNA polymerase only; lanes 3 and 9 contain DNA conditioned with combined action of T4 DNA polymerase and 0.1 U exo III; lanes 4 and 10 contain DNA conditioned with combined action of T4 DNA polymerase and 0.3 U exo III; lanes 5 and 11 contain DNA conditioned with combined action of T4 DNA polymerase and 1 U exo III; lanes 6 and 12 contain DNA conditioned with combined action of T4 DNA polymerase and 3 U exo III. Very little incorporation of $^{32}$P α-dATP was detected in non-conditioned (lanes 1 and 7) and T4 polymerase conditioned (lanes 2 and 8) DNA samples. Incubation with a very small amount of exo III increases efficiency of DNA labeling 100 times, indicating efficient removal of 3' phosphate groups in Fe/EDTA treated DNA.

A standard denaturing 6% polyacrylamide sequencing gel was run under standard conditions (Ausubel et al,. 1991).

Figure 29:
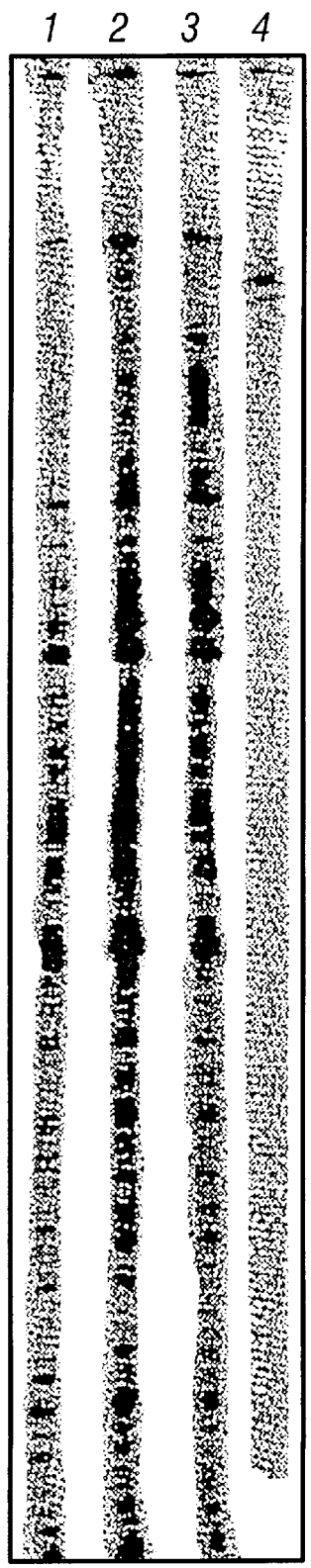
FIG. 29. Results of specific incorporation of $^{32}$P α-dATP into Fe/EDTA randomly nicked DNA. Lanes 1–3 correspond to labeling reactions performed at 30 nM, 100 nM, and 300 nM of α-dATP, respectively. Lane 4 corresponds to non-degraded control DNA incubated with 100 nM α-dATP.

Fe/EDTA treated, conditioned and $^{32}$P α-dATP-labeled PCR DNA products were detected and quantitated using a Molecular Dynamics 400A PhosphoImager and ImageQuant software. FIG. 29 shows results of specific incorporation of $^{32}$P α-dATP into Fe/EDTA randomly nicked DNA. Lanes 1–3 correspond to labeling reactions performed at 30 nM, 100 nM, and 300 nM of α-dATP, respectively. Lane 4 corresponds to non-degraded control DNA incubated with 100 nM α-dATP. The data demonstrate the feasibility of the random nick DNA sequencing method.

EXAMPLE 10

Additional Methods for Multibase Analysis

This example describes additional biochemical reactions that generate DNA fragments sutiable for multi-base sequence analysis. These techniques extend the earlier described "random nick" approach, as well as several reactions which utilize random double-stranded (rds) breaks.

Three steps are common for all the reactions described in this example. In the first step (step a), random double-stranded (rds) breaks are introduced in the DNA molecule by any of the methods described herein, including sonication, nebulization, irradiation, or enzymatic treatment, for example using DNase I in the presence of $Mn^{++}$. A combination of sonication and DNase I degradation is particularly preferred in certain aspects of the invention. It is preferred that the distribution of the double stranded breaks along the DNA molecule is essentially random.

In the second step (step b), the broken ends are conditioned or repaired to generate a 3' hydroxyl group, as described herein above, for example using T4 DNA polymerase. While in certain aspects of the invention this step can be eliminated, particularly when certain enzymatic treatments are used to generate the double stranded breaks, it is particularly important when non-enzymatic methods for creating double stranded breaks are used. Physical methods of creating double stranded breaks, such as sonication and nebulization, usually generate DNA ends which cannot be efficiently ligated to an adaptor (approximately 1% efficiency). Conditioning or repairing treatment increases the ligation efficiency from about 1% to about 10%, and by using a combination of T4 DNA polymerase and exonuclease III, as described herein above, the ligation efficiency can be increased to almost 100%.

Figures 30A, 30B:
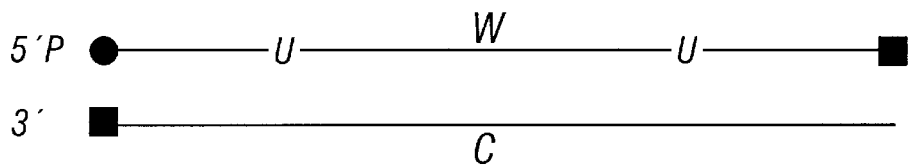
FIG. 30A and FIG. 30B.

In the third step (step c), the conditioned or repaired randomly broken ends are linked or attached to a double stranded oligonucleotide adaptor through ligation. An exemplary adaptor is the 3'-blocked oligonucleotide adaptor is depicted in FIG. 30A. Only the top (W) strand of this adaptor has a 5'-phosphate group that can be covalently linked to the 3' OH group of the repaired DNA ends. In certain aspects of the invention, an adaptor that has a blocking group, for example a dideoxy- or $NH_2$-group, at the 3' end of only the top (W) strand is contemplated for use. However, adaptor-adaptor ligation is possible, thus reducing the efficiency of ligating the adaptor to the repaired ends of the DNA molecule. Therefore, more preferred is an adaptor that is blocked by the presence of a blocking group at both 3' termini, which allows the concentration of adaptors to remain high during the ligation reaction and leads to very high efficiency of adaptor ligation to the blunt DNA ends. Additionally, the thymines in the W strand can be replaced by deoxyuracil, which allows for the destruction of the W strand of the adaptor using a combination of uracil DNA glycosylase (dU-glycosylase) and NaOH.

Figure 31:
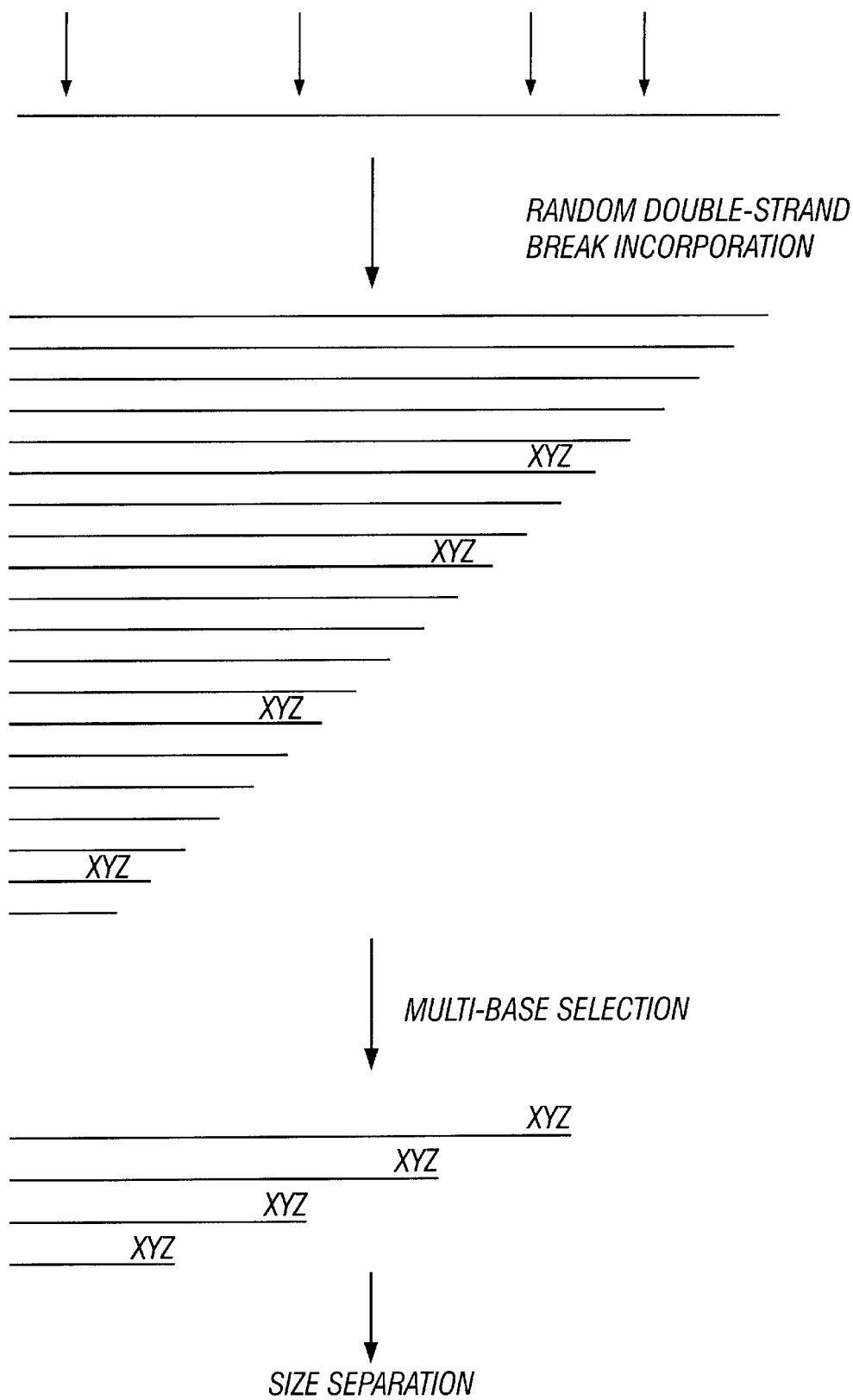
FIG. 31. Schematic representation of multi-base sequence analysis of randomly broken DNA as described in Example 10.

In addition to generating a nick that can be used to prime DNA synthesis and strand displacement, as described in detail herein above, the adaptor allows the set of molecules terminated at specific base combinations to be selected from the pool of randomly terminated DNA fragments (FIG. 31). The selection can be performed in a variety of ways, including using the procedures described herein above for selection and isolation mono-, di- or tri-nucleotide base combinations. The adaptor also allows the selected set of DNA fragments to be amplified using multiple primer-extension or PCR.

In this example the source DNA (DNA to be sequenced or mapped) is a PCR product, but linearized plasmid DNA can be also used. Furthermore, the use of a biotinylated primer and magnetic separations significantly simplifies the manipulations, but is not absolutely required.

A. Random Nick Formation

As described above, the adaptor can be used to generate a random nick, which can be used in conjunction with the walking and blocking (dd(-N)) methods described above. This protocol can be performed using an adaptor having a lower (C) strand that is not blocked at the 3' end, or, as described in detail below, by displacing the 3' blocked C strand and annealing a fresh, non-3' blocked C primer. These protocols allow for the selection of DNA fragments terminating in specific multi-base strings (for example $A_nT_mG$, where n and m are greater than or equal to 1).

B. Multi-Base Sequence Analysis

Figure 32:
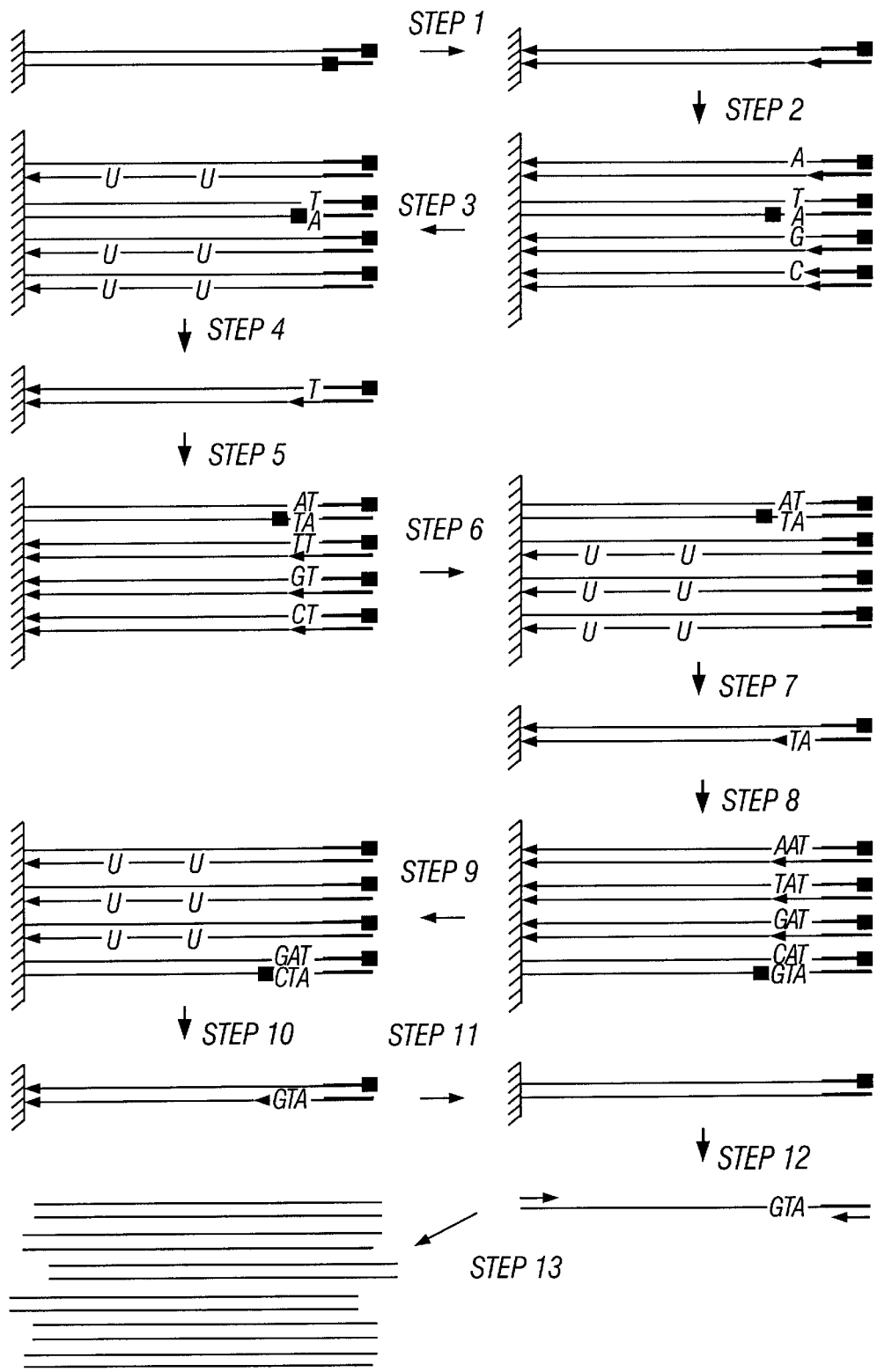
FIG. 32. Schematic representation of the sequential blocking-extension procedures as described in Example 10 for selection of DNA fragments that have 5'-ATG-3' base combination at their 5' adapted termini from a pool of randomly terminated DNA fragments. Filled squares indicate blocked 3'-ends; arrows indicate non-blocked 3'-OH ends.

This technique provides for the selection of DNA fragments with a specific base combination adjacent to the adaptor. It is achieved through a set of sequential biochemical reactions. For example, to select DNA fragments that have 5'-ATG-3' base combination at their 5' adapted termini, the following reactions are performed following the ligation of the adaptor as described above (FIG. 32). The excess, non-ligated adaptors are removed by washing, and the DNA sample is heated at a temperature sufficient to displace the bottom (C) strand, for example 65° C. Then a non-blocked C strand oligonucleotide is hybridized to the covalently attached oligo-adaptor W strand, and the excess W strand oligonucleotide is removed by washing.

Next, the sample is incubated with blocking solution "A", containing ddATP and an appropriate DNA polymerase, and then the sample is washed to remove the excess ddATP. During this step ddA is incorporated into the 3' ends of the C strand primers that associated with fragments having an adenine at the 5' position next to the adaptor, thus blocking these primers. The sample is then incubated with extension solution containing an appropriate DNA polymerase and dNTP mix with T substituted by dU. During this step all of the C-primers except those that are blocked by ddA will be extended.

Next, the DNA sample is heated at a temperature sufficient to displace the blocked C strand, for example 65° C., a new non-blocked oligonucleotide primer C-A (FIG. 30B, where X represents A), which has the same sequence as the C strand plus an adenine residue at the 3'-end, is hybridized to the W strand. During this step the C-A primer will bind only to DNA molecules which contain A at the 5' end adjacent to the adaptor, competing with the displaced ddA-blocked primers, as the other primers are stabilized by the extension step and cannot be displaced by the C-A primer. After the excess C-A primer is removed by washing, the DNA is incubated with blocking solution "T" (an appropriate DNA polymerase plus ddTTP), and the excess ddTTP is removed by washing. The DNA is then incubated with the dUTP containing extension solution as described above, and then the excess extension solution is removed by washing.

Next, the displacement (heating) and hybridization procedure as described above is repeated using a C-AT primer (C strand oligonucleotide plus AT at the 3' end; FIG. 30B, where X represents A and Y represents T). After removing the excess C-AT primer by washing, the DNA is then incubated with blocking solution "G" (an appropriate DNA polymerase plus ddGTP), and then the excess ddGTP is removed by washing. The DNA is then again incubated with the dU containing extension solution, as described above, and the excess solution is removed by washing.

Next, the displacement (heating) and hybridization procedure as described above is repeated using a C-ATG primer (C strand oligonucleotide plus ATG at the 3' end; FIG. 30B, where X represents A, Y represents T and Z represents G). After removing the excess C-ATG primer by washing, the DNA is incubated with extension buffer containing an appropriate DNA polymerase and dNTP mix without dUTP, wherein at least one of the dNTP's is labeled or incorporates an isolation tag. Then the DNA sample is incubated with dU-glycosylase, and heated to 95° C., to degrade all intermediate dU-containing extension products and the W strand of the adaptor (when uracil is incorporated in place of thymidine). The fully extended products, which have an ATG sequence at the 5' end adjacent the adaptor, are detected by a label incorporated into the extended strand, or by a label incorporated into the 5' end of the C-ATG primer. Alternatively, these strands can be isolated using a tag incorporated into the extended strands or the C-ATG primer, and then detected as described above.

Furthermore, using a standard adaptor as shown in FIG. 30A, single base sequencing can be performed on any fragment using the four C-X oligonucleotides (C-A, C-T, C-C and C-G), as shown in FIG. 30B. In a similar manner, two-base analysis can be conducted using the 16 C-XY oligonucleotides, and three-base analysis can be conducted using the 64 C-XYZ oligonucleotides.

The use of the C-ATG primer can be eliminated through the use of a blocking dd(-G) solution as described in detail above. In this case, after the C-AT oligonucleotide has been annealed, the DNA in incubated with blocking solution dd(-G) (an appropriate DNA polymerase plus ddNTP mix without ddGTP), and then washed. At this step all of the C-AT primers will be blocked by ddNTPs except those which have a G base in the next adjacent position. Then the DNA is incubated with extension buffer containing an appropriate DNA polymerase and dNTP mix without dUTP, and the DNA sample is incubated with dU-glycosylase, and heated to 95° C., to degrade all intermediate dU-containing extension products and the W strand of the adaptor (when uracil is incorporated in place of thymidine) as described above. The fully extended products can then be detected or isolated as described above. The fully extended products can also be used for linear amplification by primer extension or amplification by PCR.

Figure 33A:
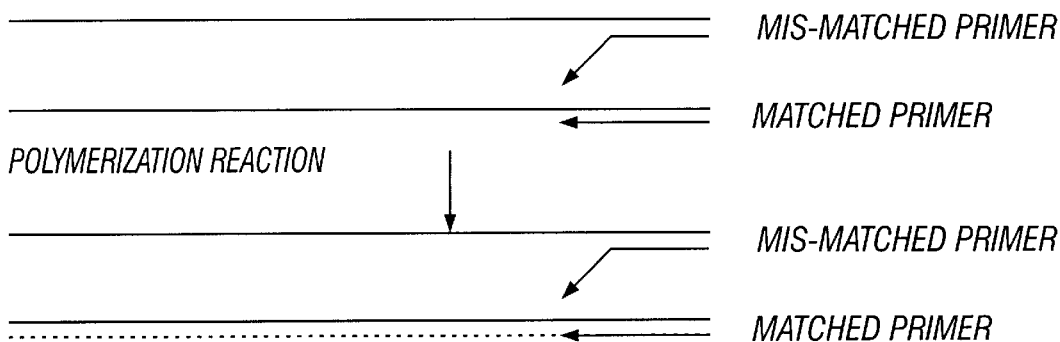
FIG. 33A and FIG. 33B. One-step selection procedures as described in Example 10.
Figure 33B:
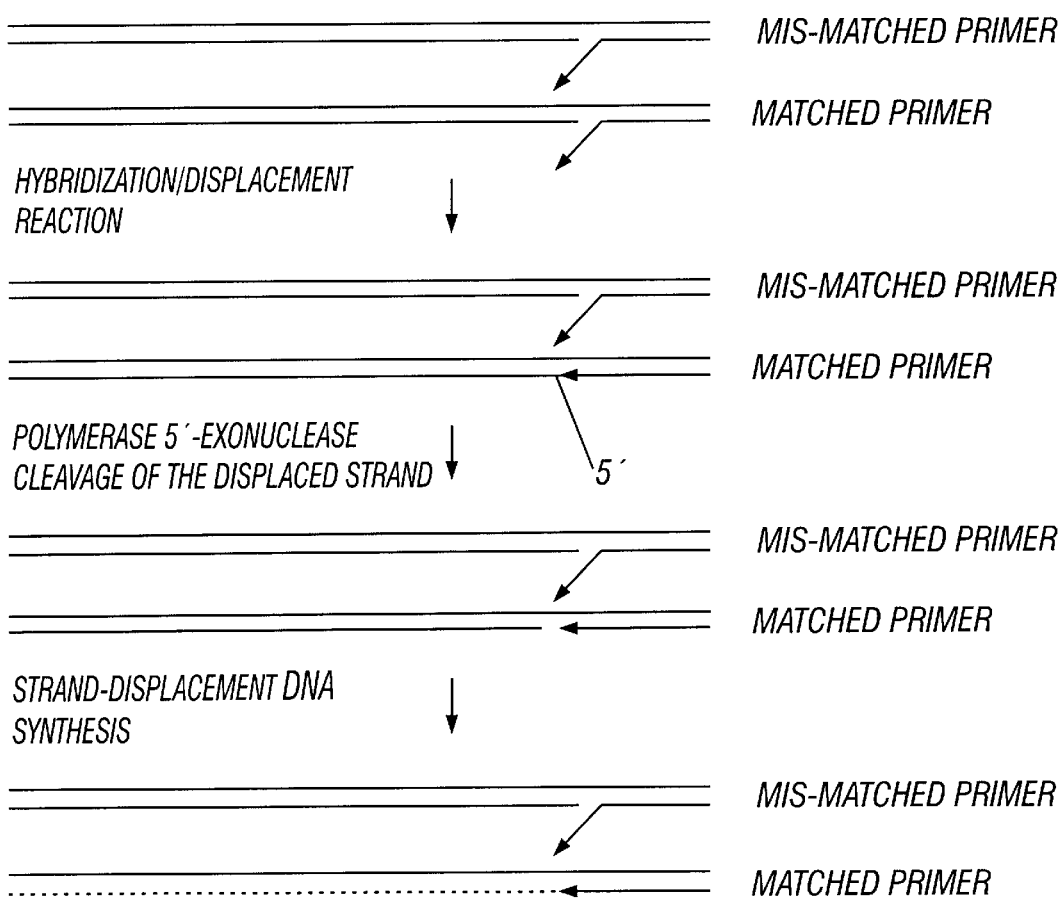

Alternatively, as shown in FIG. 33A, a single primer-selector can be hybridized to a single-stranded template, followed by incubation with an extension solution containing a dNTP mix and a DNA polymerase (Guilfoyle et al., 1997). Another method to perform the selection step on a double-stranded template in one step by using a single primer-selector is shown in FIG. 33B (Huang et al., 1992; Vos et al., 1995). For example, to select for the ATG combination the C-ATG primer is directly hybridized to DNA to displace the blocked C strand and a short region at the 5' end of the DNA fragment. The DNA is then incubated with the extension solution, containing dNTP mix and a DNA polymerase with 5' exonuclease activity.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,683,195, Mullis
U.S. Pat. No. 4,683,202, Mullis
U.S. Pat. No. 5,075,216
U.S. Pat. No. 5,091,328, Miller
Akhmetzjanov and Vakhitov, "Molecular cloning and nucleotide sequence of the DNA polymerase gene from *Thermus flavus*," *Nucl. Acids Res.*, 20:5839, 1992.
Ausubel et al., *Curr. Protocol Mol. Biol.*, 1(16), 1991.
Barnes, W. M., *Gene*, 112:29–35, 1992.
Berger and Kimmel, "Guide to Molecular Cloning Techniques," *Meth. Enzymol.*, 152:401, 1987.
Birren et al., *In: Pulsed field gel electrophoresis: a practical guide*, Academic Press, San Diego, 1993.
Campbell and Jackson, "The effect of divalent cations on the mode of action of DNase I. The initial reaction products produced from covalently closed circular DNA," *J. Biol. Chem.* 255:3726–3735, 1980.
Carter et al., *Nucl. Acids Res.*, 12:4431–4443,1985.
Connolly, *Nuc. Acids Res.* 15:3131–3139, 1987.
Crute and Lehman, "Herpes simplex-1 DNA polymerase. Identification of an intrinsic 5'-3' exonuclease with ribonuclease H. activity," *J. Biol. Chem.*, 264:19266, 1989.
Dixit et al., 1989), *J. Biol. Chem.*, 264:16905–16909, 1989.
Dotto and Zinder, "Reduction of the minimal sequence for initiation of DNA synthesis by qualitative or quantitative changes of an initiator protein," *Nature*, 311:279, 1984.
Doty et al., *Proc. Natl. Acad. Sci. USA*, 46:461, 1960.
Drmanac et al., "Sequencing of magabase plus DNA by hybridization: theory of the method," *Genomics*, 4:114, 1989.
Eckert, K. A. and Kunkel, T. A., *PCR Methods and Applications*, 1:17–24, 1991.
Eckstein, ed., Oligonucleotides and Analogues: A Practical Approach, IRL Press, Oxford, 1991.
Engler, M. J. et al., *J. Biol. Chem.*, 258:11165–11173, 1983.
Epe, B., D. Ballmaier, W. Adam, G. N. Grimm, and C. R. Saha-Moller. "Photolysis of N-hydroxypyridinethiones: a new source of hydroxyl radicals for the direct damage of cell-free and cellular DNA Ribonucleotide vanadyl complexes inhibit polymerase chain reaction," *Nuc. Acids Res.* 21:2777–2731, 1993.
Gibson et al, *Nuc. Acids Res.* 15:6455–6467, 1987.
Gomer and Firtel, "Sequencing homopolymer regions," *Bethesda Res. Lab. Focus*, 7:6, 1985.
Graham et al., "Direct DNA sequencing using avian myeloblastosis virus and Moleney murine leukemia virus reverse transcriptase," *Bethesda Res. Lab. Focus*, 8(2):4 1986.

Grant and Dervan, "Sequence-specific alkylation and cleavage of DNA mediated by purine motif triple helix formation," *Biochem.*, 35:12313, 1996.

Guilfoyle et al., "Ligation-mediated PCR amplification of specific fragments from a class-II restriction endonuclease total digest," *Nucl. Acids Res.* 25:1854–1858, 1997.

Gutman et al., "Identification, sequencing, and targeted mutagenesis of a DNA polymerase gene required for the extreme radioresistance of *Deinococcus radiodurans*," *J. Bacteriol.*, 175:3581, 1993.

Hacia et al, "Inhibition of Klenow fragment DNA polymerase on double-helical templates by oligonucleotide-directed triple-helix formation," *Biochem.*, 33:6192, 1994.

Haugland, Handbook of Fluorescent Probes and Research Chemicals, Molecular Probes, Inc., Eugene, 1992.

Hayes et al. "Footprinting protein-DNA complexes with gamma-rays," *Meth. Enzymol.* 186:545–549, 1990.

Henderson et al., *Cancer Cells*, 6:453–461, 1988.

Hertzberg and Dervan, "Cleavage of DNA with methidiumpropyl-EDTA-iron(II): reaction conditions and product analyses," *Biochemistry* 23:3934–3945, 1984.

Higashitani et al., "A single amino acid substitution reduces the superhelicity requirement of a replication initiator protein," *Nucl. Acids Res.*, 30:2685, 1992.

Hiriyanna and Ramakrishnan, "Purification and properties of DNA polymerase from *Mycobacterium tuberculosis* H37Rv," *Biochim. Biophys. Acta*, 652:274, 1981.

Ho et al., "Site-Directed Mutagenesis by Overlap Extension Using the Polymerase Chain Reaction," *Gene*, 77:51–59, 1989.

Holland et al., *Proc. Natl. Acad. Sci. USA*, 88:7276,1991.

Hori, K et al., *J. Biol. Chem.*, 254:11598–11604, 1979.

Huang et al., "Extension of base mispairs by Taq DNA polymerase: implications for single nucleotide discrimination in PCR," *Nucl. Acids Res.* 20:4567–4573, 1992.

Hultman et al., "Bi-directional solid phase sequencing of in vitro amplified DNA sequences," *BioTech.*, 10:84, 1990.

Hunkapiller, *Curr. Op. Gen. Devl.*, 1:88–92, 1991.

Hyman, "A new method of sequencing DNA," *Anal. Biochem.* 174:423–436, 1988.

Jablonski et al., *Nuc. Acids Res.* 14: 6115–6128, 1986.

Jones et al., "An iterative and regenerative method for DNA sequencing," *BioTechniques* 22:938–946, 1997.

Karanthanasis, "M13 DNA sequencing using reverse transcriptase," *Bethesda Res. Lab. Focus*, 4(3):6 1982.

Keller and Manak, DNA Probes, 2nd Edition, Stockton Press, New York, 1993.

Klimczak et al., "Purification and characterization of DNA polymerase from the archaebacterium *Mathanobacterium thermoautotrophicum*," *Biochem.*, 25:4850, 1986.

Kong et al., *Biol. Chem.*, 268:1965–1975, 1993.

Kornberg and Baker, In: *DNA Replication*, Freeman and Co., NY, 1992.

Kovacs et al., "The generation of a single nick per plasmid molecule using restriction endonucleases with multiple recognition sites," *Gene*, 29:63, 1984.

Kuby, *Immunology 2nd Edition*, W. H. Freeman & Company, NY, 1994.

Labeit, S., H. Lehrach, and R. S. Goody, "A new method of DNA sequencing using deoxynucleoside alpha-thiotriphosphates," *DNA* 5:173–177, 1986.

Labeit, S., H. Lehrach, and R. S. Goody, "DNA sequencing using alpha-thiodeoxynucleotides," *Meth. Enzymol.* 155:166–177, 1987.

Lagerqvist et al., "Manifold sequencing: Efficient processing of large sets of sequencing reactions," *Proc. Natl. Acad. Sci. USA*, 91:2245, 1994.

Longley et al, *Nucl. Acids Res.*, 18:7317, 1990.

Lopez et al., "Characterization of the polA gene of *Streptococcus pneumoniae* and comparison of the DNA polymerase I it encodes to homologous enzymes from *Escherichia coli* and phage T7," *J. Biol. Chem.*, 264:4255, 1989.

Makarov et al., *Cell*, 73:775–787, 1993.

Maloy et al., "Microbial Genetics" 2nd Edition. Jones and Bartlett Publishers, Boston, Mass., 1994.

Maniatis et al., "Molecular Cloning: a Laboratory Manual," Cold Spring Harbor Laboratory, Cold Spring Harbor, N.Y., 1982.

Marmur and Lane, *Proc. Natl. Acad. Sci. USA*, 46:453, 1960.

Matthews et al.,*Anal. Biochem.* 169:1–25, 1988.

Mattila, P. et al., *NAR*, 19:4967–4973, 1991.

Maxam and Gilbert, "A new method for sequencing DNA," *Proc. Natl. Acad. Sci. USA*, 74:560–564, 1977

Meyer and Geider, "Bacteriophage fd gene II-protein. I. Purification, involvement in RF replication, and the expression of gene II," *J. Biol. Chem.*, 254:12636, 1979.

Murphy, *Meth. Mol. Biol.*, 1993.

Myers and Gelfand, "Reverse transcription and DNA amplification by a *Thermus thermophilus* DNA polymerase," *Biochem.*, 30:7661, 1991.

Nakamaye, K. L., G. Gish, F. Eckstein, and H. P. Vosberg, "Direct sequencing of polymerase chain reaction amplified DNA fragments through the incorporation of deoxynucleoside alpha-thiotriphosphates," *Nucl. Acids Res.* 16:9947–9959, 1988.

Olsen et al., "Investigation of the inhibitory role of phosphorothioate internucleotidic linkages on the catalytic activity of the restriction endonuclease EcoRV," *Biochem.*, 29:9546, 1990.

Olsen, D. B. and F. Eckstein, "Incomplete primer extension during in vitro DNA amplification catalyzed by Taq polymerase; exploitation for DNA sequencing," *Nucl. Acids Res.* 17:9613–9620, 1989.

Pfahler et al., *Sensors and Actuators*, A21–A23, pp. 431–434, 1990.

Pilch et al., "Binding of a hairpin polyamide in the minor groove of DNA:sequence-specific enthalpic discrimination," *Proc. Natl. Acad. Sci. USA*, 93:8306, 1996.

Porter, K. W., J. D. Briley, and B. R. Shaw, "Direct PCR sequencing with boronated nucleotides," *Nucl. Acids Res.* 25:1611–1617, 1997.

Price and Tullius, "Using hydroxyl radicals to probe DNA structure," *Meth. Enzymol.* 212:194–219, 1992.

Prokop and Bajpai, *Ann. N.Y. Acad. Sci.* Vol. 646, 1991.

Ronghi et al., "Real-time DNA sequencing using detection of pyrophosphate release," *Anal. Biochem.* 242:84–89, 1996.

Ronghi et al., "A sequencing method based on real-time pyrophosphate," *Science* 281:363–365, 1998.

Sambrook et al., *In: Molecular Cloning, A Laboratory Manual*, 2d Ed., Cold Spring Harbor Laboratory Press, New York, pp. 13.7–13.9, 1989.

Sanger et al., "DNA Sequencing with Chain-Terminator Inhibitors," *Proc. Natl. Acad Sci. USA*, 74:5463–5467, 1977.

Segal, "Biochemical Calculations" 2nd Edition. John Wiley & Sons, New York, 1976.

Spoat et al., *Nuc. Acids Res.* 15:4837–4848, 1987.

Strobel and Dervan, "Triple helix-mediated single-site enzymatic cleavage of megabase genomic DNA," *Meth. Enzymol.*, 216:309, 1992.

Tabor and Richardson, EP 0 655 506 B1

Tabor and Richardson, *J. Biol. Chem.*, 264:6447–6458, 1989.

Tabor and Richardson, *J. Biol. Chem.*, 265:8322–8328, 1990.

Tabor et al., *Proc. Natl. Acad. Sci.* USA, 84:4767, 1987.

Tabor, S. and C. C. Richardson, "A single residue in DNA polymerases of the *Escherichia coli* DNA polymerase I family is critical for distinguishing between deoxy- and dideoxyribonucleotides," *Proc. Natl. Acad Sci. U. S. A.* 92:6339–6343, 1995.

Trauger et al., "Recognition of DNA by designed ligands at subnanomolar concentrations," *Nature,* 382:559, 1996.

Van Lintel et al., *Sensors and Actuators* 15:153–167, 1988.

Vos et al., "AFLP—a new technique for DNA fingerprinting," *Nucl. Acids Res.* 23:4407–4414, 1995.

Wetmur, *Critical Reviews in Biochemistry and Molecular Biology,* 26: 227–259, 1991.

What is claimed is:

1. A method of preparing a DNA molecule comprising:
   a) ligating an adaptor to the end of a template DNA molecule, wherein said ligation introduces a nick or gap site onto said template DNA molecule;
   b) initiating a nick translation reaction at the nick or gap site of said adaptor using a DNA polymerase having 5' to 3' exonuclease activity;
   c) allowing said nick translation reaction to proceed for a specific time to produce DNA fragments of similar size; and
   d) terminating said nick translation reaction.

2. The method of claim 1, wherein said adaptor comprises said nick or gap site.

3. The method of claim 2, wherein said adaptor comprises a double stranded DNA sequence and a nick or gap site comprising a single stranded DNA sequence.

4. The method of claim 1, wherein the terminating of said nick translation reaction at a specific time produces a DNA molecule of a desired length.

5. The method of claim 1, wherein the adaptor ligated DNA template is purified after said nick translation reaction is terminated.

6. The method of claim 5, wherein said purification is performed by electrophoresis.

7. The method of claim 1, wherein the product of said nick translation reaction is amplified.

8. The method of claim 1, wherein the product of said nick translation reaction is denatured.

9. The method of claim 8, wherein said denatured product is amplified.

10. The method of claim 9, wherein said amplification is linear amplification.

11. The method of claim 10, wherein said linear amplification is by primer extension.

12. The method of claim 7, wherein said amplification comprises an RNA polymerase.

13. The method of claim 11, wherein said primer extension reaction comprises a DNA polymerase.

14. The method of claim 11, wherein said primer extension reaction comprises a primer specific for said attached adaptor.

15. The method of claim 9, wherein said amplification is by PCR.

16. The method of claim 1, wherein said nick translation reaction incorporates at least one modified nucleic acid.

17. The method of claim 16, wherein said modified nucleic acid is exonuclease resistance.

18. The method of claim 16, wherein said modified nucleic acid is degradable.

19. The method of claim 16, wherein said modified nucleic acid comprises a label.

20. The method of claim 19, wherein said label is an affinity label.

21. The method of claim 19, wherein said label is a detectable label.

22. The method of claim 1, wherein the product of said nick translation reaction is cleaved.

23. The method of claim 22, wherein said cleavage is of the strand opposite said nick or gap site.

24. The method of claim 1, further comprising the step of using the product of said nick translation reaction in DNA mapping.

25. A method of preparing a DNA molecule comprising:
   a) ligating an adaptor to the end of a template DNA molecule, wherein said ligation introduces a nick or gap site onto said template DNA molecule, said nick or gap site comprised in said adaptor;
   b) initiating a nick translation reaction at the nick or gap site of said adaptor using a DNA polymerase having 5' to 3' exonuclease activity;
   c) allowing said nick translation reaction to proceed for a specific time; and
   d) terminating said nick translation reaction.

26. The method of claim 25, wherein the terminating of said nick translation reaction at a specific time produces a DNA molecule of a desired length.

27. The method of claim 25, wherein the adaptor ligated DNA template is separated purified after said nick translation reaction is terminated.

28. The method of claim 27, wherein said separation purification is performed by electrophoresis.

29. The method of claim 25, wherein the product of said nick translation reaction is amplified.

30. The method of claim 25, wherein the product of said nick translation reaction is denatured.

31. The method of claim 30, wherein said denatured product is amplified.

32. The method of claim 31, wherein said amplification is linear amplification.

33. The method of claim 32, wherein said linear amplification is by primer extension.

34. The method of claim 31, wherein said amplification comprises an RNA polymerase.

35. The method of claim 33, wherein said primer extension reaction comprises a DNA polymerase.

36. The method of claim 33, wherein said primer extension reaction comprises a primer specific or said attached adaptor.

37. The method of claim 31, wherein said amplification is by PCR.

38. The method of claim 25, wherein said nick translation reaction incorporates at least one modified nucleic acid.

39. The method of claim 38, wherein said modified nucleic acid is exonuclease resistance.

40. The method of claim 38, wherein said modified nucleic acid is degradable.

41. The method of claim 38, wherein said modified nucleic acid comprises a label.

42. The method of claim 41, wherein said label is an affinity label.

43. The method of claim 41, wherein said label is a detectable label.

44. The method of claim 25, wherein the product of said nick translation reaction is cleaved.

45. The method of claim 44, wherein said cleavage is of the strand opposite said nick or gap site.

46. The method of claim 25, further comprising the step of using the product of said nick translation reaction in DNA mapping.

* * * * *

UNITED STATES PATENT AND TRADEMARK OFFICE
CERTIFICATE OF CORRECTION

PATENT NO. : 6,197,557 B1  
DATED : March 6, 2001  
INVENTOR(S) : Vladimir L. Makarov and John P. Langmore Page 1 of 1

It is certified that error appears in the above-identified patent and that said Letters Patent is hereby corrected as shown below:

Title page,  
Item [63], Related U.S Application Data, please delete "Mar. 6, 1997," and insert -- Mar. 5, 1997, -- therefor.

Column 1,  
Line 7, please delete "Mar. 6, 1997," and insert -- Mar. 5, 1997, -- therefor.

Column 102, claim 36,  
Line 12, please delete "specific or said attached adaptor" and insert -- specific for said attached adaptor -- therefor.

Signed and Sealed this

Twenty-second Day of January, 2002

Attest:

*Attesting Officer*

JAMES E. ROGAN  
*Director of the United States Patent and Trademark Office*

SEQUENCE LISTING

<160> NUMBER OF SEQ ID NOS: 14

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Strand
      displacement primer

<400> SEQUENCE: 1
cccuaacccu aacccuaacc cuaa                                          24

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide is used as a probe

<400> SEQUENCE: 2
ccctaaccct aaccctaacc c                                             21

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide is used as a probe

<400> SEQUENCE: 3
uuaggguuag gguuagggu aggg                                           24

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide is used as a probe

<400> SEQUENCE: 4
ccctccagcg gccggttagg gttagggtta ggg                                33

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Strand
      displacement primer

```
<400> SEQUENCE: 5
ccctaaccct aaccctaacc ctaa                                    24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide is used as a probe

<400> SEQUENCE: 6
ttagggttag ggttagggtt aggg                                    24

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Primer used
      for sequencing

<400> SEQUENCE: 7
aaaacgaggt ccacggtatc gt                                      22

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide used as a sequencing template

<400> SEQUENCE: 8
caggatgtga ccctccagca cataggtcta cg                           32

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Primer used
      for sequencing

<400> SEQUENCE: 9
ggtcgtgtat ccagatgcca g                                       21

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Primer used
      for sequencing

<400> SEQUENCE: 10
gaggtcgtgt atccagatgc cag                                     23

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Primer used
      for sequencing
```

```
<400> SEQUENCE: 11
gggaggtcgt gtatccagat gccag                                          25

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Primer used
      for sequencing

<400> SEQUENCE: 12
actgggaggt cgtgtatcca gatgccag                                       28

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide used as a PCR primer
<220> FEATURE:
<221> NAME/KEY: misc_feature
<222> LOCATION: (1)
<223> OTHER INFORMATION: biotin attached to 5' end

<400> SEQUENCE: 13
ggtaacagga ttagcagagc gagg                                           24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide used as a PCR primer

<400> SEQUENCE: 14
ttatctacac gaagggagt caga                                            24
```